US009988492B2

(12) United States Patent
Becker et al.

(10) Patent No.: US 9,988,492 B2
(45) Date of Patent: Jun. 5, 2018

(54) METHODS FOR POST-FABRICATION FUNCTIONALIZATION OF POLY(ESTER UREAS)

(71) Applicants: Matthew Becker, Stow, OH (US); Fei Lin, Akron, OH (US)

(72) Inventors: Matthew Becker, Stow, OH (US); Fei Lin, Akron, OH (US)

(73) Assignee: The University of Akron, Akron, OH (US)

(*) Notice: Subject to any disclaimer, the term of this patent is extended or adjusted under 35 U.S.C. 154(b) by 90 days.

(21) Appl. No.: 15/026,069

(22) PCT Filed: Sep. 30, 2014

(86) PCT No.: PCT/US2014/058264
§ 371 (c)(1),
(2) Date: Mar. 30, 2016

(87) PCT Pub. No.: WO2015/048728
PCT Pub. Date: Apr. 2, 2015

(65) Prior Publication Data
US 2016/0237212 A1 Aug. 18, 2016

Related U.S. Application Data

(60) Provisional application No. 61/884,166, filed on Sep. 30, 2013.

(51) Int. Cl.
*A61K 31/00* (2006.01)
*C08G 71/02* (2006.01)
(Continued)

(52) U.S. Cl.
CPC ............ *C08G 71/02* (2013.01); *C07C 227/18* (2013.01); *C07C 229/34* (2013.01);
(Continued)

(58) Field of Classification Search
CPC ... C07C 275/16; C07C 227/18; C07C 229/34; C07C 247/04; C08G 71/02; C08G 2230/00; C09D 175/02
(Continued)

(56) References Cited

U.S. PATENT DOCUMENTS

2005/0271700 A1 12/2005 Desnoyer, Jr. et al.
2006/0177416 A1* 8/2006 Turnell ................ A61K 9/1075
424/78.27
(Continued)

FOREIGN PATENT DOCUMENTS

WO 2008048298 4/2008

*Primary Examiner* — William Cheung
(74) *Attorney, Agent, or Firm* — Renner Kenner Greive Bobak Taylor & Weber

(57) ABSTRACT

Amino acid-based poly(ester urea)s (PEU) are emerging as a class of polymers that have shown promise in regenerative medicine applications. Embodiments of the invention relate to the synthesis of PEUs carrying pendent "clickable" groups on modified tyrosine amino acids. The pendent species include alkyne, azide, alkene, tyrosine-phenol, and ketone groups. PEUs with $M_w$ exceeding 100k Da were obtained via interfacial polycondensation methods and the concentration of pendent groups was varied by copolymerization. The incorporation of derivatizable functionalities is demonstrated using $^1$H NMR and UV-Vis spectroscopy methods. Electrospinning was used to fabricate PEU nanofibers with a diameters ranging from 350 nm to 500 nm. The nanofiber matricies possess mechanical strengths suitable for tissue engineering (Young's modulus: 300±45 MPa; tensile stress: 8.5±1.2 MPa). A series of bioactive peptides and fluorescent molecules were conjugated to the surface of the nanofibers following electrospinning using bio-orthogonal reactions in aqueous media.

24 Claims, 30 Drawing Sheets

(51) Int. Cl.
  *C07C 275/16* (2006.01)
  *C07C 227/18* (2006.01)
  *C07C 229/34* (2006.01)
  *C07C 247/04* (2006.01)
  *C09D 175/02* (2006.01)

(52) U.S. Cl.
  CPC .......... *C07C 247/04* (2013.01); *C07C 275/16* (2013.01); *C09D 175/02* (2013.01); *C08G 2230/00* (2013.01)

(58) Field of Classification Search
  USPC .......................................... 424/78.27; 514/44
  See application file for complete search history.

(56) References Cited

U.S. PATENT DOCUMENTS

| | | |
|---|---|---|
| 2007/0128250 A1 | 6/2007 | Katsavara et al. |
| 2010/0040880 A1 | 2/2010 | Koopmans et al. |
| 2012/0052097 A1 | 3/2012 | Fetzer et al. |
| 2012/0226013 A1 | 9/2012 | Kohn et al. |
| 2013/0253135 A1 | 9/2013 | Barrett et al. |

\* cited by examiner

▶ : Pendent Functional Group (e.g. an alkyne, azide, or alkene group)

▶ : Pendent functional group (e.g. alkyne, azide, or alkene group)

⬅—✦ : Fluorescence labeled biomolecules with corresponding "clickable" functional groups Small molecule probes with corresponding reactive groups

- Success of derivation is demonstrated via NMR
- Reactive groups available for post-polymerization modification

METHODS FOR POST-FABRICATION FUNCTIONALIZATION OF POLY(ESTER UREAS)

CROSS REFERENCE TO RELATED APPLICATIONS

This application claims the benefit of International Application Number PCT/US2014/58264 entitled "Methods for Post-Fabrication Functionalization of Poly(ester ureas)," and filed Sep. 30, 2014, and U.S. provisional patent application Ser. No. 61/884,166 entitled "Methods for Post-Fabrication Functionalization of Poly(ester ureas)," filed Sep. 30, 2013, both of which are incorporated herein by reference in their entirety.

REFERENCE TO GOVERNMENT SUPPORT

The invention was made with government support under grant number DMR-BMAT 1105329 awarded by the National Science Foundation. The government has certain rights in the invention.

FIELD OF THE INVENTION

One or more embodiments of the present invention relates to a functionalized poly(ester urea). In certain embodiments, the present invention relates to novel tyrosine-based monomers and poly(ester urea)s functionalized to bond with a bioactive molecule via one or more "click" reactions and related methods.

BACKGROUND OF THE INVENTION

Over the last few decades, biodegradable polymers have been applied to a number of applications in drug delivery and regenerative medicine. While naturally derived biodegradable polymers have distinct bioactivity and cell binding properties, they are difficult to isolate, derivatize and purify. Synthetic polymers also have the potential for immunogenic responses. Synthetic biodegradable polymers have a number of advantages over natural materials, especially the chemical diversity of monomers that can be utilized to tailor the chemical, mechanical and degradation properties of the polymer. There are a number of biodegradable polymers including poly(ε-caprolactone) (PCL), poly(lactic acid) (PLA), poly(glycolide) (PGA), and copolymers thereof that are used clinically and while their properties in vitro and in vivo are largely understood, their range of physical and chemical properties is somewhat limited. Efforts have been made to diversify the pool of synthetic polymers to meet design criteria for more advanced applications. Currently, a wide range of polymers including polyurethanes, polycarbonates and poly(α-amino acids) have been utilized in biomedical and regenerative applications.

More recently, amino acid-based poly(ester urea)s (PEUs) have been studied for use in various biomedical and regenerative applications. The use of specific amino acids influences the physical and chemical properties of the resulting polymers and also provides significant variability in the chemical structures. Amino acid-based PEUs are semicrystalline, and thermal or solution-based processing methods offer non-chemical routes to tune their mechanical properties, chemical stability and degradation rates. To further enhance the biological interactions, there has been a focus on attaching bioactive molecules to these polymers. Conventionally, the bioactive molecules are attached to the PEU polymer prior to processing the PEU into a desired form or configuration for use. However, attaching bioactive molecules like peptides or proteins prior to processing is generally difficult and the biological activity is often lost due to denaturation or degradation.

The incorporation of reactive sites into biodegradable polymers provides a platform for the conjugation of biological cues. To meet the challenge of regiospecific biomolecular derivation, it is particularly attractive to employ orthogonal "click" chemistry methods. The "click" concept currently represents a number of reactions, which are robust, selective, efficient, and high yielding. The catalog of "click" reactions includes copper (I) catalyzed azide-alkyne cycloaddition (CuAAC), thiol-ene radical addition, oxime ligation, Michael-addition, among others. They are widely utilized for protein and DNA conjugation, cell modification, surface functionalization, and in vivo signaling. Other "click" reactions, such as thiol-maleimide and NHS-ester coupling, are also widely used in the fields of material and life science.

Recently, "click" chemistry has been used for protein and peptide conjugation to tyrosine-based phenol residues using both Mannich-type addition and "ene-type" addition reactions. Compared to the large abundance of lysine residues typically found in proteins, the tyrosine content is much lower. In addition, unlike the disulfide linkages and bridges enabled by cysteine residues in close proximity, tyrosine is available for chemical modification without additional protection/deprotection steps.

What is needed in the art is a novel tyrosine-based PEUs functionalized specifically to bond with bioactive molecules via a click reaction after the PEU has been processed into its intended final form and/or composition and related methods of attaching bioactive molecules to the tyrosine-based PEUs using "click" chemistry reactions.

SUMMARY OF THE INVENTION

One or more embodiments of the present invention provide a novel tyrosine-based PEUs functionalized to bond with bioactive molecules via a click reaction after the PEU has been processed into its final intended form and/or composition and related methods of attaching bioactive molecules to novel tyrosine-based PEUs using "click" reactions.

In a first aspect, the present invention provides an amino acid based poly(ester urea) polymer functionalized to bond with a bioactive compound comprising a phenylalanine-based monomer segment and a tyrosine-based monomer segment, the tyrosine-based monomer segment having one or more pendent functional groups. In some embodiments, present invention is directed to the amino acid based poly (ester urea) of the first aspect of the present invention wherein the one or more pendent functional groups is functionalized to bond with a bioactive compound via a click reaction.

In one or more embodiments, the amino acid based poly(ester urea) polymer of the present invention includes any one or more of the above referenced embodiments of the first aspect of the present invention wherein the click reaction selected from the group consisting of Huisgen cycloaddition reactions, copper (I) catalyzed azide-alkyne cycloaddition (CuAAC) reactions, thiol-ene radical addition reactions, oxime ligation reactions, Michael-addition reactions, Mannich-type addition reactions, "ene-type" addition reactions, strain promoted azide-alkyne cycloaddition (SPAAC) reactions, Diels-Alder reactions, and combinations thereof.

In one or more embodiments, the amino acid based poly(ester urea) polymer of the present invention includes any one or more of the above referenced embodiments of the first aspect of the present invention wherein the phenylalanine-based monomer segment has the formula:

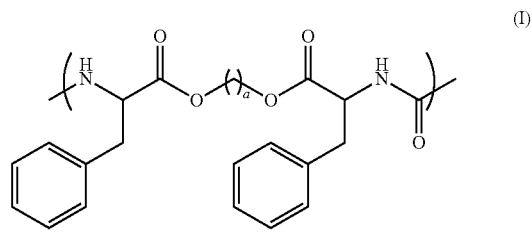

wherein a is an integer from 2 to 12.

In one or more embodiments, the amino acid based poly(ester urea) polymer of the present invention includes any one or more of the above referenced embodiments of the first aspect of the present invention wherein the tyrosine-based monomer segment has the formula:

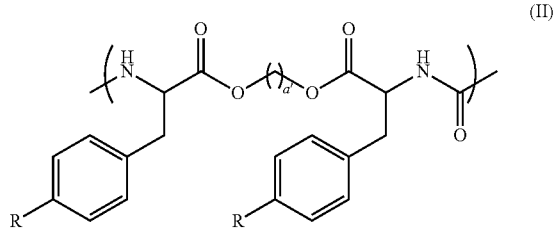

(II)

wherein R is the one or more pendent functional groups and a' is an integer from 2 to 12.

In one or more embodiments, the amino acid based poly(ester urea) polymer of the present invention includes any one or more of the above referenced embodiments of the first aspect of the present invention wherein the pendent functional group further comprises an alkyne group, an alkene group, an azide group, a benzyl protected phenol group, a ketone group, or a strained cyclooctyne. In one or more embodiments, the amino acid based poly(ester urea) polymer of the present invention includes any one or more of the above referenced embodiments of the first aspect of the present invention wherein R is OH, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

In one or more embodiments, the amino acid based poly(ester urea) polymer of the present invention includes any one or more of the above referenced embodiments of the first aspect of the present invention having the formula:

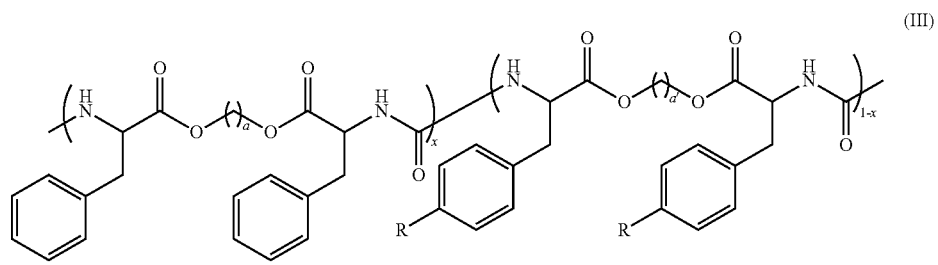

(III)

wherein R is an oxygen atom connected to a alkyl or aryl group containing an alkyne group, an alkene group, an azide group, a benzyl protected phenol group, a ketone group or a strained cyclooctyne; x is a mole fraction of from 0.001 to 0.200; and a and a' are integers from 2 to 12. In one or more embodiments, the amino acid based poly(ester urea) polymer of the present invention includes any one or more of the above referenced embodiments of the first aspect of the present invention wherein R is OH, $OCH_2C\equiv CH$, $OCH_2CH_2CH_2N_3$, $OCH_2CH_2CH_2CH=CH_2$, $OCH_2Ph$, $OCOCH_2CH_2COCH_3$.

In one or more embodiments, the amino acid based poly(ester urea) polymer of the present invention includes any one or more of the above referenced embodiments of the first aspect of the present invention having a formula selected from the group consisting of:

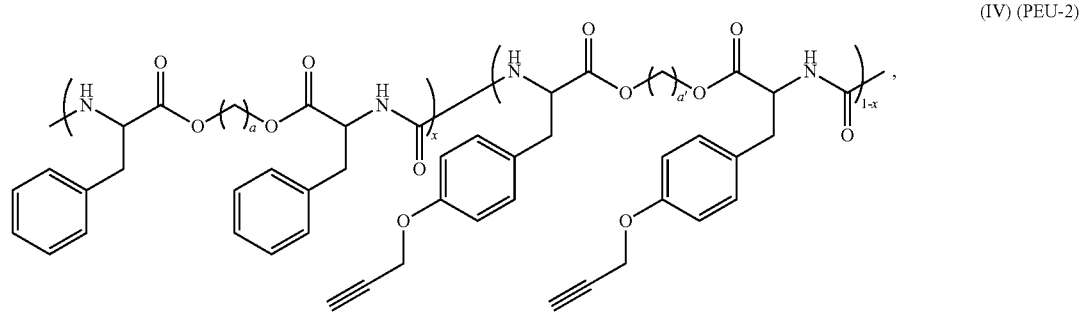

(IV) (PEU-2)

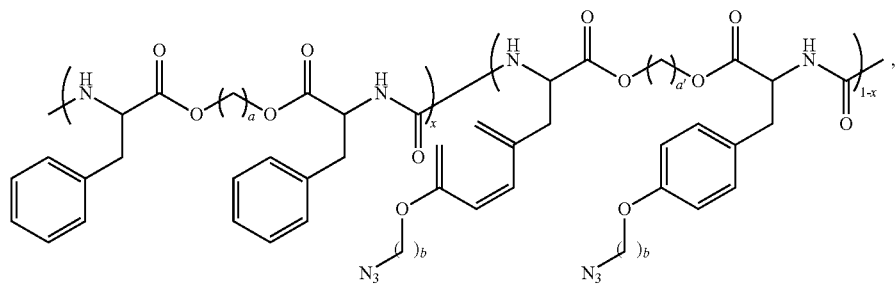
(V) (PEU-2)
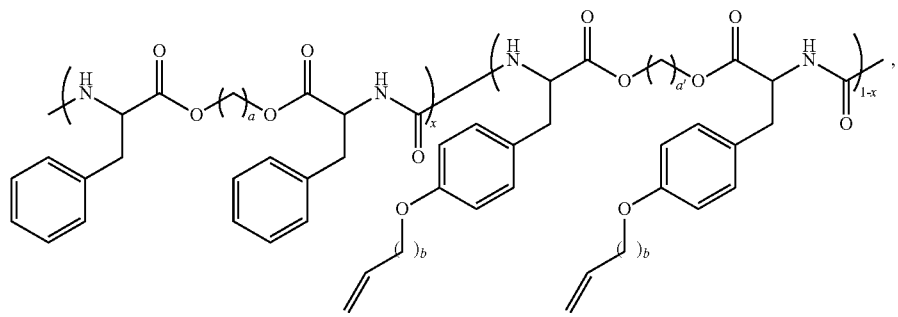
(VI) (PEU-4)
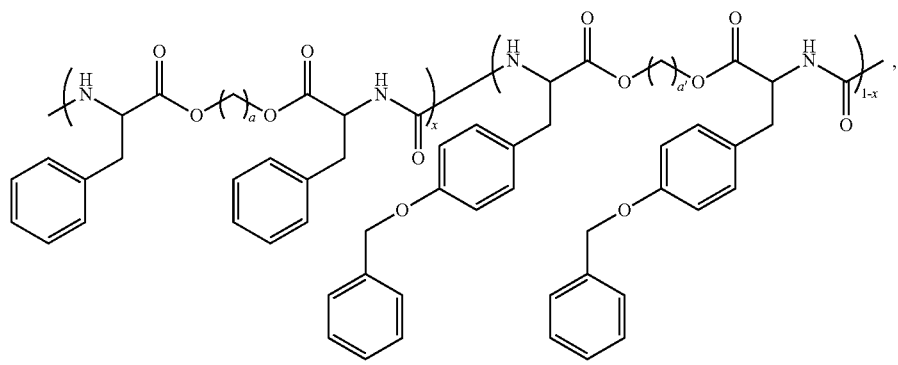
(VII) (PEU-5)
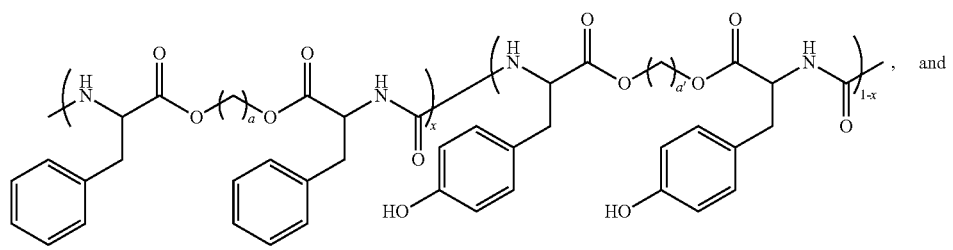
(VIII) (PEU-6), and
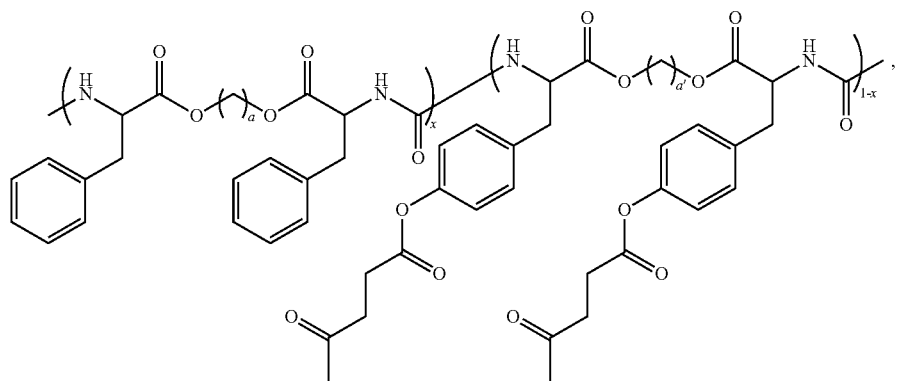
(IX) (PEU-7)

wherein a and a' are each an integer from 2 to 12; b is an integer from 1 to 8; and x is a molar fraction from 0.001 to 0.200. In one or more embodiments, the amino acid based poly(ester urea) polymer of the present invention includes any one or more of the above referenced embodiments of the first aspect of the present invention having a mole average molecular weight of from about 3000 da to about 300,000 da.

In one or more embodiments, the amino acid based poly(ester urea) polymer of the present invention includes any one or more of the above referenced embodiments of the first aspect of the present invention further comprising a bioactive compound chemically bound to the one or more pendent functional groups. In one or more embodiments, the amino acid based poly(ester urea) polymer of the present invention includes any one or more of the above referenced embodiments of the first aspect of the present invention wherein the bioactive compound is selected from the group consisting of peptides, carbohydrates, and growth factors, and combinations thereof. In one or more embodiments, the amino acid based poly(ester urea) polymer of the present invention includes any one or more of the above referenced embodiments of the first aspect of the present invention wherein the bioactive compound is selected from the group consisting of Lys(biotin), bone morphogenic protein-2 (BMP-2), bone morphogenic protein-7 (BMP-7), osteogenic growth peptide (OGP), the c-terminal fragment of OGP [10-14] (YGFGG), GRGDS (RGD), and combinations thereof.

In a second aspect, the present invention provides a formed polymer structure, coating or film comprising an amino acid based poly(ester urea) polymer functionalized to bond with a bioactive compound, wherein the amino acid based poly(ester urea) polymer further comprises: a phenylalanine-based monomer segment and a tyrosine-based monomer segment, the tyrosine-based monomer segment having one or more pendent functional groups. In some embodiments, present invention is directed to the formed polymer structure, coating or film of the second aspect of the present invention wherein the formed polymer structure, coating or film comprises a fiber, a tissue scaffold, a tube, a pin, a film, a coating, or a medical device. In one or more embodiments, the formed polymer structure, coating or film of the present invention includes any one or more of the above referenced embodiments of the second aspect of the present invention wherein the formed polymer structure, coating or film is a microfiber or nanofiber.

In one or more embodiments, the formed polymer structure, coating or film of the present invention includes any one or more of the above referenced embodiments of the second aspect of the present invention wherein the one or more pendent functional groups further comprises a moiety selected from the group consisting of alkynes, alkenes, azides, benzyl-protected phenol groups, ketones, strained cyclooctynes, and combinations thereof. In one or more embodiments, the formed polymer structure, coating or film of the present invention includes any one or more of the above referenced embodiments of the second aspect of the present invention wherein the tyrosine-based monomer segment has the formula:

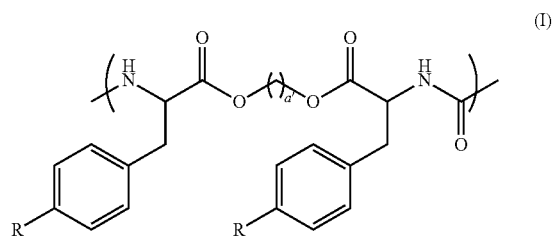

wherein R is a pendent functional group and a' is an integer from 2 to 12.

In one or more embodiments, the formed polymer structure, coating or film of the present invention includes any one or more of the above referenced embodiments of the second aspect of the present invention wherein R further comprises an oxygen atom connected to an alkyl or aryl group containing a moiety capable of forming a chemical bond through a click reaction. In one or more embodiments, the formed polymer structure, coating or film of the present invention includes any one or more of the above referenced embodiments of the second aspect of the present invention wherein the moiety comprises an alkyne group, an alkene group, an azide group, a benzyl protected phenol group, or a ketone group. In one or more embodiments, the formed polymer structure, coating or film of the present invention includes any one or more of the above referenced embodiments of the second aspect of the present invention wherein R further comprises a hydroxyl or a benzyl protected phenol group.

In one or more embodiments, the formed polymer structure, coating or film of the present invention includes any one or more of the above referenced embodiments of the second aspect of the present invention wherein R is selected from OCH$_2$C≡CH, OCH$_2$CH$_2$CH$_2$N$_3$, OCH$_2$CH$_2$CH$_2$CH=CH$_2$, OCOCH$_2$CH$_2$COCH$_3$, and combinations thereof. In one or more embodiments, the formed polymer structure, coating or film of the present invention includes any one or more of the above referenced embodiments of the second aspect of the present invention wherein R is selected from OH or OCH$_2$Ph and combinations thereof.

In one or more embodiments, the formed polymer structure, coating or film of the present invention includes any one or more of the above referenced embodiments of the second aspect of the present invention wherein the amino acid based poly(ester urea) polymer has the formula:

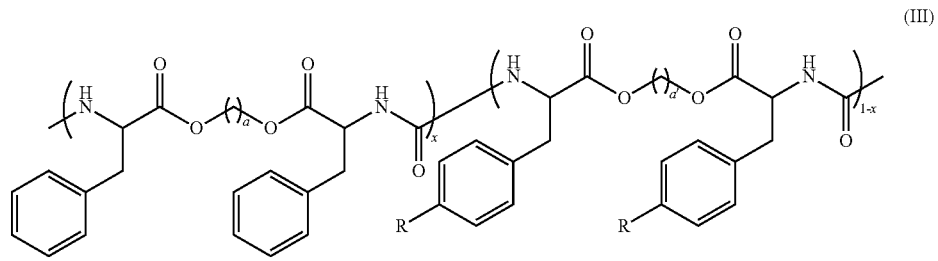

wherein R is a pendent functional group; x is a mole fraction of from 0.001 to 0.200; and a and a' are each an integer from 2 to 12.

In one or more embodiments, the formed polymer structure, coating or film of the present invention includes any one or more of the above referenced embodiments of the second aspect of the present invention wherein R is an oxygen atom connected to a alkyl or aryl group containing a functional group capable of forming a chemical bond through a click reaction In one or more embodiments, the formed polymer structure, coating or film of the present invention includes any one or more of the above referenced embodiments of the second aspect of the present invention wherein R is an oxygen atom connected to a alkyl or aryl group containing an alkyne group, an alkene group, an azide group, or a ketone group. In one or more embodiments, the formed polymer structure, coating or film of the present invention includes any one or more of the above referenced embodiments of the second aspect of the present invention wherein R is a hydroxyl group or a benzyl protected phenol group. In one or more embodiments, the formed polymer structure, coating or film of the present invention includes any one or more of the above referenced embodiments of the second aspect of the present invention wherein R further comprises OH, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

In one or more embodiments, the formed polymer structure, coating or film of the present invention includes any one or more of the above referenced embodiments of the second aspect of the present invention wherein the amino acid based poly(ester urea) polymer has a formula selected from the group consisting of:

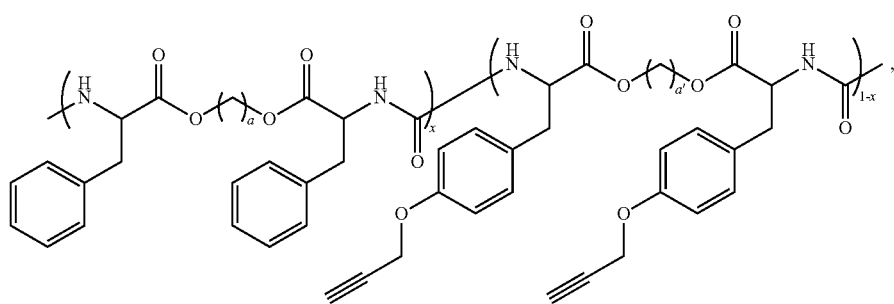

(IV) (PEU-2)

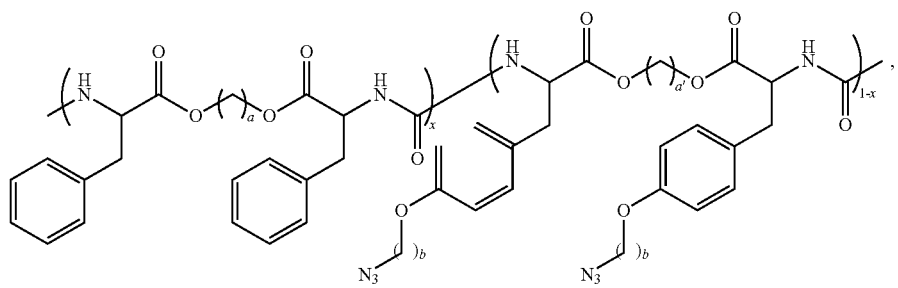

(V) (PEU-2)

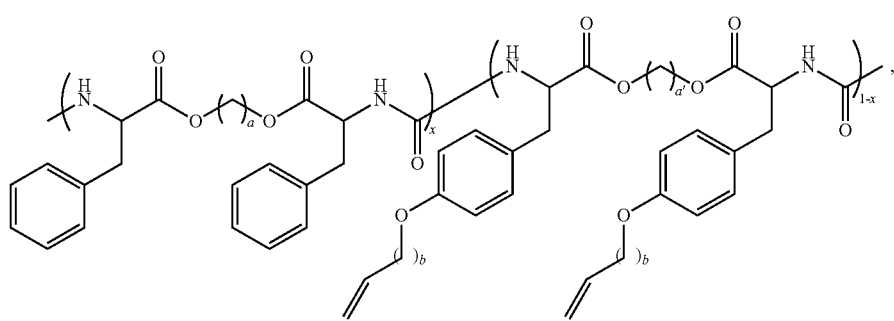

(VI) (PEU-4)

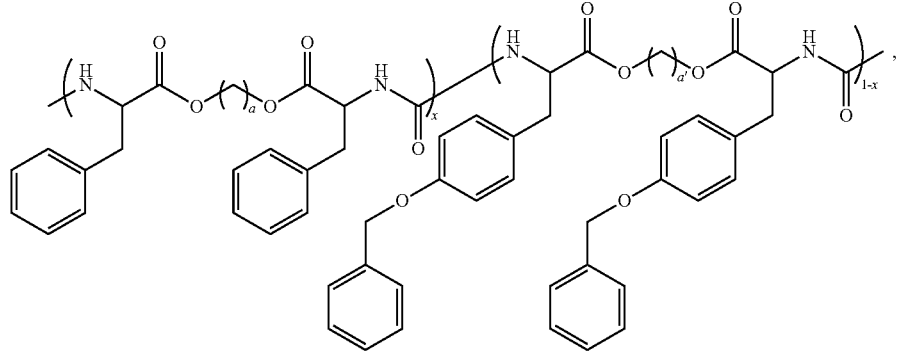

(VII) (PEU-5)

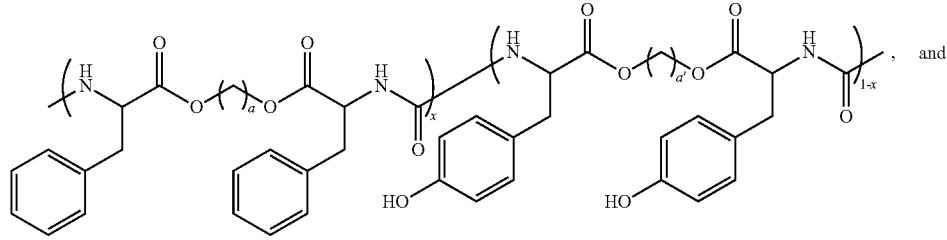

(VIII) (PEU-6), and

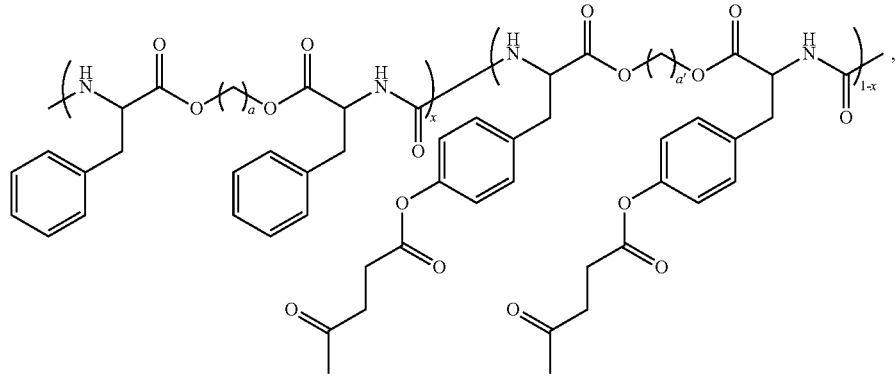

(IX) (PEU-7), wherein a and a' are each an integer from 2 to 12; b is an integer from 1 to 8; x is a mole fraction of from 0.001 to 0.2.

In one or more embodiments, the formed polymer structure, coating or film of the present invention includes any one or more of the above referenced embodiments of the second aspect of the present invention further comprising: a bioactive compound chemically bound to the one or more pendent functional groups of the amino acid based poly (ester urea) polymer. In one or more embodiments, the formed polymer structure, coating or film of the present invention includes any one or more of the above referenced embodiments of the second aspect of the present invention wherein the bioactive compound comprises a peptide, a carbohydrate, or a growth factor. In one or more embodiments, the formed polymer structure, coating or film of the present invention includes any one or more of the above referenced embodiments of the second aspect of the present invention wherein the bioactive compound is selected from the group consisting of bone morphogenic protein-2 (BMP-2), bone morphogenic protein-7 (BMP-7), osteogenic growth peptide (OGP), the c-terminal fragment of OGP [10-14] (YGFGG), GRGDS (RGD), and combinations thereof.

In a third aspect, the present invention provides the reaction product of: a phenylalanine-based monomer; and a tyrosine-based monomer having one or more pendent functional groups. In some embodiments, present invention is directed to the reaction product of the third aspect of the present invention further comprising: a bioactive compound functionalized to chemically bind to the one or more pendent functional groups.

In one or more embodiments, the reaction product of the present invention includes any one or more of the above referenced embodiments of the third aspect of the present invention wherein the phenylalanine-based monomer segment has the formula:

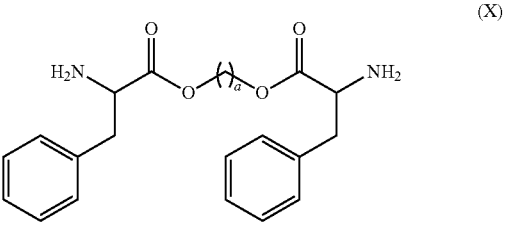

(X)

wherein a is an integer from 2 to 12. In one or more embodiments, the reaction product of the present invention includes any one or more of the above referenced embodiments of the third aspect of the present invention wherein the tyrosine-based monomer has the formula:

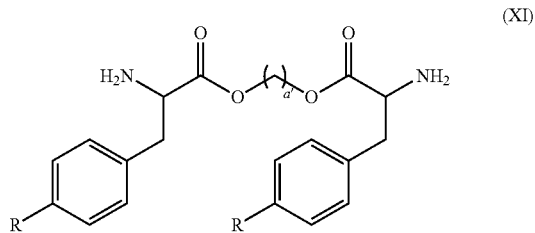
(XI)

wherein R is an pendent functional group and a' is an integer from 2 to 12. In one or more embodiments, the reaction product of the present invention includes any one or more of the above referenced embodiments of the third aspect of the present invention wherein R comprises an oxygen atom connected to an alkyl or aryl group containing a moiety capable of forming a chemical bond through a click reaction In one or more embodiments, the reaction product of the present invention includes any one or more of the above referenced embodiments of the third aspect of the present invention wherein the moeity comprises an alkyne group, an alkene group, an azide group, a benzyl protected phenol group, or a ketone group. In one or more embodiments, the reaction product of the present invention includes any one or more of the above referenced embodiments of the third aspect of the present invention wherein the moeity comprises a hydroxyl or a benzyl protected phenol group. In one or more embodiments, the reaction product of the present invention includes any one or more of the above referenced embodiments of the third aspect of the present invention wherein R is OH $OCH_2C\equiv CH$, $OCH_2CH_2CH_2N_3$, $OCH_2CH_2CH_2CH=CH_2$, $OCH_2Ph$, or $OCOCH_2CH_2COCH_3$.

In one or more embodiments, the reaction product of the present invention includes any one or more of the above referenced embodiments of the third aspect of the present invention having a formula:

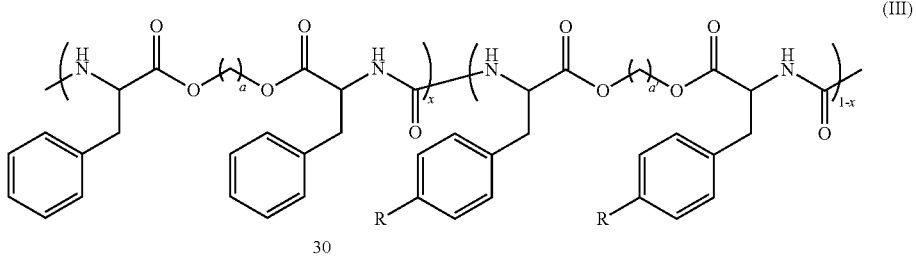
(III)

wherein R is pendent functional group; x is a mole fraction of from 0.001 to 0.200; and a and a' are each an integer from 2 to 12.

In one or more embodiments, the reaction product of the present invention includes any one or more of the above referenced embodiments of the third aspect of the present invention wherein R is an oxygen atom connected to an alkyl or aryl group containing a functional group capable of forming a chemical bond through a click reaction. In one or more embodiments, the reaction product of the present invention includes any one or more of the above referenced embodiments of the third aspect of the present invention wherein R is an oxygen atom connected to a alkyl or aryl group containing an alkyne group, an alkene group, an azide group, a benzyl protected phenol group, or a ketone group. In one or more embodiments, the reaction product of the present invention includes any one or more of the above referenced embodiments of the third aspect of the present invention wherein R is OH, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

In one or more embodiments, the reaction product of the present invention includes any one or more of the above referenced embodiments of the third aspect of the present invention having a formula selected from:

(IV) (PEU-2)

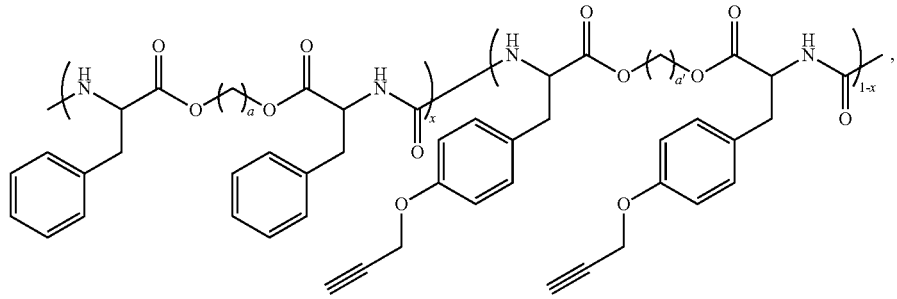

-continued
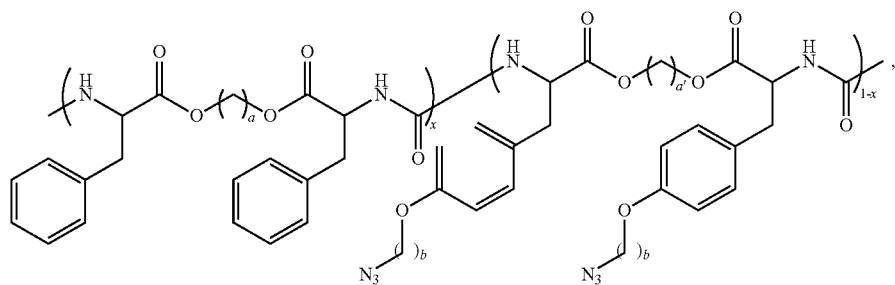 (V) (PEU-2)
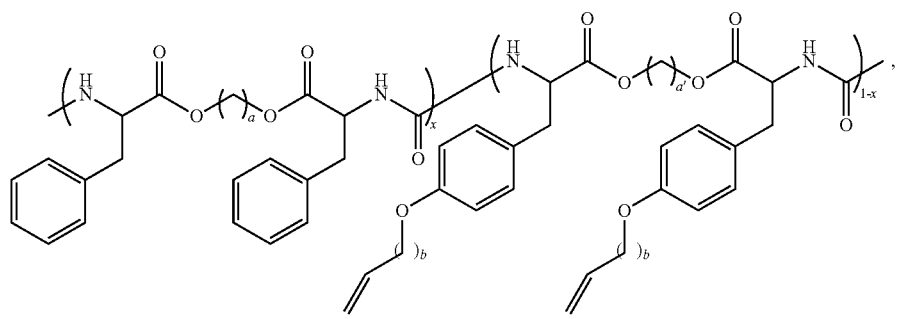 (VI) (PEU-4)
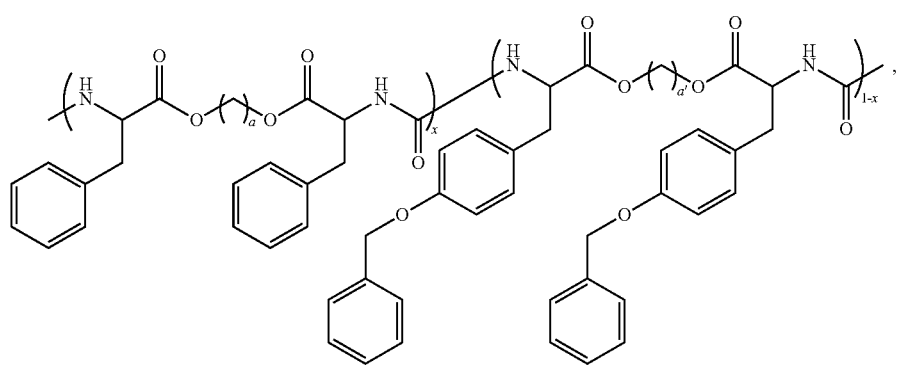 (VII) (PEU-5)
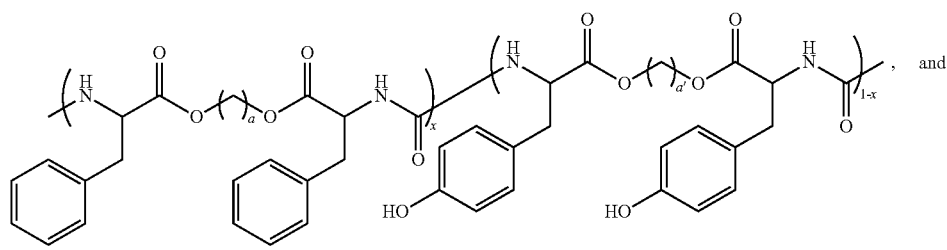 (VIII) (PEU-6), and
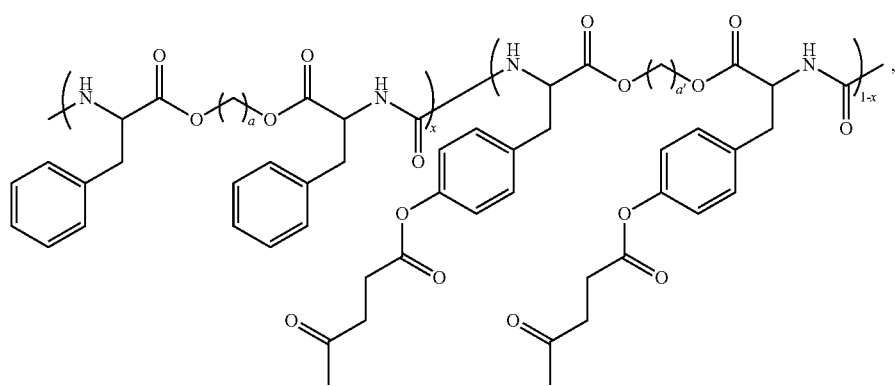 (IX) (PEU-7)

wherein a and a' are each an integer from 2 to 12; b is an integer from 1 to 8; and x is a mole fraction of from 0.001 to 0.20.

In one or more embodiments, the reaction product of the present invention includes any one or more of the above referenced embodiments of the third aspect of the present invention wherein the bioactive compound is a peptide, a carbohydrate or a growth factor. In one or more embodiments, the reaction product of the present invention includes any one or more of the above referenced embodiments of the third aspect of the present invention wherein the bioactive compound is selected from the group consisting of Lys (biotin), bone morphogenic protein-2 (BMP-2), bone morphogenic protein-7 (BMP-7), osteogenic growth peptide (OGP), the c-terminal fragment of OGP [10-14] (YGFGG), GRGDS (RGD), and combinations thereof.

In a fourth aspect, the present invention provides an novel amino acid-based monomer for use in forming an amino acid-based poly(ester ureas) functionalized to bond with a bioactive compounds, having the formula:

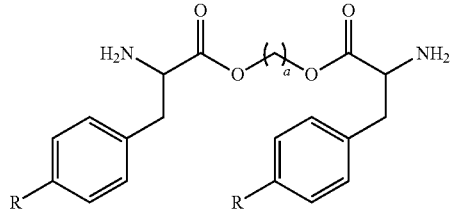

(XI)

wherein R is a pendent functional group and a is an integer from 2 to 12. In some embodiments, present invention is directed to the novel amino acid-based monomer of the fourth aspect of the present invention wherein R comprises an oxygen atom connected to a alkyl or aryl group containing a moiety capable of forming a chemical bond through a click reaction In one or more embodiments, the novel amino acid-based monomer of the present invention includes any one or more of the above referenced embodiments of the fourth aspect of the present invention wherein R comprises an oxygen atom connected to a alkyl or aryl group containing an alkyne group, an alkene group, an azide group, a benzyl protected phenol group, a or ketone group. In one or more embodiments, the novel amino acid-based monomer of the present invention includes any one or more of the above referenced embodiments of the fourth aspect of the present invention wherein R is OH, OCH$_2$C≡CH, OCH$_2$CH$_2$CH$_2$N$_3$, OCH$_2$CH$_2$CH=CH$_2$, OCH$_2$Ph, or OCOCH$_2$CH$_2$COCH$_3$.

In one or more embodiments, the novel amino acid-based monomer of the present invention includes any one or more of the above referenced embodiments of the fourth aspect of the present invention having a formula selected from the group consisting of:

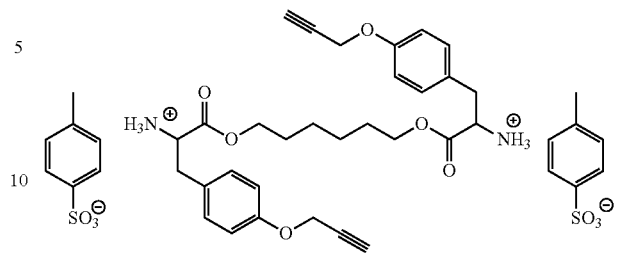

(XII)

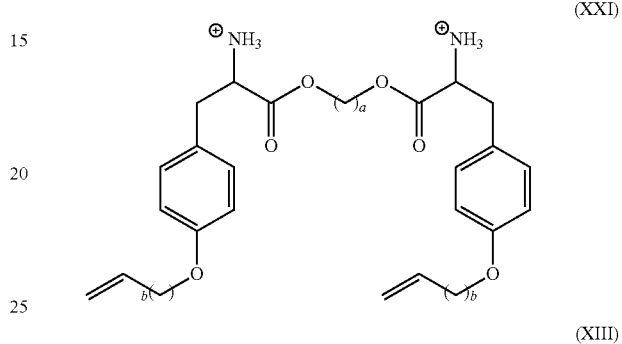

(XXI)

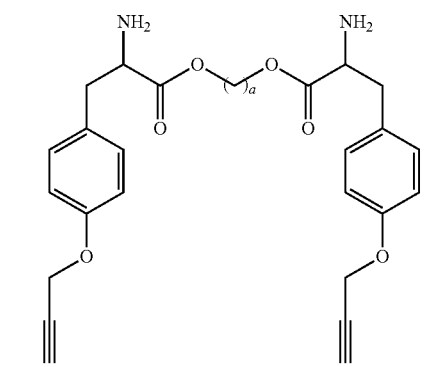

(XIII)

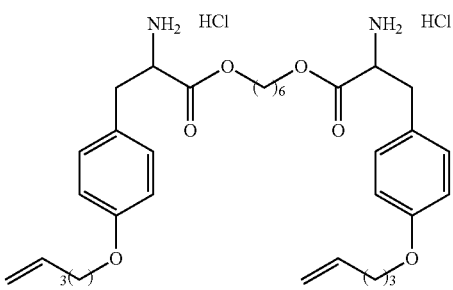

(XXII)

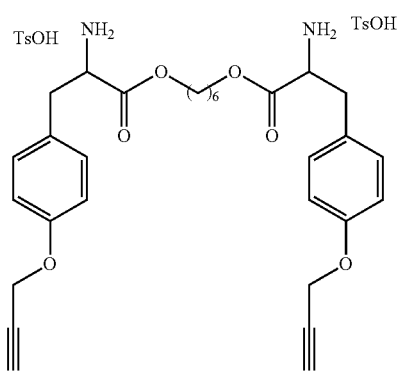

(XIV) (M2)

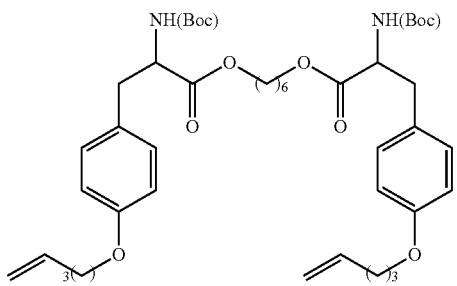
(XXIII)
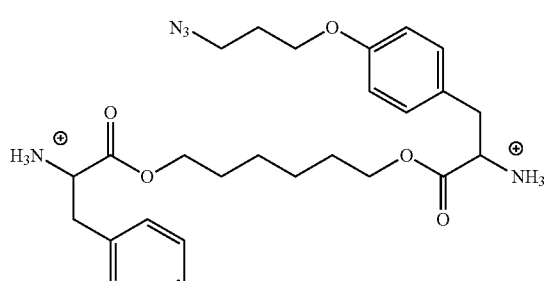
(XV) (M3)
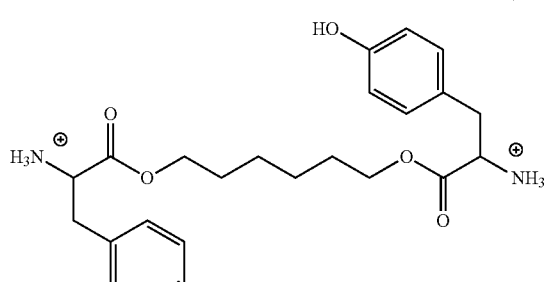
(XXIV)
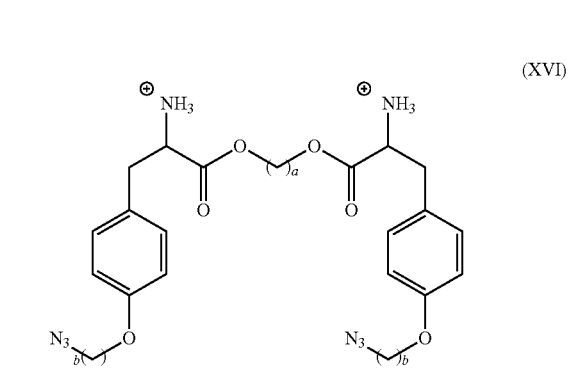
(XVI)
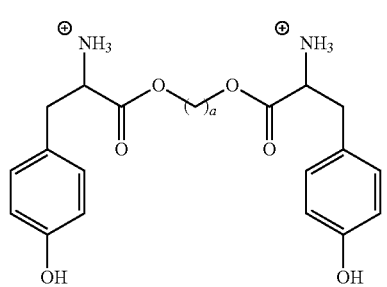
(XXV)
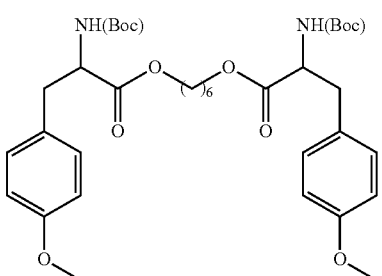
(XVII)
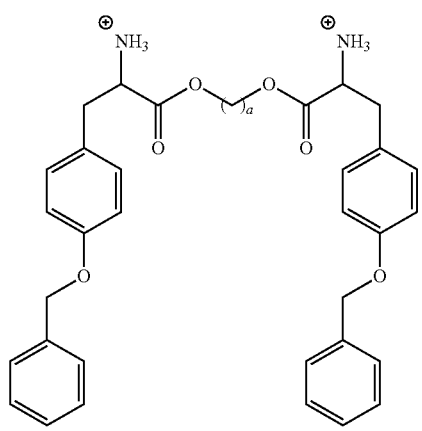
(XXVI)
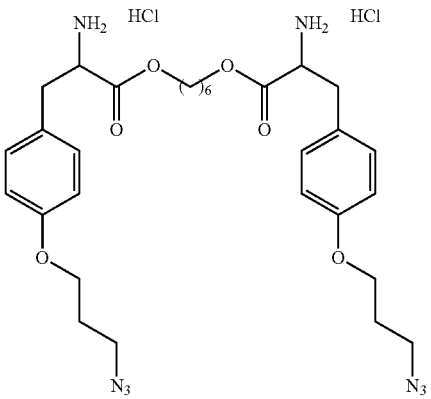
(XVIII) (M3)
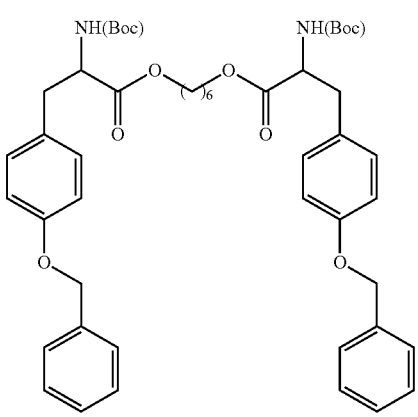
(XXVII)

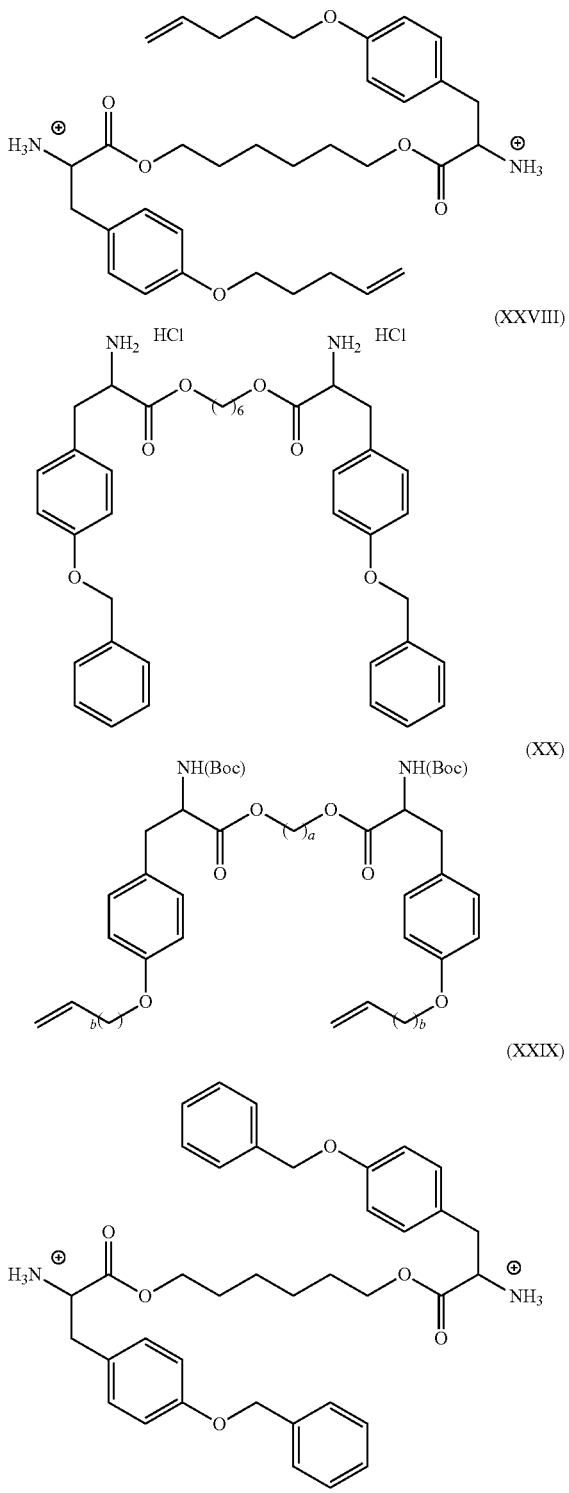

wherein a is an integer from 2 to 12; and b is an integer from 1 to 8.

In a fifth aspect, the present invention provides an method for making an amino acid-based poly(ester urea) functionalized to bond with a bioactive compound comprising: dissolving a phenylalanine-based monomer, a tyrosine-based monomer having one or more pendent functional groups, and a base selected from the group consisting of sodium carbonate, or potassium carbonate and combinations thereof in an aqueous solution; reducing the temperature of the solution to a temperature of from about −5° C. to about 5° C.; adding a solution comprising triphosgene or phosgene and a suitable organic solvent to the solution forming an interfacial mixture having an organic phase and an aqueous phase; separating the organic and aqueous phases of the interfacial mixture and collecting and purifying the organic phase to produce the amino acid-based poly(ester urea) functionalized to bond with a bioactive compound.

In some embodiments, present invention is directed to the method of the fifth aspect of the present invention further comprising: washing the organic phase in water; adding the washed organic phase to an excess of hot water, causing the amino acid-based poly(ester urea) functionalized to bond with a bioactive compound to precipitate into the hot water; and recovering the precipitated amino acid-based poly(ester urea) polymer functionalized to bond with a bioactive compound by filtration.

In one or more embodiments, the method of the present invention includes any one or more of the above referenced embodiments of the fifth aspect of the present invention wherein the phenylalanine-based monomer has the formula:

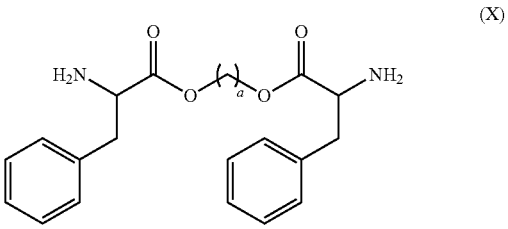

wherein a is an integer from 2 to 12. In one or more embodiments, the method of the present invention includes any one or more of the above referenced embodiments of the fifth aspect of the present invention wherein the tyrosine-based monomer having one or more pendent functional groups has the formula:

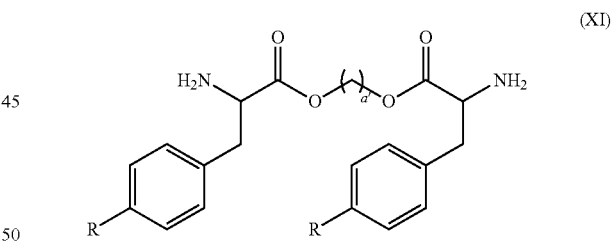

wherein R is pendant functional group; and a is an integer from 2 to 12.

In one or more embodiments, the method of the present invention includes any one or more of the above referenced embodiments of the fifth aspect of the present invention wherein R is an oxygen atom connected to a alkyl or aryl group containing an alkyne group, an alkene group, an azide group, a benzyl protected phenol group, a or ketone group. In one or more embodiments, the method of the present invention includes any one or more of the above referenced embodiments of the fifth aspect of the present invention wherein R is OH, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

In one or more embodiments, the method of the present invention includes any one or more of the above referenced embodiments of the fifth aspect of the present invention wherein the one or more pendent functional groups comprises a benzyl protected phenol, the method further comprising: preparing an amino acid-based poly(ester urea) functionalized to bond with a bioactive compound as set forth above, wherein one or more pendent functional groups comprises a benzyl protected phenol; collecting, purifying and drying the amino acid-based poly(ester urea) functionalized to bond with a bioactive compound; dissolving the amino acid-based poly(ester urea) in a suitable organic solvent and adding a catalytic amount of palladium on carbon to form a suspension; stirring the resulting suspension under a hydrogen atmosphere at a temperature of from about 45° C. to about 55° C., for from 1 hour to about 24 hours, at a pressure of from 50 to about 70 psi; filtering the suspension through a Celite column; collecting and concentrating the filtrate; and adding the filtrate to an excess volume of water to precipitate out a functionalized amino acid-based poly(ester urea) having the formula:

wherein a and a' are integers from 2 to 12 and x is a mole percentage of from 0.001 to 0.200.

In one or more embodiments, the method of the present invention includes any one or more of the above referenced embodiments of the fifth aspect of the present invention wherein the suitable base is selected from the group consisting of 4-(N,N-dimethylamino) pyridinium-4-toluenesulfonate (DPTS). In one or more embodiments, the method of the present invention includes any one or more of the above referenced embodiments of the fifth aspect of the present invention further comprising: collecting, purifying and drying the amino acid-based poly(ester urea) functionalized to bond with a bioactive compound.

In a sixth aspect, the present invention provides a method for making an formed polymer structure, coating or film functionalized to bond with a bioactive compound comprising: preparing an amino acid based poly(ester urea) polymer

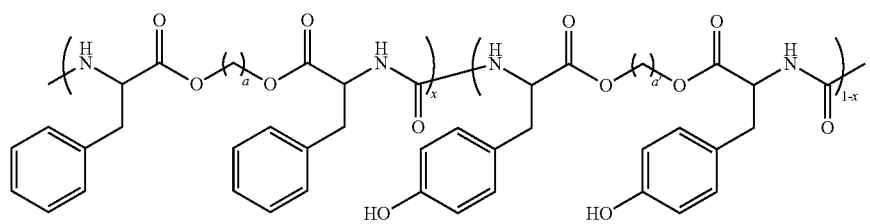

(VIII)

wherein a and a' are each an integer from 2 to 12; and x is a mole fraction of from 0.001 to 0.200. In one or more embodiments, the method of the present invention includes any one or more of the above referenced embodiments of the fifth aspect of the present invention further comprising collecting, purifying, and drying the amino acid-based poly (ester urea).

In one or more embodiments, the method of the present invention includes any one or more of the above referenced embodiments of the fifth aspect of the present invention further comprising: dissolving the amino acid-based poly (ester urea) in a suitable organic solvent; adding stoicheometrically appropriate quantities of levulinic acid and suitable base; cooling the solution to a temperature of from about −5° C. to about 5° C. and adding a stoicheometrically appropriate quantity of 1,3-diisopropyl cabodiimide (DIPC); allowing the solution to warm up to room temperature and stirring for from about 2 hours to about 24 hours; and adding the mixture to an excess volume of methanol or ethanol to produce an amino acid-based poly(ester urea) having the formula:

comprising: at least one phenylalanine-based monomer segment and at least one tyrosine-based monomer segment, wherein the at least one tyrosine-based monomer segment has one or more pendent functional groups selected to bond to a corresponding functional group on a bioactive compound; and forming the amino acid based poly(ester urea) polymer into a desired structure.

In some embodiments, present invention is directed to the method of the sixth aspect of the present invention wherein the desired structure is selected from the group consisting of fibers, films, a tissue scaffolds, tubes, screws, pins, coatings, medical devices, and combinations thereof. In one or more embodiments, the method of the present invention includes any one or more of the above referenced embodiments of the sixth aspect of the present invention wherein the desired structure is a fiber formed by electrospinning, melt blowing, nanofibers by gas jet, solution casting, spinning coating, three-dimensional printing, injection molding, extrusion, or blow molding.

In a seventh aspect, the present invention provides a method for attaching bioactive compounds to a pre-fabri-

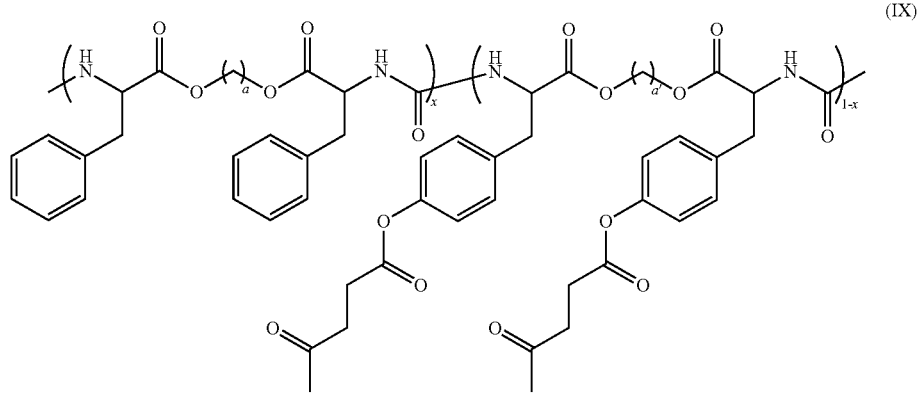

(IX)

cated amino acid-based poly(ester urea) structure, coating, or film functionalized to bond thereto comprising: selecting a bioactive compound to be attached to a pre-fabricated amino acid-based poly(ester urea) structure, coating, or film; adding a functional group to the bioactive compound, wherein the functional group will form a chemical bond using a click reaction; preparing an amino acid-based poly(ester urea) polymer structure, coating, or film comprising an amino acid based poly(ester urea) polymer having at least one phenylalanine-based monomer segment and at least one tyrosine-based monomer segment, wherein the at least one tyrosine-based monomer segment has one or more pendent functional groups capable of bonding to the functional group on the bioactive compound using a click reaction; and reacting the functional groups on the bioactive compound with the functional groups on the amino acid-based poly(ester urea) structure, coating, or film using a click reaction, thereby forming bonds between the bioactive compound and the amino acid-based poly(ester urea) polymer structure, coating, or film and attaching the bioactive compound to the amino acid-based poly(ester urea) polymer structure, coating, or film.

In some embodiments, present invention is directed to the method of the seventh aspect of the present invention wherein the amino acid-based poly(ester urea) polymer structure, coating, or film is a fiber, film, tissue scaffold, tube, pin, screw coating, or medical device. In one or more embodiments, the method of the present invention includes any one or more of the above referenced embodiments of the seventh aspect of the present invention wherein the amino acid-based poly(ester urea) polymer structure, coating or film is a microfiber or nanofiber.

In one or more embodiments, the method of the present invention includes any one or more of the above referenced embodiments of the seventh aspect of the present invention wherein the bioactive compound is a peptide, a carbohydrate, or a growth factor. In one or more embodiments, the method of the present invention includes any one or more of the above referenced embodiments of the seventh aspect of the present invention wherein the bioactive compound is selected from the group consisting of a peptide, a carbohydrate, a growth factor, and combinations thereof. In one or more embodiments, the method of the present invention includes any one or more of the above referenced embodiments of the seventh aspect of the present invention wherein the functional group on the bioactive compound is selected from the group comprising Lys(biotin), bone morphogenic protein-2 (BMP-2), bone morphogenic protein-7 (BMP-7), osteogenic growth peptide (OGP), the c-terminal fragment of OGP [10-14] (YGFGG), GRGDS (RGD), and combinations thereof.

In one or more embodiments, the method of the present invention includes any one or more of the above referenced embodiments of the seventh aspect of the present invention wherein the one or more pendent functional groups on the at least one tyrosine-based monomer segment of the amino acid-based poly(ester urea) polymer structure comprises a functional group selected from the group consisting of: alkyne groups, alkene groups, azide groups, benzyl protected phenol groups, ketone groups, and combinations thereof. In one or more embodiments, the method of the present invention includes any one or more of the above referenced embodiments of the seventh aspect of the present invention wherein the click reaction is a reaction selected from the group consisting of Huisgen cycloaddition reactions, copper (I) catalyzed azide-alkyne cycloaddition (CuAAC) reactions, thiol-ene radical addition reactions, oxime ligation reactions, Michael-addition reactions, Mannich-type addition reactions, "ene-type" addition reactions, strain promoted azide-alkyne cycloaddition (SPAAC) reactions, Diels-Alder reactions, and combinations thereof.

In an eighth aspect, the present invention provides a method for making a novel amino acid-based monomer for forming an amino acid-based poly(ester ureas) functionalized to bond with a bioactive compound comprising: dissolving functionalized tyrosine precursor group in a suitable solvent; reacting the hydroxyl of the functionalized tyrosine precursor group with a functionalized alkyl halide or alkyl azide having a pendent functional group, thereby attaching the pendent functional group to the phenyl oxygen of the functionalized tyrosine precursor; determine whether the resulting product has a protected ester group and if it does, reacting the product of the step of adding the pendent functional group with a base to deprotect the ester group; reacting the resulting compound with a stoicheometrically appropriate quantity of a diol having from 2 to 12 carbon atoms to produce a functionalized tyrosine-based monomer; determining whether the resulting compound has a protected amine group; and if it does, dissolving the compound in HCl and dioxane under a nitrogen or argon atmosphere to deprotect the amine group and produce a novel amino acid-based monomer for use in forming an amino acid-based poly(ester ureas) functionalized to bond with bioactive compounds.

In some embodiments, present invention is directed to the method of the eighth aspect of the present invention wherein the pendent functional group further comprises a clickable alkyne group and the step of adding the pendent functional group is performed by reacting functionalized alkyl halide having a pendent functional group containing a clickable alkyne group with the functionalized tyrosine precursor, thereby attaching the pendent functional group to the phenyl oxygen of the functionalized tyrosine precursor.

In one or more embodiments, the method of the present invention includes any one or more of the above referenced embodiments of the eighth aspect of the present invention wherein the functionalized alkyl halide is propargyl bromide.

In one or more embodiments, the method of the present invention includes any one or more of the above referenced embodiments of the eighth aspect of the present invention wherein the pendent functional group further comprises a clickable azide group and the step of adding the pendent functional group is performed by reacting a functionalized alkyl azide having a pendent functional group containing a clickable azide group with the functionalized tyrosine precursor, thereby attaching the pendent functional group to the phenyl oxygen of the functionalized tyrosine precursor.

In one or more embodiments, the method of the present invention includes any one or more of the above referenced embodiments of the eighth aspect of the present invention wherein the pendent functional group further comprises a clickable alkene group and the step of adding the pendent functional group is performed by reacting a functionalized alkyl halide having a pendent functional group containing a clickable alkene group with the functionalized tyrosine precursor, thereby attaching the pendent functional group to the phenyl oxygen of the functionalized tyrosine precursor.

In one or more embodiments, the method of the present invention includes any one or more of the above referenced embodiments of the eighth aspect of the present invention further comprising removing the organic solvent from the compound by lyophilization and then washing the compound in diethyl ether and drying it in a vacuum.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1A:
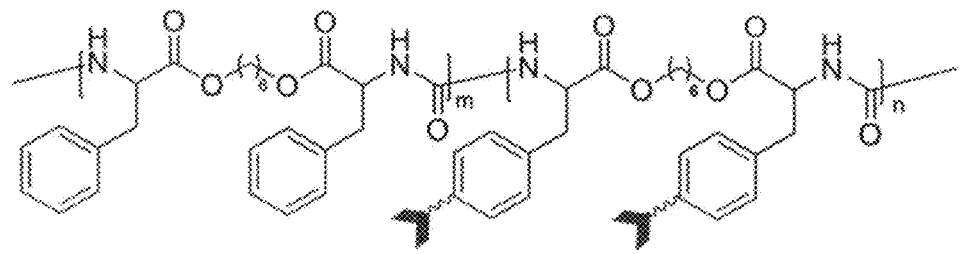
FIG. 1A-B are a schematic depicting (A) a PEU according to one or more embodiments of the present invention showing the pendent functional groups and (B) bio-orthogonal conjugation of fluorescence labeled biomolecules with corresponding "clickable" functional groups.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In general outline, embodiments of the present invention relate to novel amino acid based PEUs functionalized to bond with bioactive molecules via a click reaction after the PEU has been processed into its intended form and/or composition and related methods of attaching bioactive molecules to novel amino acid based PEUs using "click" reactions. As used herein, the terms "click reaction," "click chemistry," "click chemistry methods," "click chemistry reactions," are used interchangeably to refer to a group of orthogonal conjugation reactions, generally referred to in the art as "click" reactions, that fulfill the following prerequisites: (i) high yield, nearly quantitative conversion; (ii) biologically benign conditions (aqueous solution, ambient temperature, and near physiologic pH); (iii) limited or no residual byproduct. These reactions are typically simple to perform, high yielding, stereospecific, wide in scope, create only byproducts that can be removed without chromatography, and can be conducted in easily removable or benign solvents. Similarly, the term "clickable" refers to a molecule or functional group capable of bonding via a click reaction.

The "click" chemistry concept currently represents a number of orthogonal reactions, which are robust, selective, efficient, and high yielding, including, without limitation, copper (I) catalyzed azide-alkyne cycloaddition (CuAAC) reactions (a.k.a. Huisgen cycloaddition reactions), thiol-ene radical addition reactions, oxime ligation reactions, Michael-addition reactions, thiol-Michael-addition reactions, Mannich-type addition reactions, "ene-type" addition reactions, thiol-ene radical addition, strain promoted azide-alkyne cycloaddition (SPAAC) reactions, non-traceless Staudinger ligation, traceless Staudinger ligation, Diels- Alder reactions, hetero Diels-Alder reactions, inverse electron demand Diels-Alder reactions, tandem [3+2] cycloaddition-retro-Diels-Alder (tandem crD-A) reactions, thiol-alkyne reactions, thiol-pyridyl disulfide reactions, thiol-halogen ligation, native chemical ligation, and thiazolidine ligation reactions.

As used herein, the terms "bioactive molecule(s)" and "bioactive material(s) are used interchangeably to refer to substances that influence cellular function. Bioactive molecules may include, without limitation, peptides, carbohydrates, proteins, oligonucleotides and small molecule drugs.

In a first aspect, embodiments of the present invention relate to novel tyrosine based monomers for forming amino acid based poly(ester ureas) functionalized to bond with a bioactive compound via one of a series of click reactions. In some embodiments, these monomers have the following structure:

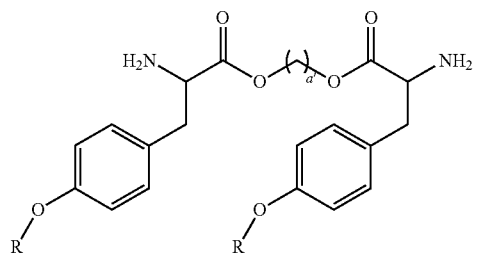

(XXX)

wherein R is a pendent functional group capable of binding to a functionalized bioactive molecule via a click reaction and a is an integer from 2 to 12. In some embodiments, a may be an integer from 4 to 10. In some embodiments, a may be an integer from 6 to 8. In some embodiments, a may be 6.

Further, it should be appreciated that the amine groups in compound (XXX) may be protected by a tosylic acid salt, but the present invention is not to be so limited. These amine groups may be protected by any method known in the art for that purpose. In some embodiments, HCl, HBr and HI salts may be used to protect the amine groups on monomers according to the present invention. In some embodiments, para-toluene sulphonic acid (TosOH) may be used to protect the amine groups on monomers according to the present invention.

The pendent functional groups (R) that may be used are not particularly limited, provided that they are capable of a click reaction and can be attached to the hydroxyl (phenol) group of the tyrosine portion of the monomer. Suitable pendent functional groups (R) may include, without limitation, a linear or branched alkyl and/or aryl group comprising a moiety capable of bonding by means of a click reaction. Suitable moieties include, without limitation, alkyne groups, alkene groups, azide groups, ketones or strained cyclooctynes. In some embodiments, the pendent functional groups may be —CH$_2$C≡CH, —CH$_2$CH$_2$CH$_2$N$_3$, —CH$_2$CH$_2$CH$_2$CH═CH$_2$, —CH$_2$Ph, or —COCH$_2$CH$_2$COCH$_3$.

In some embodiments, the novel tyrosine based monomers of the present invention may have one of the following formulas:

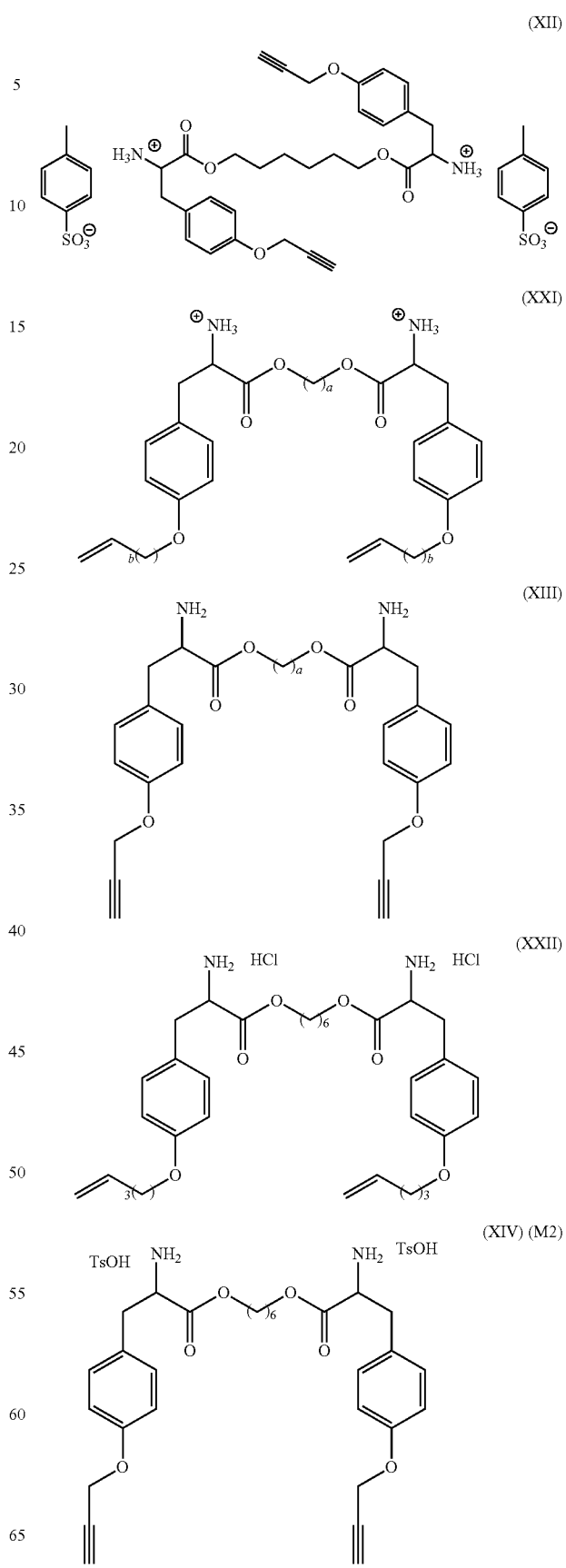

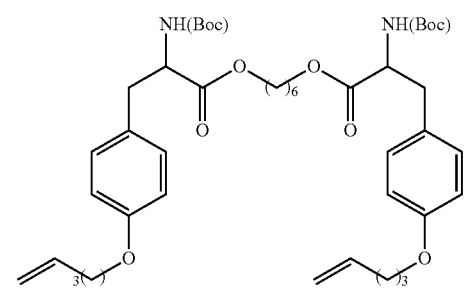
(XXIII)
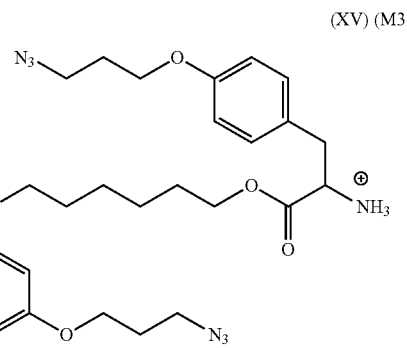
(XV) (M3)
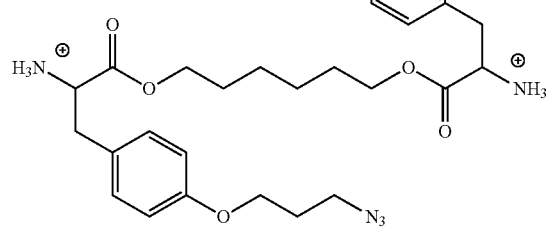
(XXIV)
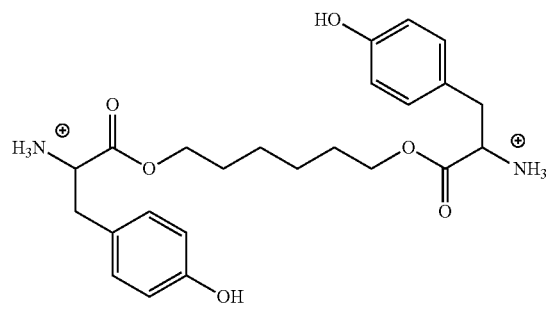
(XVI)
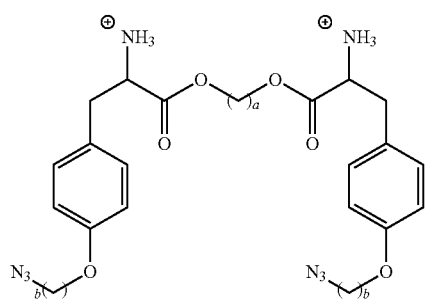
(XXV)
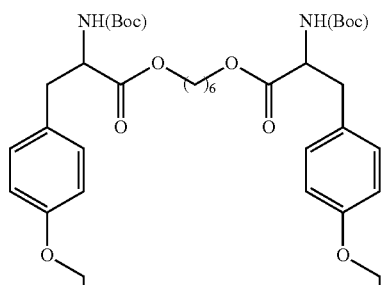
(XVII)
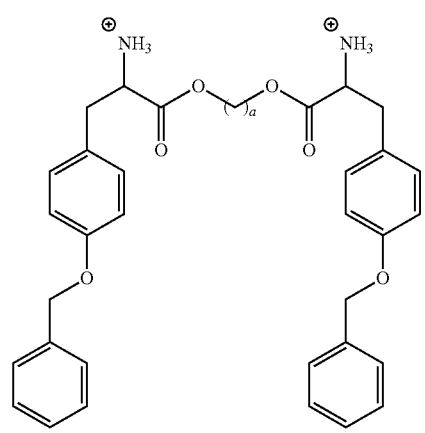
(XXVI)
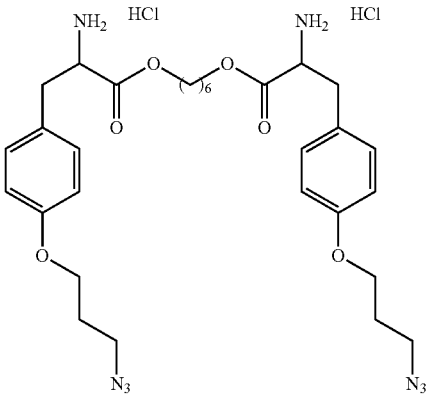
(XVIII) (M3)
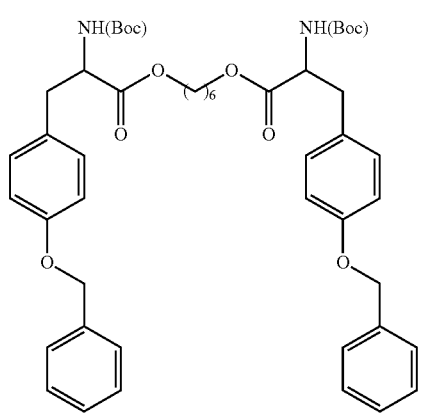
(XXVII)

-continued

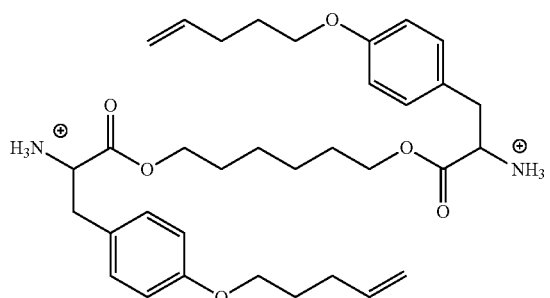
(XIX) (M4)

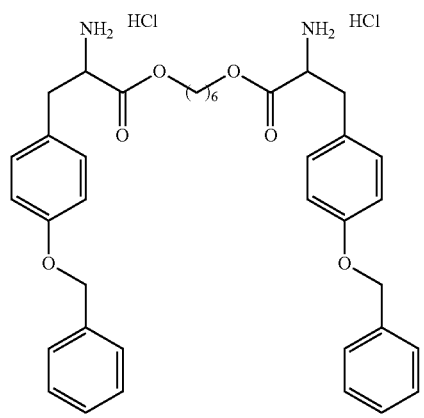
(XXVIII)

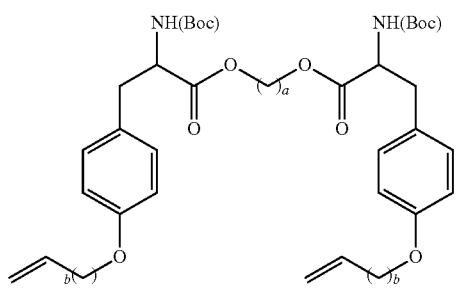
(XX)

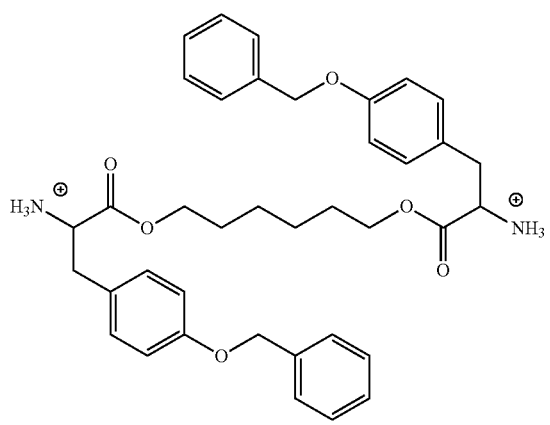
(XXIX)

wherein a is an integer from 2 to 12; and b is an integer from 1 to 8.

It should be appreciated, however, that in certain embodiments the novel tyrosine based monomers of the present invention may also include one or more pendent functional groups (R) that can readily be converted to include a moiety capable of bonding by means of a click reaction (a "clickable" moiety) as described above. In some embodiments, the pendent functional groups (R) may be "protected" in any of a number of ways known in the art and must be "deprotected" before being used. In some embodiments, for example, the pendent functional groups (R) is a benzyl protected phenol group. In these embodiments, the benzyl protected phenol group must first be deprotected by removing the protecting benzyl group and adding a proton to form the phenol group (R=H) before the clickable ketone group may be added.

In some embodiments, the novel tyrosine based monomers of the present invention may have one of the following formulas:

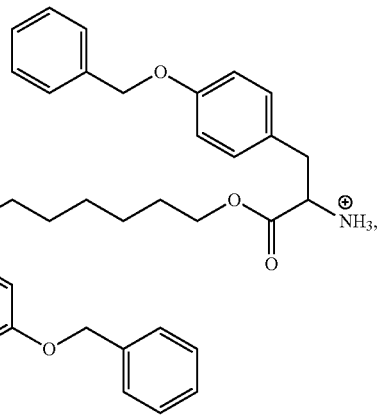
(XXIX)

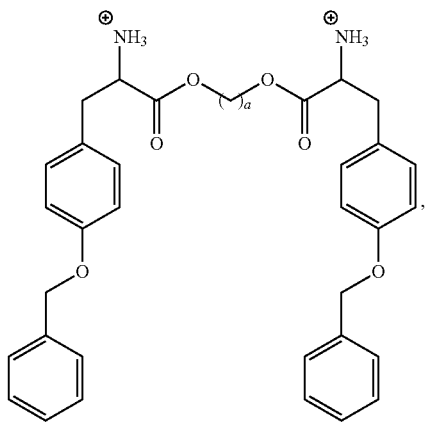
(XXVI)

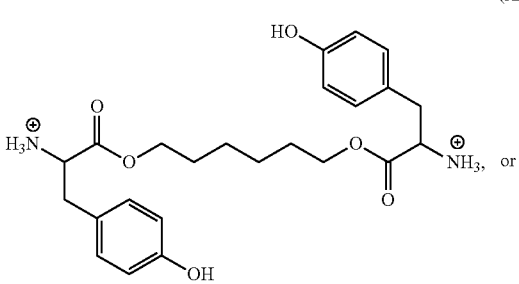
(XXIV)

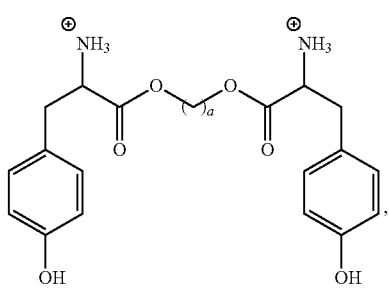

(XXII)

wherein a is an integer from 2 to 12.

In another aspect, embodiments of the present invention relate to amino acid based poly(ester ureas) made from the novel tyrosine based monomers described above. It has been found that the random copolymerization of these functionalized tyrosine-based monomers and a similar phenylalanine-based monomer yield novel poly(ester ureas) with "clickable" pendent functional groups.

In some embodiments, these amino acid based poly(ester urea) polymers comprise a phenylalanine-based monomer segment and a tyrosine-based monomer segment with one or more pendent functional groups that will bond with a suitably functionalized bioactive compound via a click reaction. In some embodiments, phenylalanine-based monomer segments have the formula:

(I)

wherein a is an integer from 2 to 12. In some embodiments, a may be an integer from 4 to 10. In some embodiments, a may be an integer from 6 to 8. In some embodiments, a may be 6.

The amino acid based poly(ester urea) polymers according to embodiments of the present invention further include a tyrosine-based monomer segment having a pendent functional group capable of bonding by means of a click reaction. The pendent functional groups that may be used are not particularly limited, provided that they are capable of bonding by means of a click reaction and can be attached to the hydroxyl group of the tyrosine portion of the polymer. Suitable pendent functional groups may include, without limitation, an oxygen atom bound to a linear or branched alkyl and/or aryl group comprising a moiety capable of bonding by means of a click reaction. Suitable "clickable" moieties include, without limitation, alkyne groups, alkene groups, azide groups, ketones or strained cyclooctyne groups.

In some embodiments, the tyrosine-based monomer segment may have the formula:

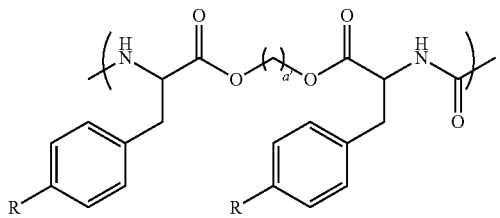

(II)

wherein R (the pendant functional group) is an oxygen atom connected to an alkyl and/or aryl group containing a functional group capable of forming a chemical bond through a click reaction, as set forth above and a' is an integer from 2 to 12. In some embodiments, R may be an oxygen atom connected to a [n] linear alkyl or aryl group comprising an alkyne group, an alkene group, an azide group, a ketone or a strained cyclooctyne group. In some embodiments of segment II, R may be —OCH$_2$C≡CH, —OCH$_2$CH$_2$CH$_2$N$_3$, or —OCH$_2$CH$_2$CH$_2$CH═CH$_2$. In some embodiments, a' may be an integer from 4 to 10. In some embodiments, a' may be an integer from 6 to 8. In some embodiments, a' may be 6.

As with the monomers described above, it should be appreciated that in certain embodiments the novel tyrosine based monomers segments of the amino acid based poly (ester urea) polymers of the present invention may also include one or more pendent functional groups (R) that can readily be converted to include a clickable moiety as described above. In some embodiments of segment II, R may be a hydroxyl group or a benzyl protected phenol group. In some embodiments, R may be OH or OCH$_2$Ph.

In some embodiments, these novel poly(ester ureas) may have the general formula:

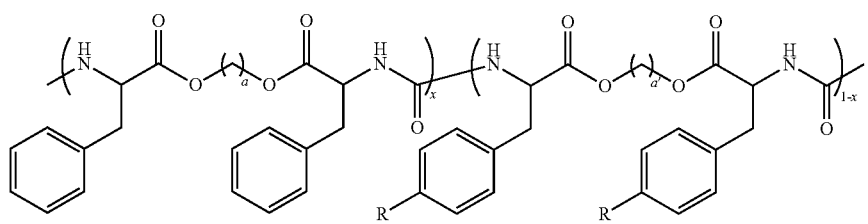

(III)

wherein R is a pendent functional group capable of binding to a functionalized bioactive molecule via a click reaction; x is a mole fraction of from 0.001 to 0.990; and a and a' are integers from 2 to 12. (See FIG. 1A). In some embodiments, R may be an oxygen atom connected to a[n] linear alkyl and/or aryl group comprising an alkyne group, an alkene group, an azide group, a benzyl protected phenol group, a ketone or a strained cyclooctyne group. In some embodiments of compound III, R may be OCH₂C≡CH, OCH₂CH₂CH₂N₃, OCH₂CH₂CH₂CH=CH₂, or OCOCH₂CH₂COCH₃. And as set forth above, the amino acid based poly(ester urea) polymers of the present invention may also include one or more pendent functional groups (R) that can readily be converted to include a clickable moiety as described above. In some embodiments of compound III, R may be a hydroxyl group or a benzyl protected phenol group. In some embodiments, R may be OH or OCH₂Ph.

In some embodiments, a and a' may each be an integer from 4 to 10. In some embodiments, a and a' may each be an integer from 6 to 8. In some embodiments, a and a' may each be 6. In some embodiments, x may be a mole fraction of from 1 to 10 percent. In some embodiments, x may be a mole fraction of from 10 to 50 percent. In some embodiments, x may be a mole fraction of 5 percent.

As set forth above, the pendent functional groups of the novel PEU's of embodiments of the present invention are functionalized to bond with a corresponding moiety on a bioactive compound using a click reaction. Suitable click reactions may include, without limitation, copper (I) catalyzed azide-alkyne cycloaddition (CuAAC)(Huisgen cycloaddition reactions), thiol-ene radical addition reactions, oxime ligation reactions, Michael-addition reactions, thiol-Michael-addition reactions, Mannich-type addition reactions, "ene-type" addition reactions, thiol-ene radical addition, strain promoted azide-alkyne cycloaddition (SPAAC) reactions, non-traceless Staudinger ligation, traceless Staudinger ligation, Diels-Alder reactions, hetero Diels-Alder reactions, inverse electron demand Diels-Alder reactions, tandem [3+2] cycloaddition-retro-Diels-Alder (tandem crD-A) reactions, thiol-alkyne reactions, thiol-pyridyl disulfide reactions, thiol-halogen ligation, native chemical ligation, thiazolidine ligation reactions, and/or various combinations thereof. It should be appreciated, however, that selection of an appropriate pendent functional group for the novel PEU's of the present invention will depend upon the presence of, and/or the ability to conveniently add, a corresponding clickable moiety on the bioactive compound.

As will be appreciated by those of skill in the art, x and 1-x represent the mole fractions of the phenylalanine-based monomer segments (x) and the functionalized tyrosine-based monomer segments (1-x) in the polymer. In some embodiments, x may be from 0.001 to 0.990. In some embodiments, x may be from 0.500 to 0.990. In some embodiments, x may be from 0.900 to 0.990.

It should be appreciated that x may also be expressed as a mole percent. In some embodiments, the phenylalanine-based monomer segments make up from 1 to 99 mole percent of the polymer. In some embodiments, the phenylalanine-based monomer segments make up from 10 to 90 mole percent of the polymer. In some embodiments, the phenylalanine-based monomer segments make up from 50 to 99 mole percent of the polymer. In some embodiments, the phenylalanine-based monomer segments make up from 90 to 99 mole percent of the polymer. In some embodiments, the functionalized tyrosine-based monomer segments make up from 1 to 99 mole percent of the polymer. In some embodiments, the functionalized tyrosine-based monomer segments make up from 1 to 50 mole percent of the polymer. In some embodiments, the functionalized tyrosine-based monomer segments make up from 1 to 10 mole percent of the polymer.

In some embodiments, the weight average molecular mass ($M_w$) of the novel PEUs of the present invention is from about 3,000 to about 300,000. In some embodiments, the weight average molecular mass ($M_w$) of the novel amino acid based poly(ester ureas) of the present invention is from about 3,000 to about 100,000. In some embodiments, the weight average molecular mass ($M_w$) of the novel amino acid based poly(ester ureas) of the present invention is from about 3,000 to about 50,000. In some embodiments, the weight average molecular mass ($M_w$) near of the novel amino acid based poly(ester ureas) of the present invention is approximately 100 k Da.

In some embodiments, the distribution of molecular mass ($D_m=M_w/M_n$) of the novel PEUs of the present invention is from about 1.3 to about 3.5. In some embodiments, $D_m$ of the novel PEUs of the present invention is from about 1.5 to about 3.0. In some embodiments, $D_m$ of the novel PEUs of the present invention is from about 1.3 to about 2.5. In some embodiments, $D_m$ of the novel PEUs of the present invention is from about 1.3 to about 2.0. In some embodiments, $D_m$ of the novel PEUs of the present invention is from about 1.3 to about 1.6.

In some embodiments, the thermal decomposition temperature ($T_d$) of the novel PEUs of the present invention is from about 274° C. to about 277° C.

In some embodiments, the novel amino acid based poly (ester ureas) of the present invention have one of the following formulas:

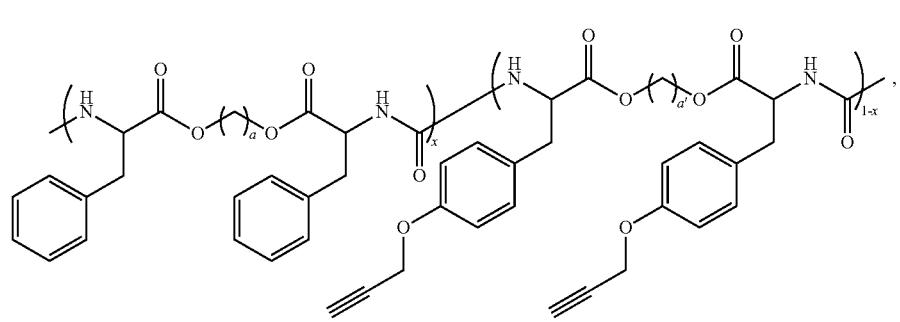

(IV) (PEU-2)

-continued
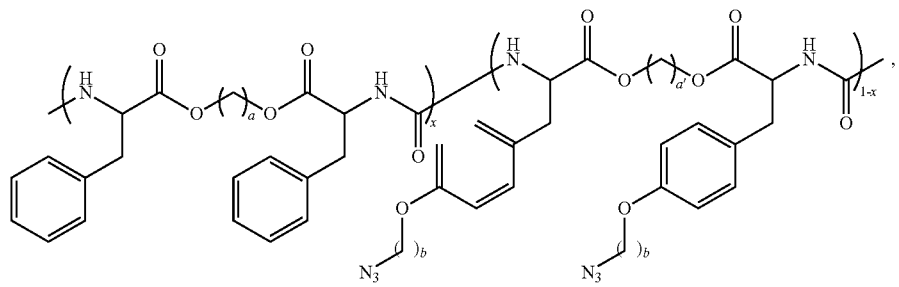
(V) (PEU-2)
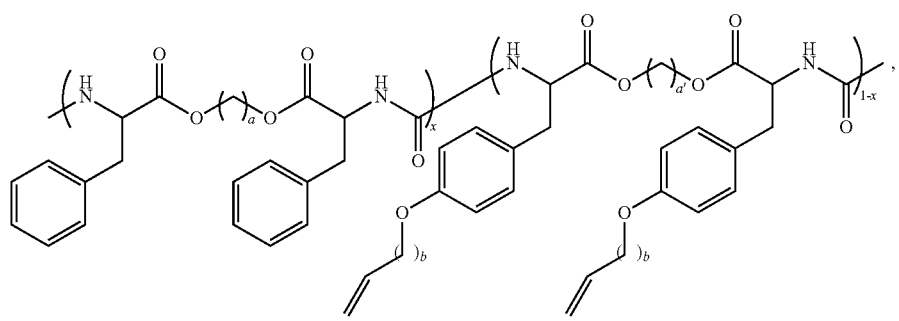
(VI) (PEU-4)
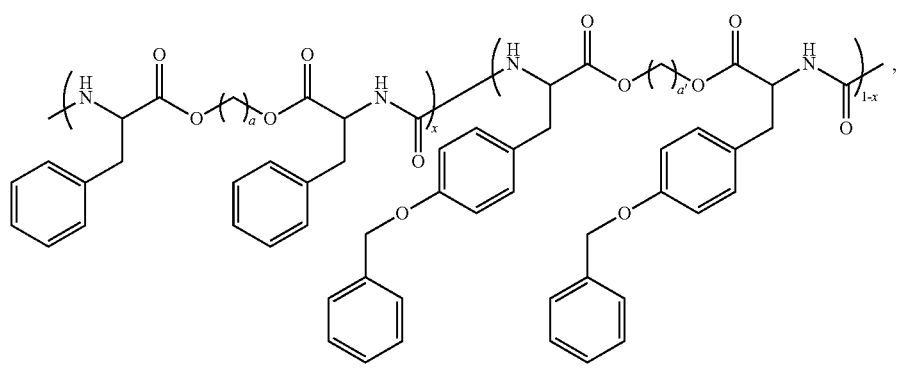
(VII) (PEU-5)
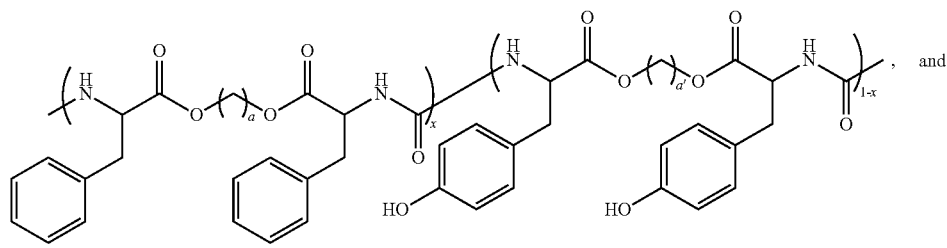
(VIII) (PEU-6), and
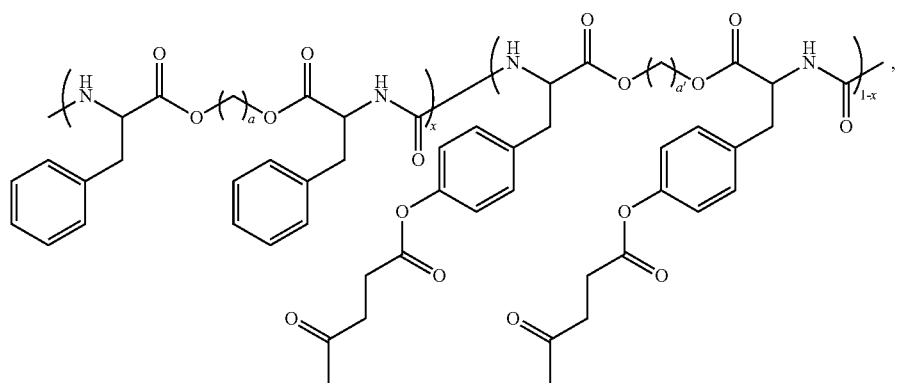
(IX) (PEU-7)

wherein a and a' are integers from 2 to 12; b is an integer from 1 to 8; x is a mole percentage of from 1 to 99%. In some embodiments, a and a' may each be an integer from 4 to 10. In some embodiments, a and a' may each be an integer from 6 to 8. In some embodiments, a and a' may be 6. In some embodiments, b may each be an integer from 2 to 8. In some embodiments, b may each be an integer from 2 to 6. In some embodiments, b may each be 3. In some embodiments, x may be a mole percentage of from 1 to 99. In some embodiments, x may be a mole percentage of from 1 to 10. In some embodiments, x may be a mole percentage of 2.

In another aspect, embodiments of the present invention relate to the PEU's described above wherein the pendant functional groups have been bonded to a bioactive molecule using a click reaction. As set forth above, bioactive molecules are substances that influence cellular function and may include, without limitation, peptides, carbohydrates, oligonucleotides. In some embodiments, the bioactive molecule may be a peptide. In some embodiments, the bioactive molecule may be bone morphogenic protein-2 (BMP-2), bone morphogenic protein-7 (BMP-7), osteogenic growth peptide (OGP), or the c-terminal fragment of OGP [10-14] (YGFGG), GRGDS (RGD). In some embodiments, the bioactive molecule may be Lys(biotin). In some embodiments, the bioactive molecule may be RGD.

In some embodiments, the amino acid based poly(ester ureas) according to embodiments of the present invention have the formula:

In another aspect, embodiments of the present invention relate to polymer structures, fibers, coatings, films, or other objects made from or containing the amino acid based PEU's described above, again functionalized to bond with a bioactive compound via any one of a series of "click" reactions. While the bioactive molecules may, in some embodiments, be attached to the acid based PEU's of the present invention prior to the polymer being shaped or formed for a particular application, it should be understood that there are applications in which it is advantageous to form the polymer into a final configuration and then attach the bioactive molecules thereto.

As those of skill in the art will appreciate, many peptides and other bioactive compounds are sensitive to a variety of environmental factors and could easily be damaged and/or denatured during the process of fabricating the desired structure, fiber, coating, film, medical device, or other objects to be used. Moreover, these objects may be fabricated ahead of time and/or in bulk for use with a variety of different bioactive molecules functionalized to bind to the polymer. In this way, the bioactive compound may be selected, functionalized, and attached just prior to use, reducing the chance of its being damaged or otherwise denatured before use.

In some embodiments, the novel amino acid based PEU's of the present invention may be formed into a wide variety of both 2-dimensional and 3-dimensional structures including, without limitation, tissue scaffolds, nanofibers, microfibers, coatings, and films. In most embodiments, the novel amino acid based PEU's of the present invention are stable (XXIX)

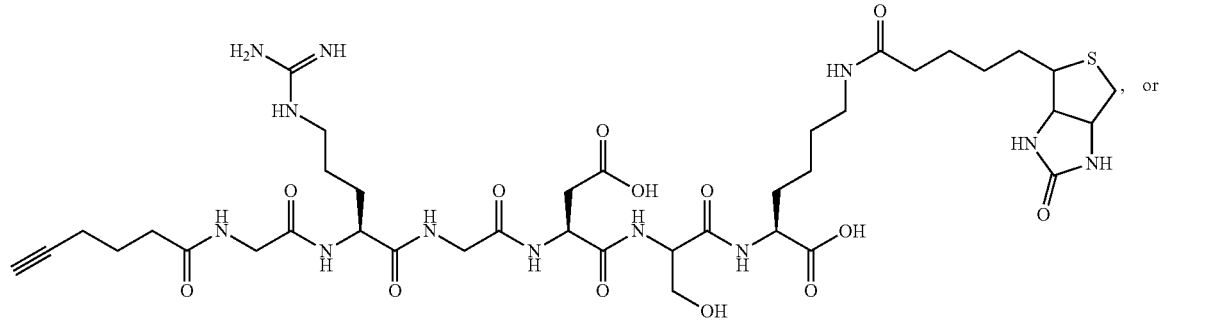

, or (XXX)

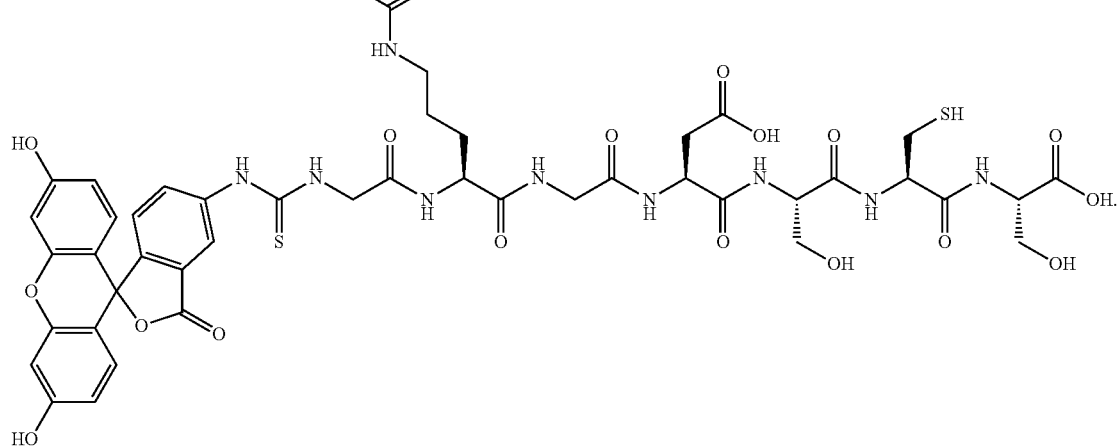

and may be formed using techniques such as blow molding, injection molding, extrusion, melt extrusion, 3-D printing, or electrospinning, provided that the polymer is not heated beyond its $T_d$. Moreover, most, if not all, of the novel amino acid based poly(ester ureas) of the present invention are soluble in polar organic solvents, including N,N-dimethylformamide (DMF), dimethyl sulfoxide (DMSO), N-methyl-2-pyrrolidone (NMP), and hexafluoroisopropanol (HFIP). The solubility properties provide access to a number of approaches for solution processing methods for PEU, including solution casting, spinning coating and electrospinning, dip coating, and spray drying, provided that the polymer is not heated beyond its $T_d$.

In some embodiments, the novel amino acid based PEU's of the present invention may be formed into a wide variety of both 2-dimensional and 3-dimensional structures by solution casting. Solution casting techniques are well known in the art and will be discussed here only to the degree necessary to understand the present invention. In some embodiments, films and coatings may be formed by solution casting PEUs of the present invention.

In some embodiments, the novel amino acid-based PEU's of the present invention may be formed into a wide variety of both 2-dimensional and 3-dimensional structures by melt extrusion. Melt extrusion techniques are well known in the art and will be discussed here only to the degree necessary to understand the present invention. In some embodiments, scaffolds, rods, pins, and screws may be formed by melt extrusion PEUs of the present invention.

In some embodiments, the novel amino acid based PEU's of the present invention may be formed into a wide variety of both 2-dimensional and 3-dimensional structures by melt spinning. Melt spinning techniques are well known in the art and will be discussed here only to the degree necessary to understand the present invention. In some embodiments, films, coatings, networks, meshes and foams may be formed by melt spinning PEUs of the present invention.

In some embodiments, the novel amino acid based PEU's of the present invention may be formed into a wide variety of both 2-dimensional and 3-dimensional structures by injection molding. Injection molding techniques are well known in the art and will be discussed here only to the degree necessary to understand the present invention. In some embodiments, scaffolds, rods, pins, and screws may be formed by injection molding PEUs of the present invention.

In some embodiments, the novel amino acid based PEU's of the present invention may be formed into a wide variety of both 2-dimensional and 3-dimensional structures by 3-D printing. 3-D printing techniques are well known in the art and will be discussed here only to the degree necessary to understand the present invention. In some embodiments, tissue scaffolds, may be formed by 3-D printing PEUs of the present invention.

In some embodiments, the novel amino acid based PEU's of the present invention may be formed into a film by solution casting or melt pressing. In some embodiments, the novel amino acid based PEU's of the present invention may be formed into a coating by solution casting or melt pressing. In some embodiments, the novel amino acid based PEU's of the present invention may be formed into a tissue scaffold by 3-d printing, salt leaching, electrospinning, melt spinning.

In some embodiments, the polymer may be formed into fibers by any of the numerous methods known in that art for that purpose. Suitable methods include, but are not limited to electrospinning, melt blowing, blow spinning, centrifugal spinning, rotary jet spinning and Nanofibers by Gas Jet (NGJ) (see e.g. U.S. Pat. Nos. 6,382,526, 6,520,425, and 6,695,992, which are incorporated herein by reference in their entirety), provided that the polymer is not heated beyond its $T_d$.

In some embodiments, the polymer may be formed into fibers of various sizes obtained via electrospinning of polymer solutions or from the melt. Methods for electrospinning polymers into fibers are well known in the art and will be discussed here only to the degree necessary to understand the present invention. One advantage of using electrospun fibers is that the physical and dimensional properties of fiber matrices can be tuned precisely. As those of skill in the art will appreciate, fiber diameter, alignment, surface-to-volume ratio, and porosity can be controlled in the electrospinning process using known methods. Moreover, polymeric nanofiber matrices are routinely used in biomedical applications, due to their morphological and structural similarities to the natural extra-cellular matrix (ECM). The combination of "click" reactions and electrospinning has been found to provide a versatile platform to prepare ECM-like materials with biological functionalities via post-fabrication modification of nanofiber surfaces.

In another aspect, embodiments of the present invention relate to the polymer structures, fibers, coatings, films, or other objects made from or containing the amino acid based PEU's described above having bioactive molecules bonded to their pendant functional groups by means of a click reaction, as described above with respect to the polymer. Again, as set forth above, bioactive molecules are substances that influence cellular function and may include, without limitation, peptides, carbohydrates, proteins, oligonucleotides and small molecule drugs. In some embodiments, the bioactive molecule may be a peptide. In some embodiments, the bioactive molecule may be Lys(biotin), bone morphogenic protein-2 (BMP-2), bone morphogenic protein-7 (BMP-7), osteogenic growth peptide (OGP), or the c-terminal fragment of OGP [10-14] (YGFGG), GRGDS (RGD). In some embodiments, the bioactive molecule may be RGD.

In another aspect, embodiments of the present invention relate to methods for making the novel tyrosine based monomers functionalized to bond with a bioactive molecule via a "click" reaction described above. (See Example 20, below). In some of these embodiments, a functionalized tyrosine precursor is first dissolved in a suitable solvent. In some embodiments, the functionalized tyrosine precursor may have a protected ester group. In some embodiments, the functionalized tyrosine precursor may have a methyl protected ester group. In some embodiments, the functionalized tyrosine precursor may have a ethyl protected ester group. In some embodiments, the functionalized tyrosine precursor may have a tert-butyl protected ester group. In some embodiments, the functionalized tyrosine precursor may have a protected amine group. In some embodiments, the functionalized tyrosine precursor may have a boc protected amine group. In some embodiments, the functionalized tyrosine precursor may be a N-boc protected methyl ester of L-tyrosine, N-boc protected ethyl ester of L-tyrosine, N-boc protected tert-butyl ester of L-tyrosine, L-tyrosine, or DL-tyrosine or D-Tyrosine. In some embodiments, the functionalized tyrosine precursor may be a N-boc protected ethyl ester of L-tyrosine, L-tyrosine, or DL-tyrosine or D-Tyrosine. In some embodiments, the functionalized tyrosine precursor may be a N-boc protected tert-butyl ester of L-tyrosine, L-tyrosine, or DL-tyrosine or D-Tyrosine. In some embodiments, the functionalized tyrosine precursor may have the formula:

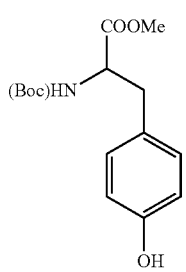

(XXXIV)

One of ordinary skill in the art will be able to select a suitable solvent without undue experimentation. Suitable solvents may include, without limitation, DMSO, CHCl₃, CH₂Cl₂, N-methyl pyrolidone, N,N-dimethyl formamide, hexafluoroisopropanol.

The hydroxyl group on the functionalized tyrosine precursor is then reacted with a functionalized alkyl halide that includes a pendent functional group (R). In some of these embodiments, the functionalized tyrosine precursor may have the general formula:

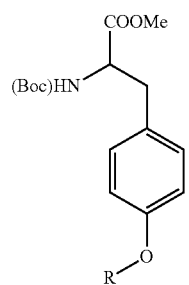

(XXXV)

wherein R is the pendent functional group.

As set forth above, pendent functional groups (R) that may be used are not particularly limited, provided that they are capable of a click reaction and can be attached to the phenol group of the tyrosine portion of the monomer. In some embodiments, suitable pendent functional groups may include, without limitation, an oxygen atom bound to a linear or branched alkyl and/or aryl group comprising a moiety capable of bonding by means of a click reaction. Suitable moieties include, without limitation, alkyne groups, alkene groups, azide groups, ketones or a strained cyclooctynes. In some embodiments, the pendent functional groups (R) may be CH₂C≡CH, CH₂CH₂CH₂N₃, CH₂CH₂CH₂CH=CH₂, or COCH₂CH₂COCH₃.

As set forth above, in certain embodiments the novel tyrosine based monomers of the present invention may also include one or more pendent functional groups (R) that while not themselves containing a clickable moiety, can readily be converted to include a clickable" moiety as described above. In some embodiments, the pendent functional groups (R) may be "protected" in any of a number of ways known in the art and must be "deprotected" before being used. In some embodiments, for example, the pendent functional groups (R) is a benzyl protected phenol group. In these embodiments, the benzyl protected phenol group must first be deprotected by removing the protecting benzyl group and adding a proton to form the phenol group (R=H) before the clickable ketone group may be added.

The specific mechanism for reacting the hydroxyl group on the functionalized tyrosine precursor with the functionalized alkyl halide having the pendent functional group (R), will depend on the specific pendent functional group (R) to be attached. In some embodiments, the pendent functional group (R) contains a clickable alkyne moiety, for example, CH₂C≡CH and is attached by reacting the functionalized tyrosine precursor with a functionalized alkyl halide having the pendent functional group (R) with the clickable alkyne moiety. In some embodiments, the phenol group on the functionalized tyrosine precursor may be reacted with propargyl bromide to make the propargyl derivatized tyrosine. In some embodiments, the pendent functional group (R) with the clickable alkyne moiety may be added to the functionalized tyrosine precursor as set forth in Example 2, below.

In some embodiments, the pendent functional group (R) contains a clickable azide moiety, for example, CH₂CH₂CH₂N₃, and is attached by reacting the functionalized tyrosine precursor with a functionalized alkyl halide, such as bromide, iodide or chloride. The halide is then converted to an azide by reacting it with sodium azide, resulting in the structure having a pendent functional group (R) with the clickable azide moiety. In some embodiments, pendent functional group (R) with the clickable azide moiety may be 3-azidopropyl 4-methylbenzinesulfonate, 4-azidobutyl 4-methylbenzinesulfonate, 5-azidopentyl 4-methylbenzinesulfonate, 6-azidohexyl 4-methylbenzinesulfonate. In some embodiments, the pendent functional group (R) with the clickable azide moiety may be added to the functionalized tyrosine precursor as set forth in Example 3, below.

In some embodiments, the pendent functional group (R) contains a clickable alkene moiety, for example, CH₂CH₂CH₂CH=CH₂ which is attached to the functionalized tyrosine precursor by reacting it with a functionalized alkyl halide having a pendent functional group (R) with the clickable alkene moiety. In some embodiments, the alkyl halide having the pendent functional group (R) with the clickable alkene moiety may be 5-bromo-1-pentene. In some embodiments, the alkyl halide having the pendent functional group (R) with the clickable alkene moiety may have the formula:

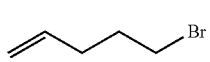

(XXXVI)

In some embodiments, the pendent functional group (R) with a clickable alkene moiety may be added to the functionalized tyrosine precursor as set forth in Example 4, below.

As set forth above, in certain embodiments the novel tyrosine based monomers of the present invention may also include one or more pendent functional groups (R) that can readily be converted to include a moiety capable of bonding by means of a click reaction (a "clickable" moiety) as described above. In some embodiments, the pendent functional group (R) is a benzyl protected phenol group (i.e. OCH₂Ph) and is attached by reacting the functionalized tyrosine precursor with a benzyl bromide to produce a functionalized tyrosine precursor having the pendent functional group (R) with a benzyl protected phenol group. In some embodiments, the pendent functional group (R) with the benzyl protected phenol group may be added to the functionalized tyrosine precursor as set forth in Example 5, below.

In some embodiments, the functionalized tyrosine precursor with the attached pendent functional group (R) described above may have a methyl, ethyl or tert-butyl protected ester group. In these embodiments, functionalized tyrosine precursor is then reacted with a suitable base to deprotect the ester group, changing it to a carboxylic acid group. In some embodiments, the compound produced may have the formula:

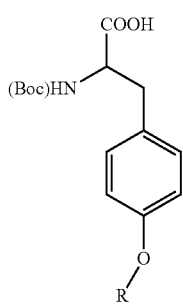

(XXXVII)

wherein R is the pendent functional group. One of ordinary skill in the art will be able to select a suitable base without undue experimentation. Suitable bases may include, without limitation, NaOH, KOH and/or combinations thereof. In some embodiments, the base may be NaOH in a methanol and water solution. In some embodiments, the base may be KOH in a methanol and water solution.

The functionalized tyrosine precursor is then reacted with a stoicheometrically appropriate quantity of a linear diol having from 2 to 12 carbon atoms, a suitable base catalyst, such as 4-(N,N-dimethylamino) pyridinium-4-toluenesulfonate (DPTS) and a coupling agent such as diisopropylcarbodiimide (DIPC) or dicyclohexylcarbodiimide (DCC), to produce a protonated salt of the Bis-diamino monomer. In some embodiments, the linear diol may be 1,6 hexadiol.

In some embodiments, the bis-diamino monomer has a boc protected amide that must be removed prior to the polymerization. In some embodiments, the boc protected bis-diamino monomer may have the formula:

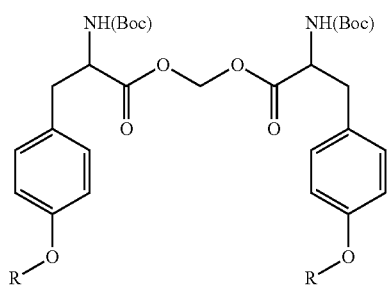

(XXXVIII)

In these embodiments the Boc-protected monomer is then dissolved in HCl and dioxane under a nitrogen or argon atmosphere and stirred for from 2 to 24 hours to remove the Boc groups producing a novel amino acid-based monomer for use in forming PEUs functionalized to bond with bioactive compounds. In some embodiments, the novel amino acid-based monomer for use in forming PEUs functionalized to bond with bioactive compounds has the general formula:

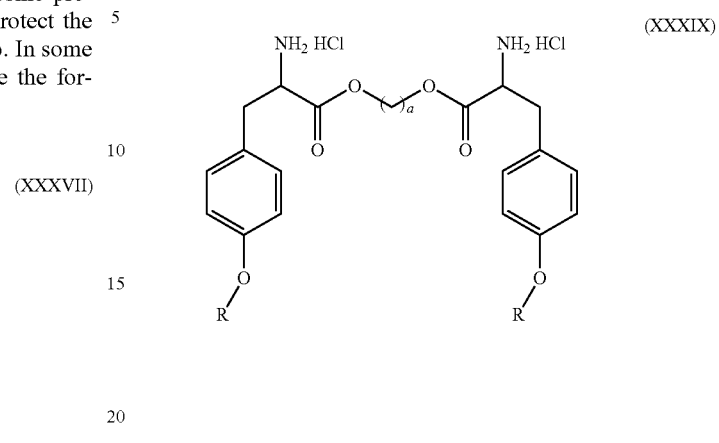

(XXXIX)

wherein R is the pendent functional group and a is an integer from 2 to 12. In some embodiments, a may be an integer from 4 to 10. In some embodiments, a may be an integer from 6 to 8. In some embodiments, a may be 6.

The novel amino acid-based monomer depicted in molecule (XXXIX) above, shows the amine groups ion protected by HCl, but the novel amino acid-based monomer are in no way so limited. As set forth above, these amine groups may be protected by any method known in the art for that purpose. In some embodiments, HCl, HBr and HI salts may be used to protect the amine groups on monomers according to the present invention. In some embodiments, para-toluene sulphonic acid (TosOH) may be used to protect the amine groups on monomers according to the present invention.

The organic solvents may be removed from the compound by any means known in the art for that purpose. In some embodiments, the organic solvents are removed by reduced pressure rotary evaporation or lyophilization. In some embodiments, the compound may be purified by washing it in diethyl ether and drying it in a vacuum.

In another aspect, embodiments of the present invention relate to methods for making the PEU's described above. In some embodiments, the PEU's described above may be formed by interfacial polymerization of the phenylalanine-based monomer described above and one or more of the tyrosine-based monomers described above using triphosgene or phosgene. Interfacial polymerization facilitates fast reaction rates and enables nearly quantitative yield at low temperature. In addition, precise stoichiometric control between the monomers and triphosgene is less critical as interfacial polymerization is kinetically controlled. And as set forth above, most, if not all, of the PEU polymers of the present invention are soluble in polar organic solvents, including N,N-dimethylformamide (DMF), dimethyl sulfoxide (DMSO), N-methyl-2-pyrrolidone (NMP), and hexafluoroisopropanol (HFIP). The solubility properties provide access to a number of approaches for solution processing methods for PEU, including solution casting, spinning coating and electrospinning.

In some embodiments, the amino acid based poly(ester ureas) of the present invention may be formed via interfacial polycondensation between the respective monomers and phosgene or triphosgene, as shown in Scheme 1, below.

Scheme 1

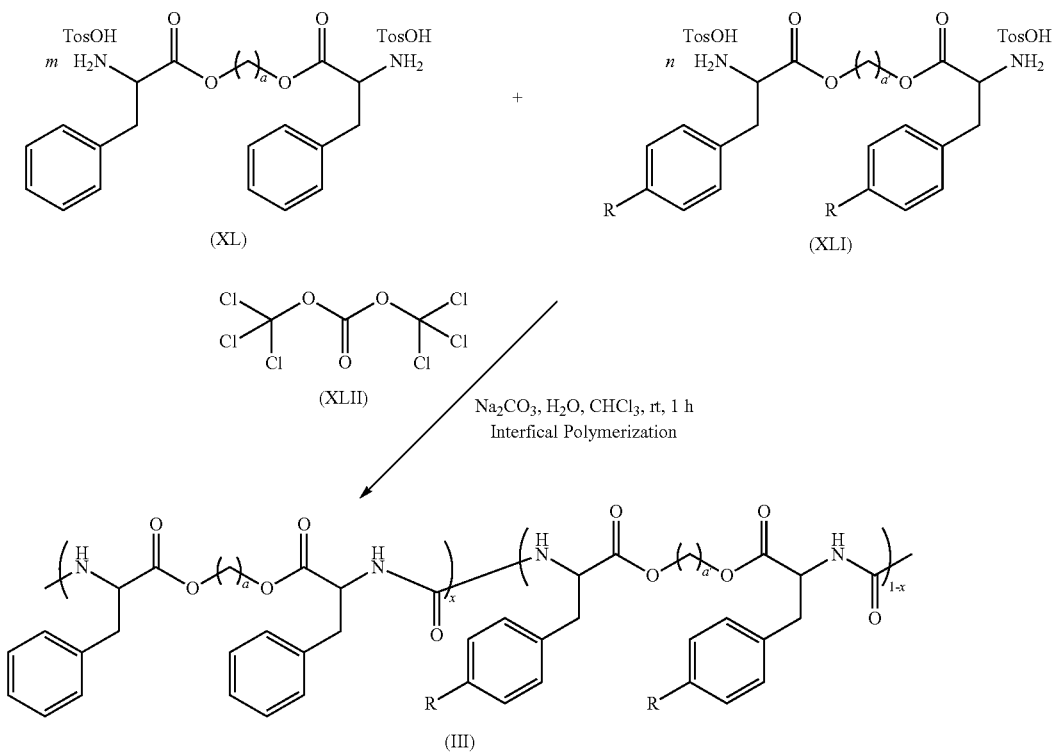

First, a phenylalanine-based monomer (as described above), a tyrosine-based monomer having one or more pendent functional groups (as described above), and a carbonic base such as sodium carbonate, potassium carbonate or other carbonic base are dissolved in a suitable aqueous solvent. One of ordinary skill in the art will be able to select a suitable aqueous solvent without undue experimentation but suitable aqueous solvents would include, without limitation, water and/or a buffered aqueous solution. In some embodiments, the phenylalanine-based monomer, the tyrosine-based monomer having one or more pendent functional groups, and sodium carbonate are dissolved in water and chloroform. In some embodiments, these reagents are dissolved in a container having mechanical or magnetic stirring.

In some embodiments, the phenylalanine-based monomer has the formula:

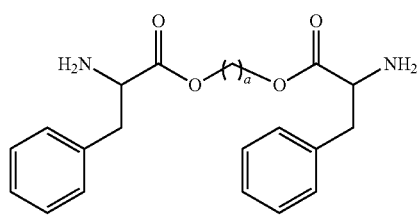

(X)

wherein a is an integer from 2 to 12.

In some embodiments, the tyrosine-based monomer has the formula:

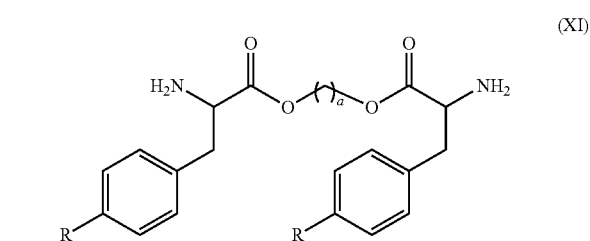

(XI)

wherein R is a linear alkyl or aryl group comprising an functional group capable of forming a chemical bond via a click reaction and a is an integer from 2 to 12. In some embodiments, the functional group may be an alkyne group, an alkene group, an azide group, a benzyl protected phenol group, or a ketone group. In some embodiments, R is —OH, —OCH$_2$C≡CH, —OCH$_2$CH$_2$CH$_2$N$_3$, —OCH$_2$CH$_2$CH$_2$CH=CH$_2$, —OCH$_2$Ph, or —COCH$_2$CH$_2$COCH$_3$.

It should be appreciated that the interfacial polymerization reaction shown in Scheme 1 above is exothermic. Accordingly, prior to the addition of the triphosgene (or phosgene), the temperature of the solution is then reduced to about 35° C. by any method known in the art. In some embodiments, the solution may be placed in a water bath having a temperature of from about −5° C. to about 5° C. until it reaches about 35° C. and then placed in a brine-ice bath until it reaches a temperature of from about −10° C. to about 10° C. In some embodiments, after the solution reaches a temperature of 35° C. it may be stirred for from about 1 hour to about 10 hours before it is placed in the brine-ice bath.

Separately, triphosgene or phosgene is dissolved in a suitable ahydrous organic solvent. One of ordinary skill in the art will be able to select a suitable organic anhydrous solvent without undue experimentation but suitable anhydrous organic solvents would include, without limitation, chloroform, methylene chloride, dioxane and/or combinations thereof.

As set forth above, in some embodiments of the PEUs of the present invention, the pendent functional group (R), while not clickable, may be readily converted to a clickable group. In some embodiments, the pendent functional group (R) may be an OH group or a benzyl protected phenol (R=—OCH$_2$Ph), as shown in Scheme 2 below.

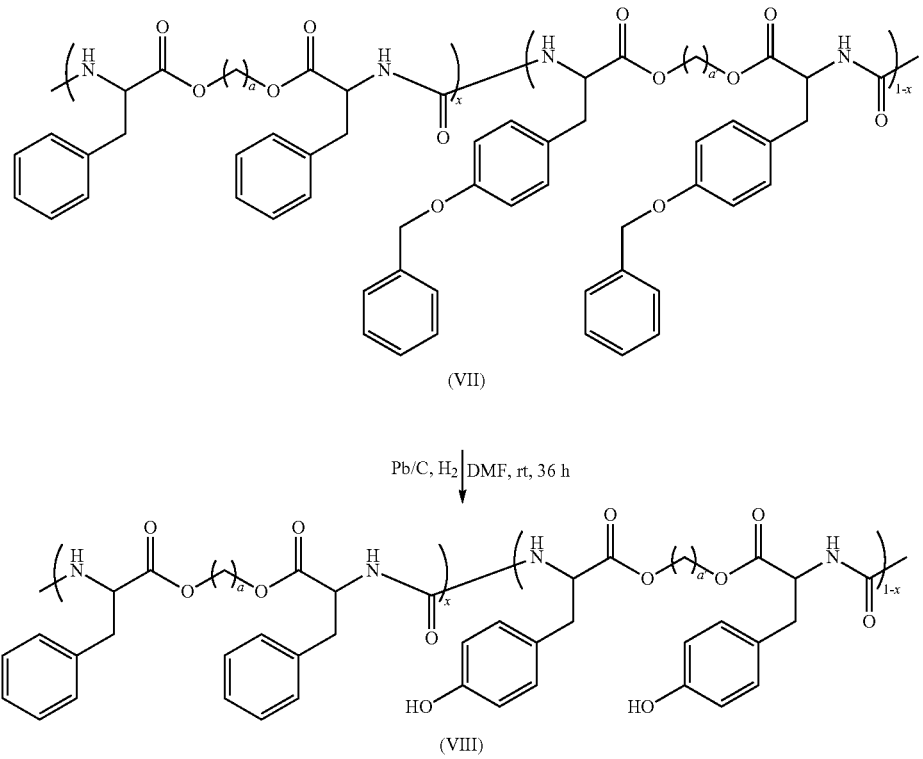

When the temperature of the monomer solution reaches about 0° C., an aliquat of the triphosgene (or phosgene) solution is added to the monomer solution to form a two phase system having an organic phase and an aqueous phase. The two phase system is then stirred for a period of from 1 to 10 hours before the two phase system is removed from the brine-ice bath. In some embodiments, the two phase system may be stirred for a period of from 1 to 5 hours. In some embodiments, the two phase system may be stirred for a period of from 2 to 3 hours. A second aliquot of the triphosgene solution is added to the two phase system before the organic phase and aqueous phase are separated. In some embodiments, the second aliquot of triphosgene solution is added dropwise over an additional 30 minute period.

The organic and aqueous phases are then separated by any conventional means and the organic phase containing the amino PEU functionalized to bond with a bioactive compound is collected. In some embodiments, the organic phase may be washed in water. The PEU may be removed from the organic phase by any means known in the art for that purpose. In some embodiments, the organic phase is the washed in an excess of hot water, causing said PEU to precipitate into the hot water. The precipitated PEU may be collected form the how water by any conventional method, including, without limitation, filtration or centrifugation. In these embodiments, the precipitated may be removed from the how water by filtration.

In these embodiments, a PEU having a benzyl protected phynol group (R=OCH$_2$Ph), is prepared as set forth above. The PEU with the benzyl protected phenol group is then dissolved in a suitable organic solvent. One of ordinary skill in the art will be able to select a suitable solvent without undue experimentation. Suitable solvents may include, without limitation, DMSO, CHCl$_3$, CH$_2$Cl$_2$, N-methyl pyrolidone, N,N-dimethyl formamide, hexafluoroisopropanol and combinations thereof.

Next, a catalytic amount of palladium on carbon catalyst is added to form a suspension, which is stirred under a hydrogen atmosphere at a temperature of from about 45° C. to about 55° C., for from 1 hour to about 24 hours, at a pressure of from 50 to about 70 psi. In some embodiments, the suspension may be stirred under a hydrogen atmosphere at a temperature of about 50° C. for 24 hours at a pressure of about 60 psi. One of ordinary skill in the art will be able to select a catalytic amount of palladium on carbon catalyst without undue experimentation. In some embodiments, a catalytic amount of palladium on carbon catalyst may be from 0.01 to 10 mole percent. In some embodiments, a catalytic amount of palladium on carbon catalyst may be from 0.01 to 1 mole percent. In some embodiments, a catalytic amount of palladium on carbon catalyst may be from 0.01 to 3 mole percent. In some embodiments, a catalytic amount of palladium on carbon catalyst may be from 2 to 8 mole percent. In some embodiments, a catalytic amount of palladium on carbon catalyst may be from 3 to 6 mole percent. In some embodiments, a catalytic amount of palladium on carbon catalyst may be from 4 to 6 mole percent. In some embodiments, a catalytic amount of palladium on carbon catalyst may be 0.1 mole percent.

In some embodiments, the suspension may be stirred under a hydrogen atmosphere at a temperature of from about 45° C. to about 55° C. In some embodiments, the suspension is stirred under a hydrogen atmosphere at a temperature of from about 48° C. to about 52° C. In some embodiments, the suspension is stirred under a hydrogen atmosphere for from 12 hours to about 24 hours. In some embodiments, the suspension is stirred under a hydrogen atmosphere for from 18 hours to about 24 hours. In some embodiments, the suspension is stirred under a hydrogen atmosphere at a pressure of from 50 to about 70 psi. In some embodiments, the suspension is stirred under a hydrogen atmosphere at a pressure of from 55 to about 65 psi. In some embodiments, the suspension is stirred under a hydrogen atmosphere at a pressure of from 58 to about 62 psi.

The suspension may then be filtered through a celite column and the filtrate collected and concentrated by conventional methods. In some embodiments, the suspension may be filtered through a Celite 545 column. The filtrate may be concentrated in any conventional method. In some embodiments, the filtrate may be concentrated by rotary evaporation or under reduced pressure.

The concentrated filtrate is then added to an excess volume of water to precipitate out a PEU functionalized to bond with a bioactive compound, having the formula:

(VIII)

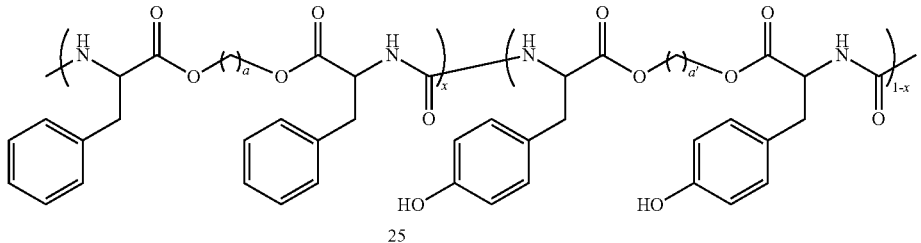

wherein a and a' are integers from 2 to 12 and x is the mole percentage of phenylalanine based segments in the polymer and 1-x is the mole percentage of the tyrosine-based segments of the polymer. The polymer may be collected, purified, and dried by conventional methods. In some embodiments, the polymer may be collected by filtration, rotary evaporation or reduced pressure. In some embodiments, the polymer may be purified by washing with water. In some embodiments, the polymer may be dried by vacuum oven.

In some embodiments, the PEU having an OH pendent functional group polymer (PEU-6) may be modified with levulinic acid to add a ketone functional group as shown in Scheme 3, below. For example the phenolic unit of the tyrosine is condensed on the acid group of levulinic acid (or any other aliphatic compound containing an acid group and a ketone group). The acid group of the levulinic acid is condensed on the phenol to form an ester linkage. The number of methylene groups can vary between 2 and 6 groups between the carbonyl of the ester and the ketone group. The ketone group is the clickable species at the end of this reaction.

Scheme 3

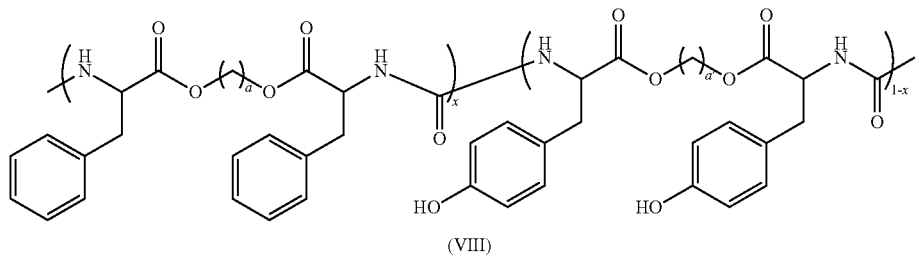

(VIII)

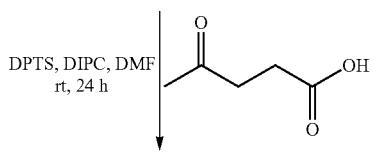

DPTS, DIPC, DMF
rt, 24 h

-continued

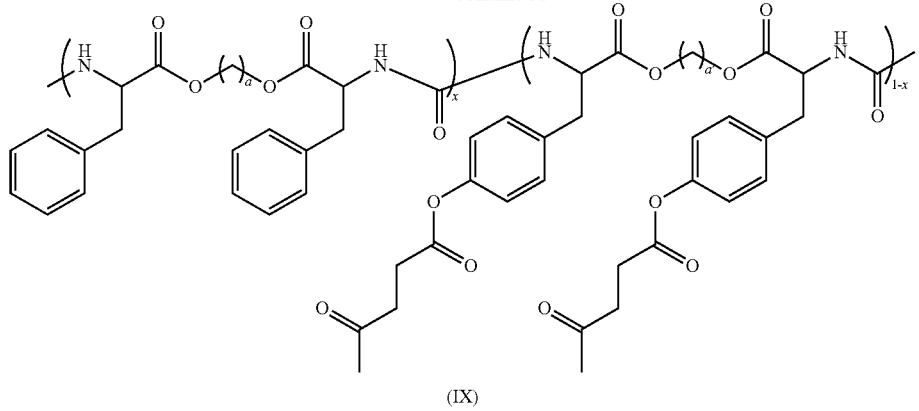

(IX)

The amino acid-based poly(ester urea) having a pendent hydroxyl functional group described above is first dissolved in a suitable solvent. One of ordinary skill in the art will be able to select a suitable organic solvent without undue experimentation. Suitable solvents may include, without limitation, DMF, NMP, HFIP, chloroform, and combinations thereof.

Next, stoichiometrically appropriate quantities of levulinic acid and a suitable base are added to the polymer solution. One of ordinary skill in the art will be able to select a suitable base without undue experimentation. Suitable bases may include, without limitation, 4-(N,N-dimethylamino) pyridinium-4-toluenesulfonate (DPTS), and combinations thereof. In some embodiments the bass is 4-(N,N-dimethylamino) pyridinium-4-toluenesulfonate (DPTS). One of ordinary skill in art will be able to determine stoichiometrically appropriate quantities of the levulinic acid and suitable base without undue experimentation. In some embodiments, a stoichiometrically appropriate quantity of levulinic acid is from about 1 to about 5. In some embodiments, a stoicheometrically appropriate quantity of base is from about 1 to about 2.

The solution is then cooled to a temperature of from about −5° C. to about 5° C. The solution may be cooled by any conventional method including, without limitation an ice bath or brine ice bath. In some embodiments, solution may be cooled to a temperature of from about −2° C. to about 2° C.

Next, a stoicheometrically appropriate quantity of 1,3-diisopropyl cabodiimide (DIPC) is added to the solution to aid in the coupling of the acid with the phenol. One of ordinary skill in art will be able to determine stoicheometrically appropriate quantities of the 1,3-diisopropyl cabodiimide (DIPC) without undue experimentation. In some embodiments, a stoicheometrically appropriate quantity of 1,3-diisopropyl cabodiimide (DIPC) is from about 1 to about 10. The mixture is then allowed to warm up to ambient temperature and stirred for from about 2 hours to about 24 hours. In some embodiments, the mixture may be stirred from about 2 hours to about 12 hours. In some embodiments, the mixture may be stirred from about 2 hours to about 6 hours. In some embodiments, the mixture may be stirred for about 2 hours/minutes.

The mixture is then added to an excess volume of methanol and/or ethanol to produce a PEU having the formula:

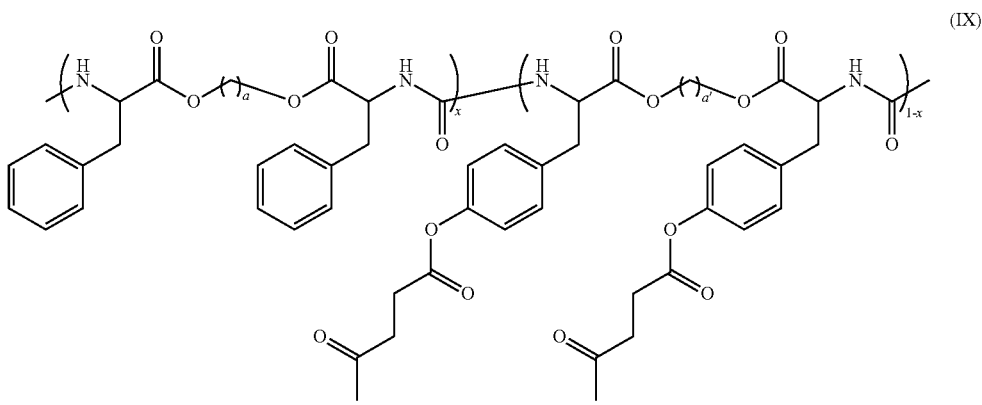

(IX)

wherein a and a' are integers from 2 to 12, x is the mole percentage of phenylalanine based segments in the polymer, and 1-x is the mole percentage of the tyrosine-based segments of the polymer.

The polymer may be collected, purified, and dried by conventional methods. In some embodiments, the polymer may be collected by filtration or centrifugation. In some embodiments, the polymer may be purified by re-precipitation.

In another aspect, embodiments of the present invention relate to methods for attaching bioactive compounds to PEU's functionalized to bond to them by any via one of "click" reactions as discussed above. As set forth above, in some embodiments, the amino acid-based poly(ester urea) polymer has been formed into structure, coating, or film, examples of which may include, without limitation, fibers, films, tissue scaffolds, tubes, pins, coatings, or medical devices. In some embodiments, the amino acid-based poly (ester urea) polymer structure, coating or film is a microfiber or nanofiber.

As set forth above, the bioactive compounds can be attached to the functionalized amino acid-based poly(ester urea) described above or to any structure, coating, or film made therefrom. First, a suitable bioactive compound to be attached to the amino acid-based poly(ester urea) polymer or structure, coating, or film is selected. As set forth above, suitable bioactive compounds may include, without limitation, peptides, carbohydrates, proteins, oligonucleotides and small molecule drugs. In some embodiments, the bioactive compound may be Lys(biotin), bone morphogenic protein-2 (BMP-2), bone morphogenic protein-7 (BMP-7), osteogenic growth peptide (OGP), or the c-terminal fragment of OGP [10-14] (YGFGG), GRGDS (RGD) or any combinations thereof.

As set forth above, the selected bioactive molecule must contain a functional group that is capable of forming a chemical bond with one or more of the pendent functional groups found in the pre-fabricated PEU using a click reaction. In some embodiments, the functional group on said bioactive compound may be an azide group, a thiol group, an alkyne group, an alkene group, and/or combinations thereof. In some embodiments, the functional group on said bioactive compound is an azide group and the pendant functional group is an alkyne group. In some embodiments, the functional group on said bioactive compound is an alkyne group and the pendant functional group is an azide group. In some embodiments, the functional group on said bioactive compound is a thiol group and the pendant functional group is an alkene group. In some embodiments, the functional group on said bioactive compound is an amine or hydroxyl amine and the pendant functional group is a ketone group.

In some embodiments, the necessary functional group may be naturally present in the selected bioactive molecule. For example, thiols in cysteine, acid groups in aspartic acid or glycolic acid or phenol groups in tyrosine. In some embodiments, the selected bioactive molecule may be added during fabrication the bioactive molecule. With the development of microwave-assisted SPPS, it has become relatively straight forward to prepare peptides containing up to 50 amino acid residues. In some embodiments, bioactive molecules such as peptides may be tagged with functional groups that undergo "click" reactions by directly coupling a non-canonical amino acid containing a pre-selected functional group within the peptide during synthesis. If the functional position is at the N-terminus, acids with "clickable" groups are readily available for use following cleavage. The obvious advantage of this method is that it the precise control of functional position along the peptide chain by simply altering the coupling sequence. The only limitation is that the desired functional groups must be compatible with the reaction conditions for peptide coupling, deprotection and cleavage; otherwise, certain protection of the functional groups is required. Azide, alkyne, alkene, thiol, maleimide, and aminooxy groups have successfully been introduced into peptides through this strategy.

Among different types of functional groups, peptides with an azide tag are used most frequently, mainly due to their high bioorthogonal selectivity and the versatile reactivity in different "click" reactions. The "click" reactions using an azide group include CuAAC, SPAAC, Staudinger ligation and tandem [3+2] cycloaddition-retro-Diels-Alder reaction (tandem crD-A). Peptides with an azide group may be synthesized either by directly coupling the peptide with azido acid, or by post transfer of bromine to azide. For the direct coupling of an azido amino acid or an azido acid with a peptide, there are many known candidate molecules. Considering the safety issues with organic azides, the preferred coupling step of a peptide with an azido amino acid is using manual (not microwave) SPPS methods. The cleavage cocktail needs to avoid the usage of thiol-scavengers, because the azide would be reduced to an amine by 1,2-ethanedithiol during the cleavage reaction.

The other functional group that is notable due to its versatile reactivity in several types of "click" reactions is the thiol group. Peptides with a thiol group were readily prepared by coupling with cysteine, a natural amino acid containing a thiol in the side group. It is also possible to reduce the disulfide bonds in proteins with a reductive agent to obtain free thiol groups in situ for further functionalization. A thiol group is capable of reacting with an alkene under irradiation through a thiol-ene reaction, with an alkyne under irradiation through a thiol-yne reaction, with an electron-deficient alkene through Michael addition, and with dipyridyl disulfide. In addition to the noted reactions, the cysteine at the N-terminus of a peptide is able to couple with a thiol ester by native chemical ligation (NCL), and with an aldehyde through thiazolidine ligation. Because of the diverse reactivity with different functional groups, peptides with thiol groups have been widely used to synthesize peptide-conjugates with carbohydrates, polymers, and fluorescein.

In SPPS, residues of amino acids that are reactive or unstable during the coupling and deprotection steps are often protected with orthogonal protecting groups. By carefully choosing the protecting groups on the side chain residues of amino acids, one may selectively functionalize the peptide at a specific site. This is a complementary method with direct coupling of a non-canonical amino acid with peptide, due to the difficulty of synthesizing non-canonical amino acids. For example, the protection group (4,4-dimethyl-2,6-dioxocyclohex-1-ylidine)ethyl (Dde) in Fmoc-Lys(Dde)-OH can be deprotected using mild conditions while other protected amino acid residues are stable, generating an amine group that can be functionalized with an alkene or a di-fluorocyclooctyne group.

In some embodiments, the functional groups may be added to naturally occurring or pre-fabricated bioactive molecules by derivatizing the N-terminus of the peptide or protein with functional a linker during the synthetic process.

Next, an amino acid-based poly(ester urea) polymer structure, coating, or film comprising an amino acid based poly(ester urea) polymer having at least one phenylalanine-based monomer segment and at least one tyrosine-based monomer segment having one or more pendent functional groups capable of bonding to the functional group on said bioactive compound using a click reaction is prepared as set forth above. The functionalized bioactive molecules and the amino acid-based poly(ester urea) polymer structure, coating, or film are combined and the functional groups on said bioactive compound are reacted with the functional groups on said amino acid-based poly(ester urea) structure, coating, or film using a click reaction, thereby forming bonds between said bioactive compound and said amino acid-based poly(ester urea) polymer structure, coating, or film and attaching said bioactive compound to said amino acid-based poly(ester urea) polymer structure, coating, or film. It should be appreciated that the specific reaction conditions will depend upon the particular click reaction being used, which are well known in the art. See Examples 11-13, 20, below.

Experimental

Polymeric nanofiber matrices are routinely used in biomedical applications, due to their morphological and structural similarities to the natural extra-cellular matrix (ECM). Nanofibers may be obtained via electrospinning of polymer solutions or from the melt. The physical and dimensional properties of fiber matrices can be tuned precisely. Fiber diameter, alignment, surface-to-volume ratio, and porosity can be controlled in the electrospinning process, by methods well known in the art. The combination of "click" reactions and electrospinning provides a versatile platform to prepare ECM-like materials with biological functionalities via post-fabrication modification of nanofiber surfaces.

Figure 1B:
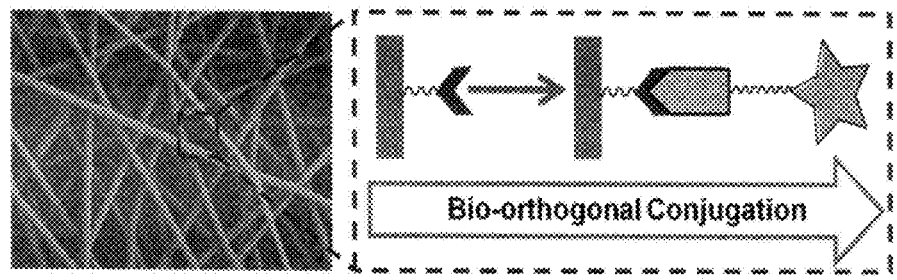
Figure 12:
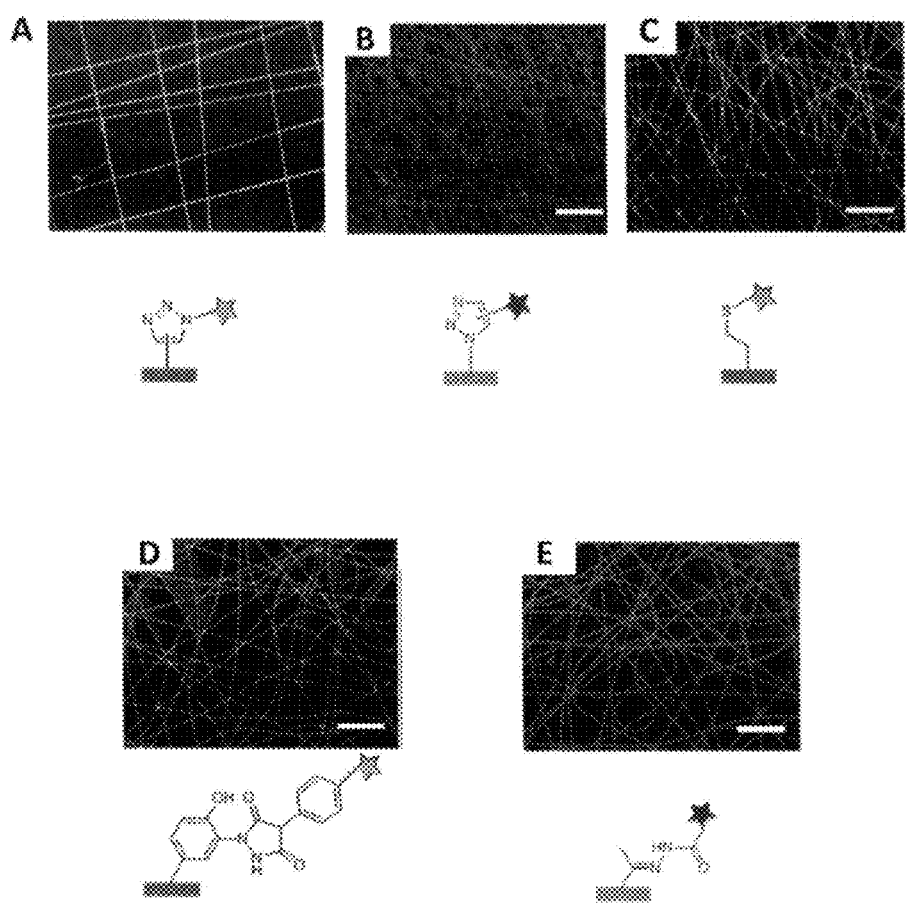
FIGS. 12A-E are images of nanofibers that were modified post-electrospinning and the corresponding chemical reactions: (A) Chemical reaction site between PEU-2 and chremo 488 azide via CuAAC; (B) Chemical reaction site between PEU-3 and alkyne-RGD-biotin via CuAAC; (C) Chemical reaction site between PEU-4 and FITC-RGD-thiol via thiol-ene reaction; (D) Chemical reaction scheme between PEU-6 and alkyne derived diazodicarboxamide; (E) Chemical reaction site between PEU-7 and Alexa fluor 568 hydrazide fluorescence via hydrazone formation. Fluorescent images of labeled PEU nanofibers (×20, scale bar 50 μm).
Figure 13:
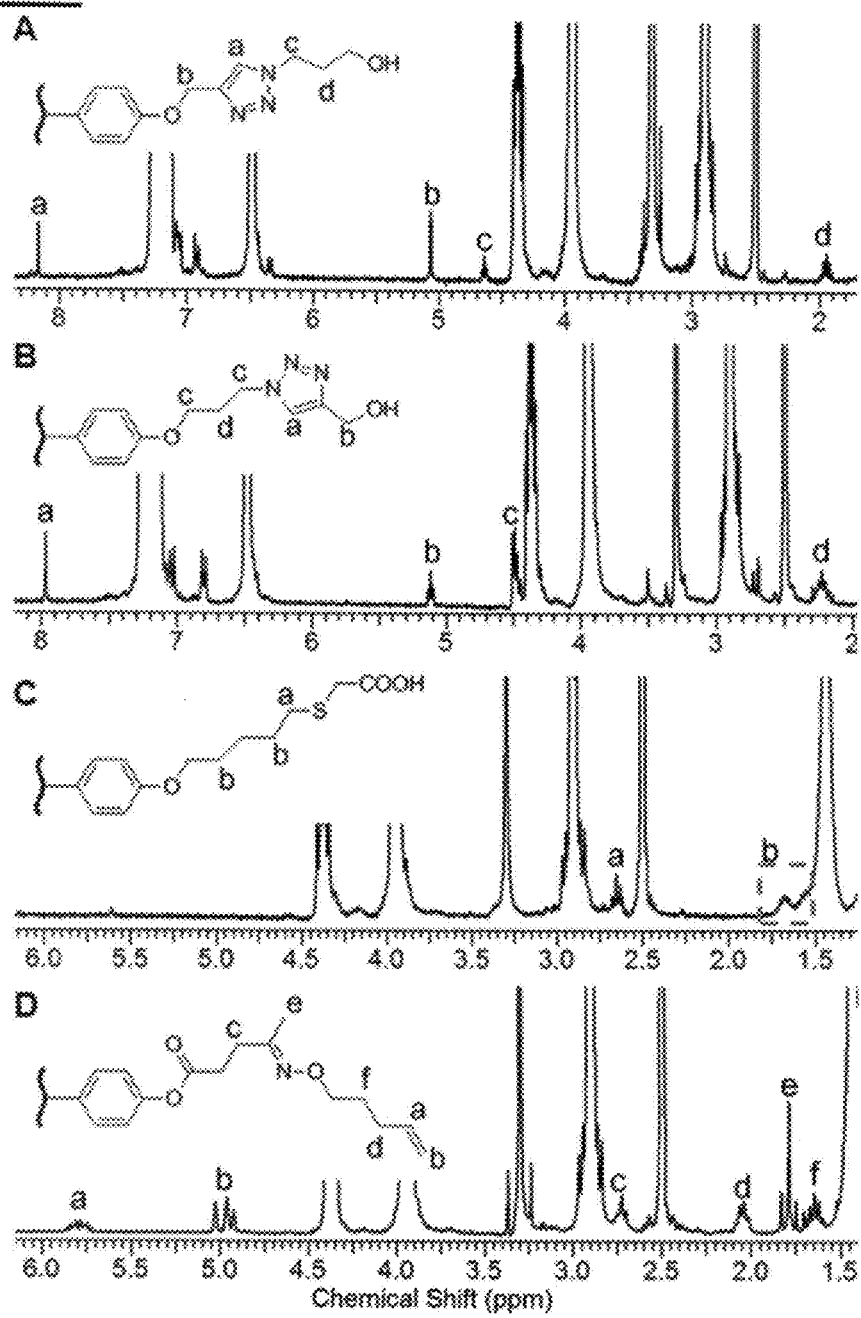
FIGS. 13A-D are $^1$H NMR spectra of PEUs following derivation with small molecule probes (DMSO-$d_6$) according to various embodiments and aspects of the present invention. (A) Huisgen cycloaddition product between PEU-2 and 3-azidopropan-1-ol: triazole proton signal 8.12 ppm; (B) Huisgen cycloaddition product between PEU-3 and propargyl alcohol: triazole proton signal 7.96 ppm; (C) Thiol-ene addition product between PEU-4 and mercaptopropionic acid: product signal 2.65 ppm (—CH$_2$SCH$_2$COOH) and disappearance of alkene protons; (D) Oxime ligation product between PEU-7 and o-(pent-4-en-1-yl) hydroxylamine (LVI): product signals 5.85 ppm (—CH2CH=CH$_2$), 5.00 ppm (—CH$_2$CH=CH$_2$), and 1.76 ppm (—CH$_2$C(=N)CH$_3$).
Figure 14:
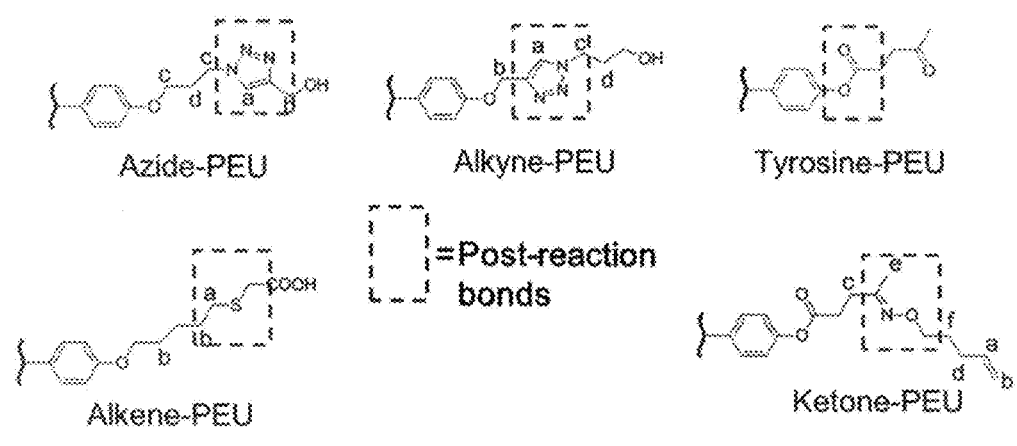
FIG. 14 is a schematic showing small molecule probes with corresponding reactive groups.

As further described in the Examples that follow, L-phenylalanine and L-tyrosine-based PEU copolymers bearing various "clickable" pendent groups, including alkyne (PEU-2), azide (PEU-3), alkene (PEU-4), tyrosine-phenol (PEU-6), and ketone (PEU-7) were synthesized and tested to better explain and confirm various aspects of the present invention. (See FIGS. 2-11; Examples 1-5) Model reactions with peptides or fluorescent molecules (See Examples 11-13, 20) demonstrated the presence of "clickable" sites on the surfaces of electrospun PEU nanofibers (See FIGS. 1B, 12) and that these "clickable" cites were available for post-fabrication functionalization. (See FIGS. 13, 14).

The chemical structures of the monomers and a general synthetic route for functional PEU's according to these embodiments of the present invention are shown in Schemes 1 and 2, above and the corresponding $^1$H NMR and $^{13}$C NMR in FIGS. 2-11. The individual synthetic schemes and procedures are described in more detail in the Examples below. The phenylalanine-based PEU (PEU-1) was used as a control and used possesses no chemically derivatizable functionalities. The PEUs possessing functional alkyne (PEU-2), azide (PEU-3), alkene (PEU-4), benzyl-protected phenolic tyrosine (PEU-5), unprotected tyrosine-phenol (PEU-6), and ketone units (PEU-7) can be synthesized using a copolymerization approach that is highly versatile. PEU-1, -2, -3, -4 and -5 were synthesized using interfacial polymerization as described above. (See Scheme 1, above; Example 8, below) PEU-6 was obtained by deprotection of the benzyl groups in PEU-5 and PEU-7 was obtained via carbodiimide coupling between PEU-6 and levulinic acid. (See Scheme 2, above; Examples 9, 10, below)

Five monomers (M1-M5) representing various derivatization chemistries according to embodiments of the present invention (were synthesized and characterized with $^1$H NMR (FIGS. 2,4,6,8,10) and $^{13}$C NMR (FIGS. 3, 5, 7, 9, 11).

Figure 2:
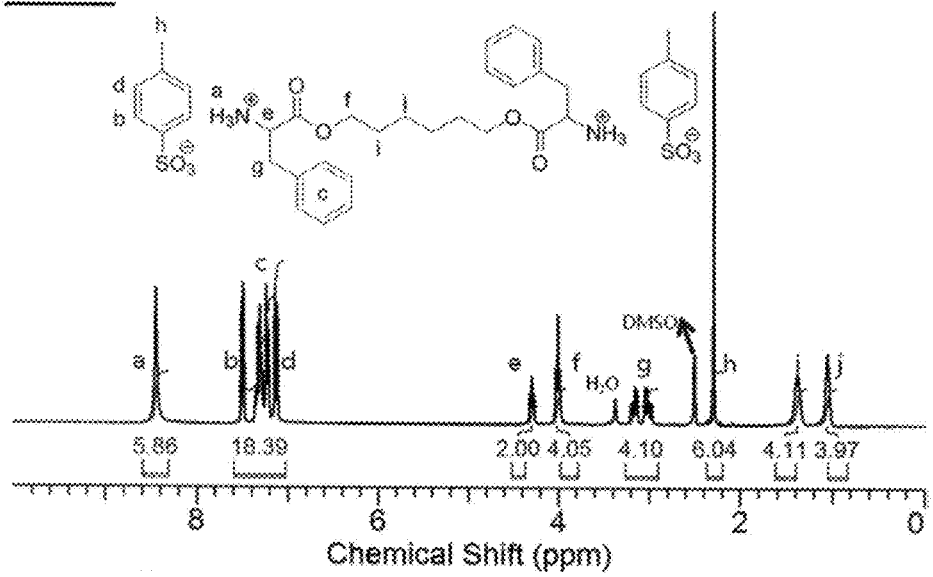
FIG. 2 is a $^1$H NMR (DMSO-$d_6$) spectrum of PEU-1 monomer (X) (M1).
Figure 3:
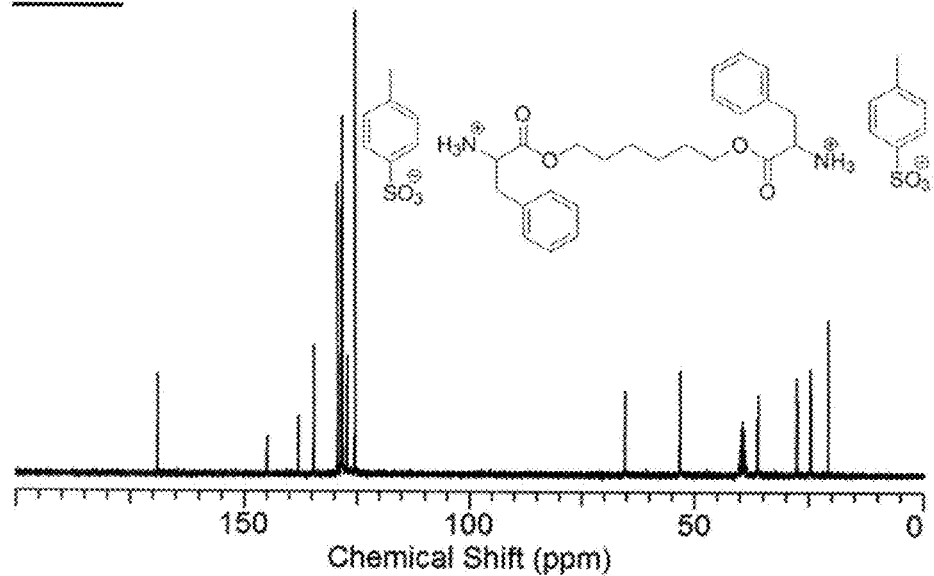
FIG. 3 is a $^{13}$C NMR (DMSO-$d_6$) spectrum of PEU-1 monomer (X) (M1).

FIG. 2 shows the $^1$H NMR spectrum of the phenylalanine-based monomer (M1), which lacks functional groups, but is used to form PEU-1 through PEU-7.

Figure 4:
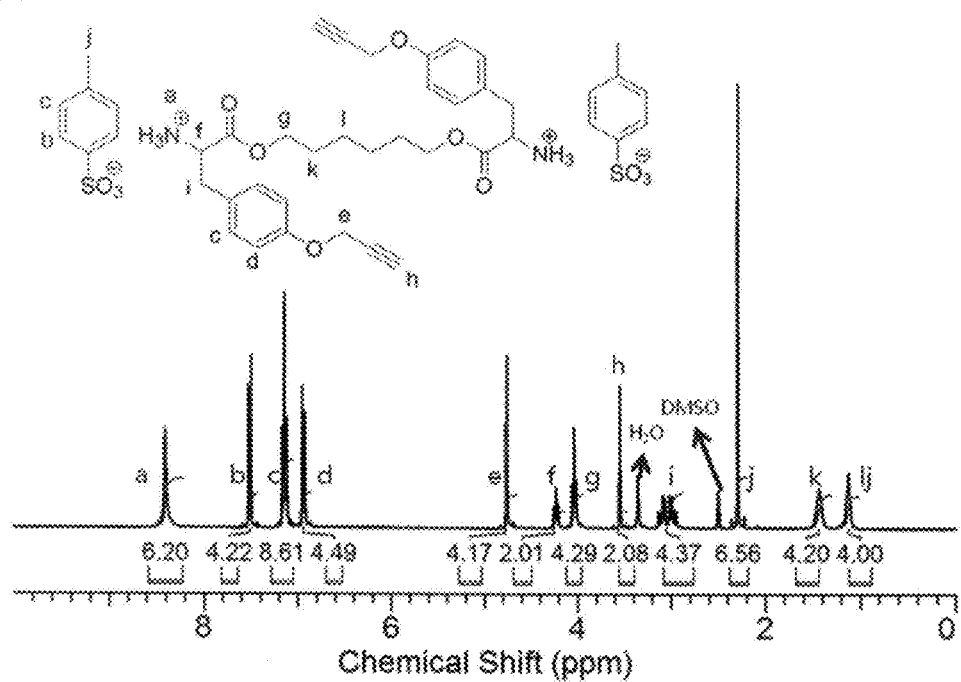
FIG. 4 is a $^1$H NMR (DMSO-$d_6$) spectrum of PEU-2 monomer (XII) (M2).
Figure 5:
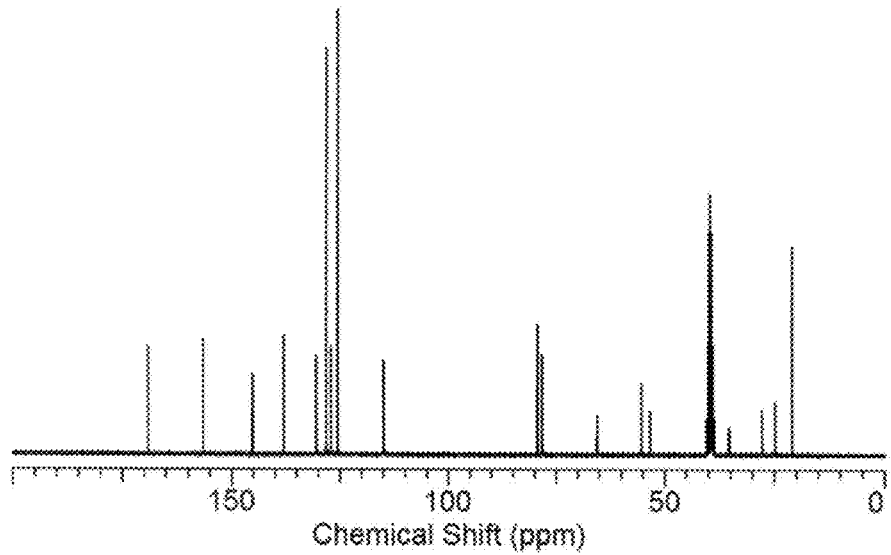
FIG. 5 is a $^{13}$C NMR (DMSO-$d_6$) spectrum of PEU-2 monomer (XII) (M2).

FIG. 4 shows the $^1$H NMR spectrum of the alkyne-derived monomer (M2), used for the synthesis of PEU-2. As can be seen in FIG. 4, the alkyne CH peak is observed at 3.55 ppm, and the corresponding methylene is located at 4.76 ppm. The aromatic hydrogens of tyrosine have chemical shifts at 7.06 ppm and 6.86 ppm, which are different from those of phenylalanine located between 7.00 ppm and 7.53 ppm.

Figure 6:
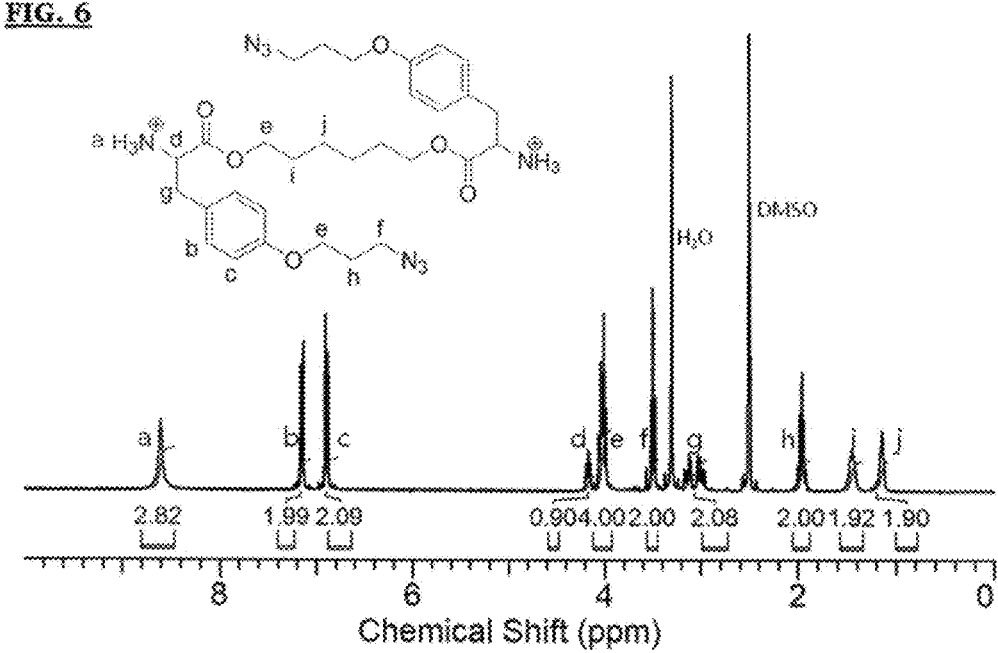
FIG. 6 is a $^1$H NMR (DMSO-$d_6$) spectrum of PEU-3 monomer (XV) (M3).
Figure 7:
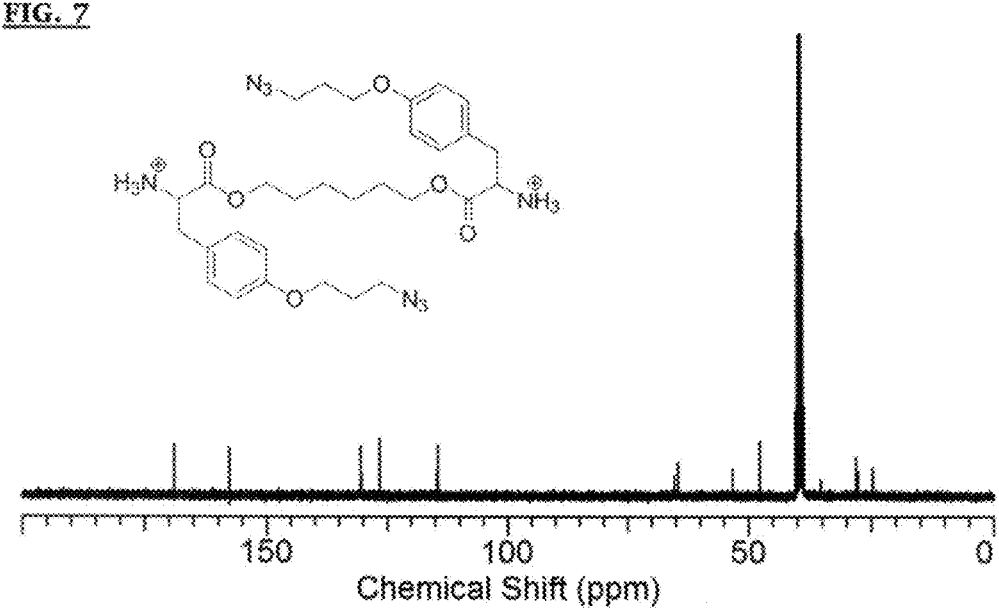
FIG. 7 is a $^{13}$C NMR (DMSO-$d_6$) spectrum of PEU-3 monomer (XV) (M3).
Figure 8:
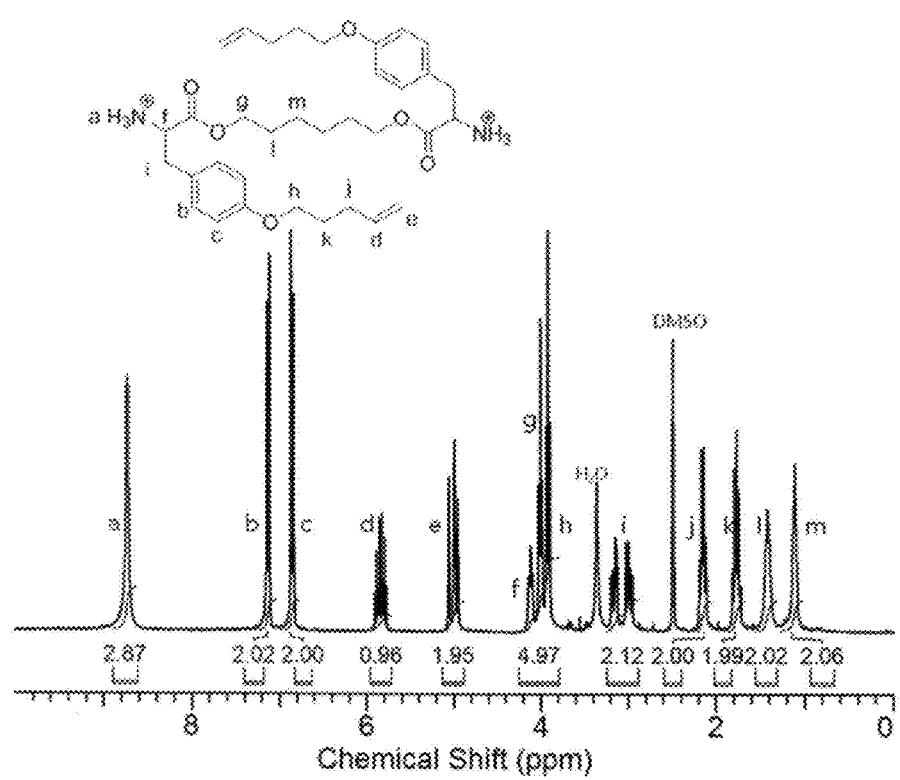
FIG. 8 is a $^1$H NMR (DMSO-$d_6$) spectrum of PEU-4 monomer (XIX) (M4).
Figure 9:
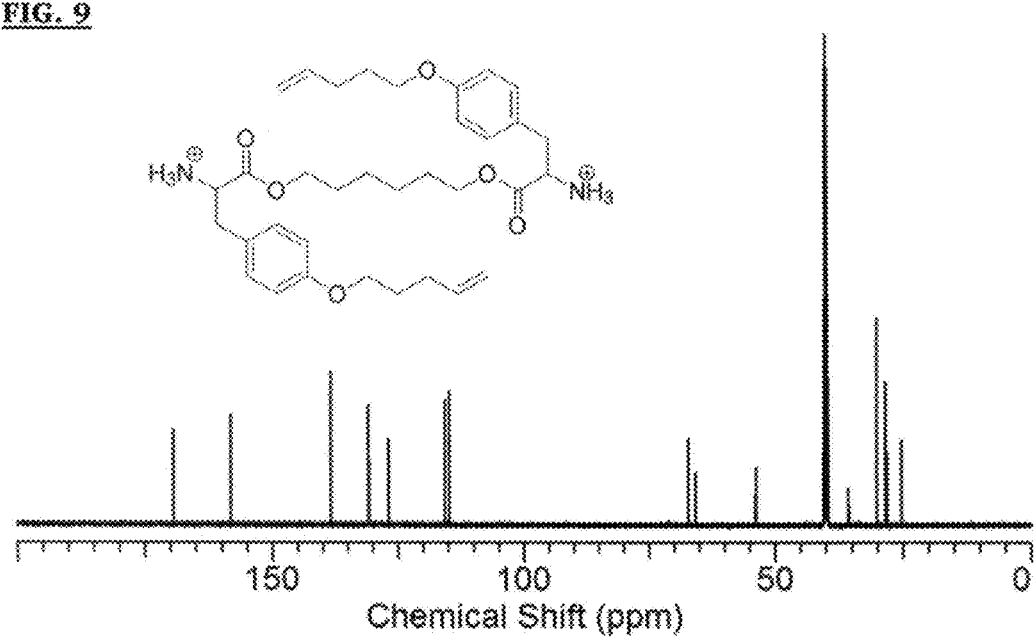
FIG. 9 is a $^{13}$C NMR (DMSO-$d_6$) spectrum of PEU-4 monomer (XIX) (M4).
Figure 10:
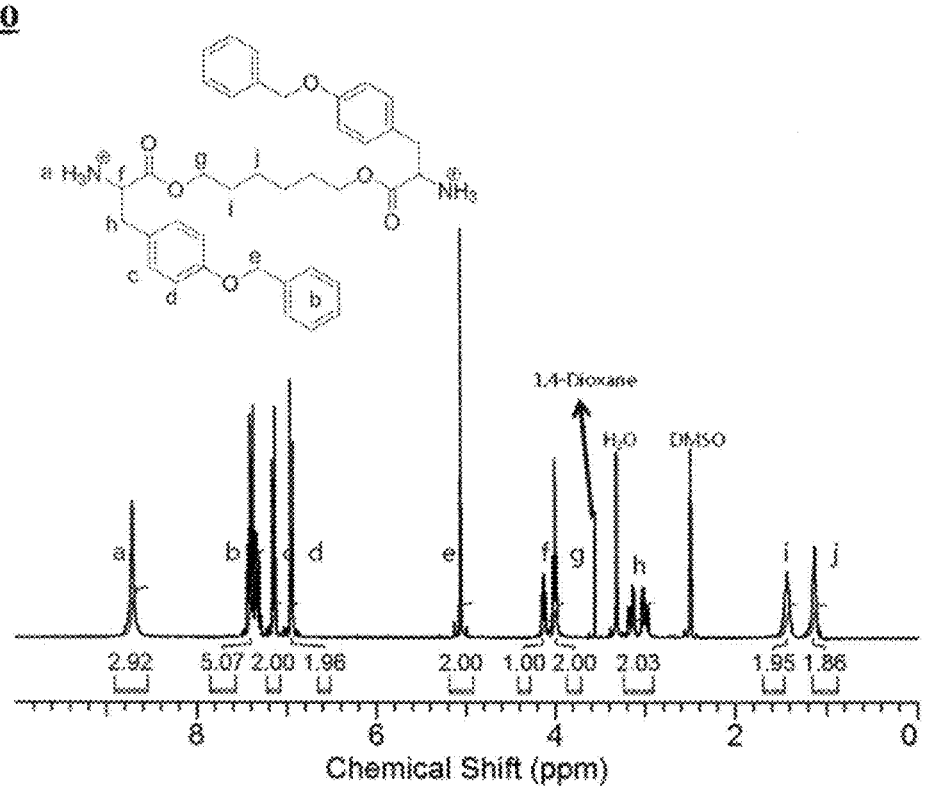
FIG. 10 is a $^1$H NMR (DMSO-$d_6$) spectrum of PEU-5 monomer (XXIX) (M5).
Figure 11:
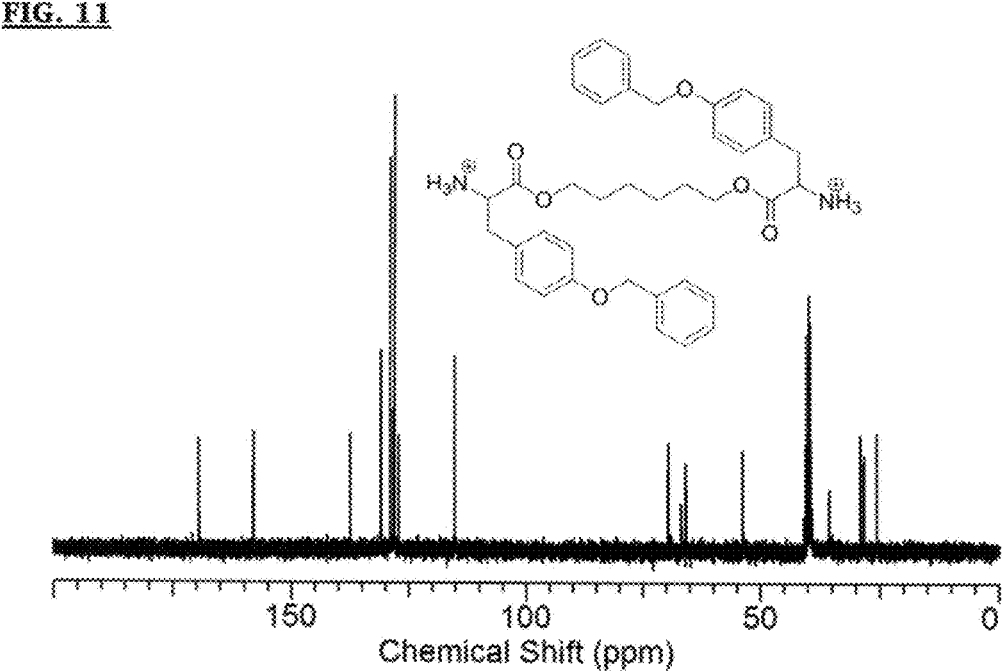
FIG. 11 is a $^{13}$C NMR (DMSO-$d_6$) spectrum of PEU-5 monomer (XXIX) (M5).

FIG. 6 shows the $^1$H NMR spectrum of the monomer containing azide (M3), used for the synthesis of PEU-3. As can be seen in FIG. 6, the peak at 3.50 ppm is assigned to the methylene adjacent to the azide. In FIG. 8, shows the $^1$H NMR spectrum of the alkene monomer (M4), used for the synthesis of PEU-4. As can be seen in FIG. 8, the PEU-4 monomer shows the characteristic alkene peaks at 5.85 ppm and 5.00 ppm. For the benzyl protected tyrosine monomer (M5) in FIG. 10 and used for the synthesis of PEU-5, the benzyl group has chemical shifts in the range of 7.25 ppm to 7.50 ppm, and the singlet at 5.07 ppm is assigned to the benzyl methylene. It is important to note that, within the limit of $^1$H NMR detection, there are no amine salts in the monomers, which is important if high molecular mass polymers are to be obtained in the AA-BB-type step-growth polymerization according to embodiments of the present invention. All of the monomers were stored as the quantitative amine salt. The free amine was generated in situ using sodium carbonate at the beginning of the polymerization.

In these embodiments, the PEUs were obtained via interfacial polycondensation reactions between the respective monomers and triphosgene as shown in Scheme 1 above. The resulting polymers have a weight average molecular mass ($M_w$) near 100 kDa. The corresponding mass data is summarized in Table 1.

TABLE 1

| | \multicolumn{7}{c}{Molecular mass data of PEUs.} |
|---|---|---|---|---|---|---|---|
| | PEU-1 | PEU-2 | PEU-3 | PEU-4 | PEU-5 | PEU-6 | PEU-7 |
| $^a M_w$ | 132,100 | 117,600 | 118,900 | 110,200 | 96,300 | 89,400 | 93,200 |
| $^b D_m$ | 1.21 | 1.28 | 1.21 | 1.37 | 1.37 | 1.50 | 1.39 |

$^a$Mass average molecular weight (g/mol);
$^b$ Distribution of molecular mass ($D_m$, $M_w/M_n$) of polymers after precipitation in water, which significantly narrows the molecular mass distribution from what is expected in a step growth polymerization.

As set forth above, random copolymerization of functionalized tyrosine-based monomers and phenylalanine-based monomers yielded PEU with "clickable" pendent groups (Schemes 1 and 2). The content of the functional units was controlled by the feed ratio of the respective monomers. Five different "clickable" groups were incorporated separately into the polymers. PEU-2 (alkyne-PEU) and PEU-3 (azide-PEU) are designed for copper (I) catalyzed azide-alkyne cycloaddition reactions (CuAAC). PEU-4 (alkene-PEU) can be used for thiol-ene radical addition derivation, and PEU-7 (keto-PEU) is able to react with aminooxy and hydrazine groups through a condensation process.

In addition, the phenol group of tyrosine is esterification active, which permits polymer modification using carboxylic acids through carbodiimide coupling.

Figure 15:
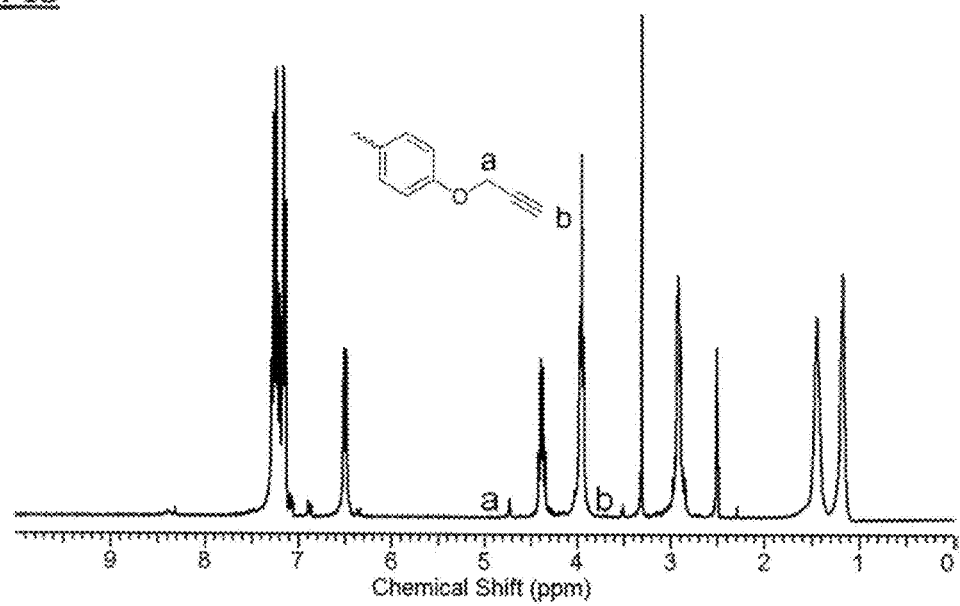
FIG. 15 is a $^1$H NMR of PEU-2 nanofibers
Figure 16:
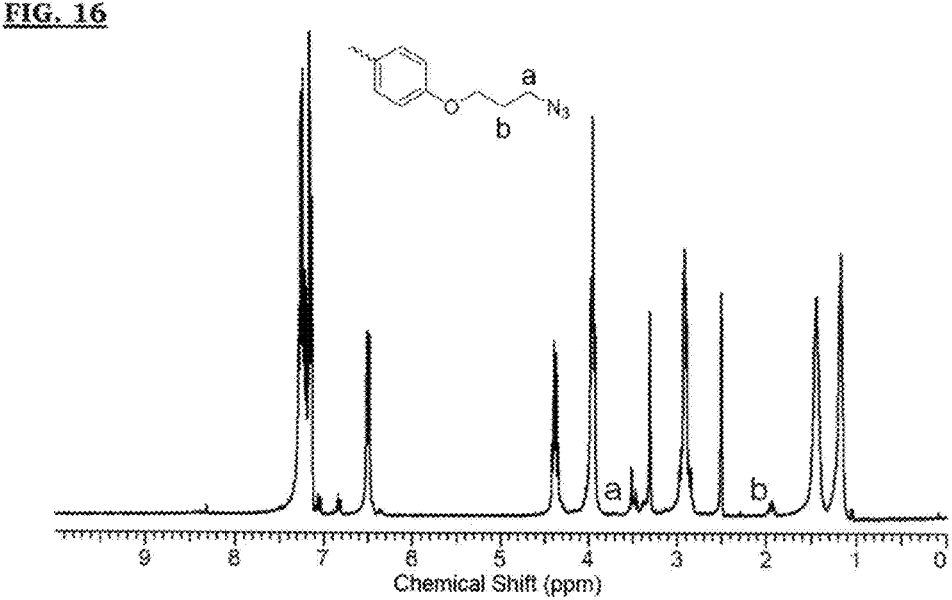
FIG. 16 is a $^1$H NMR of PEU-3 nanofibers.
Figure 17:
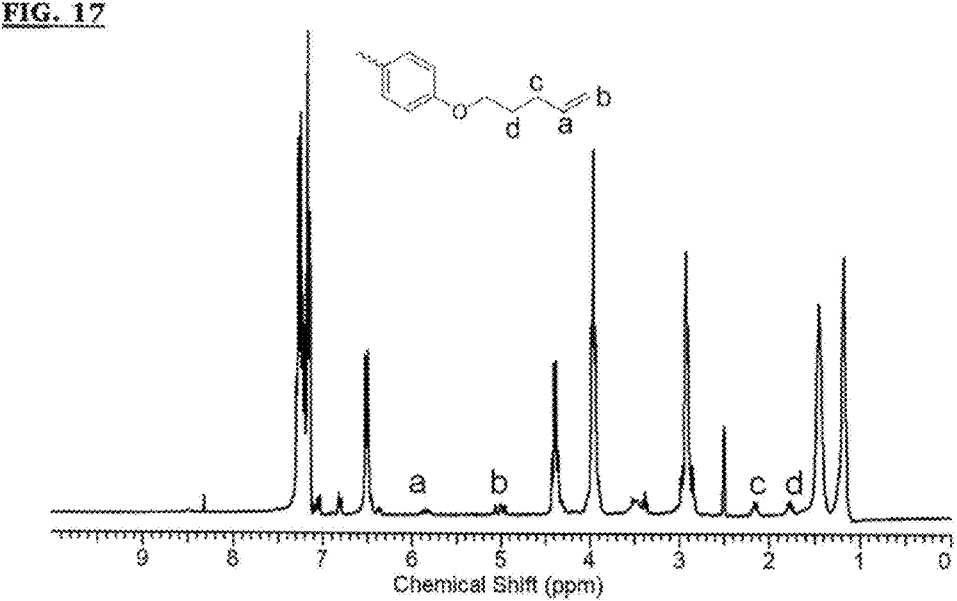
FIG. 17 is a $^1$H NMR of PEU-4 nanofibers.
Figure 18:
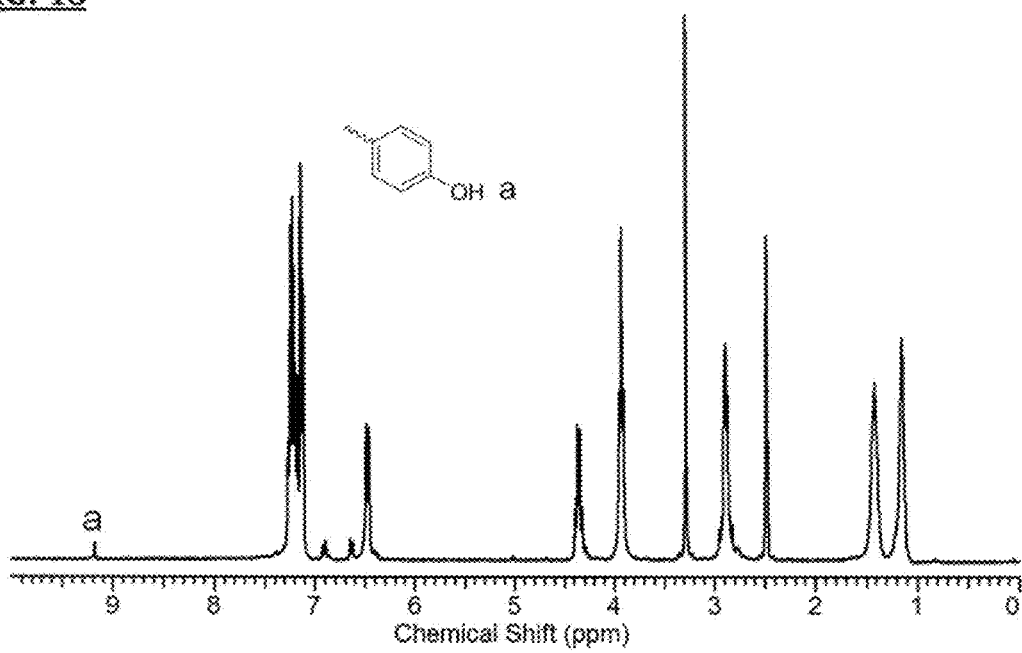
FIG. 18 is a $^1$H NMR of PEU-6 nanofibers.

$^1$H NMR spectroscopy confirmed the successful incorporation of the "clickable" groups into the PEUs. (See FIGS. 15-19). In FIG. 15, for example, the alkyne units in PEU-2 show characteristic peaks at 4.71 ppm and 3.52 ppm, and the chemical shifts of aromatic benzyl protecting group on the tyrosine are found at 6.77 ppm and 7.00 ppm, indicating incorporation of the alkyne group. FIG. 16 likewise demonstrates the incorporation of the azide group into PUE-3. The chemical shift of the methylene adjacent to the azide groups in PEU-3 is located at 3.46 ppm. The corresponding azide stretch peak is also observed at 2099 cm$^{-1}$ in the FT-IR spectra of PEU-3. And in FIG. 17, the existence of alkene groups in PEU-4 is verified by multi-split peaks at 5.80 and 5.00 ppm.

Figure 19:
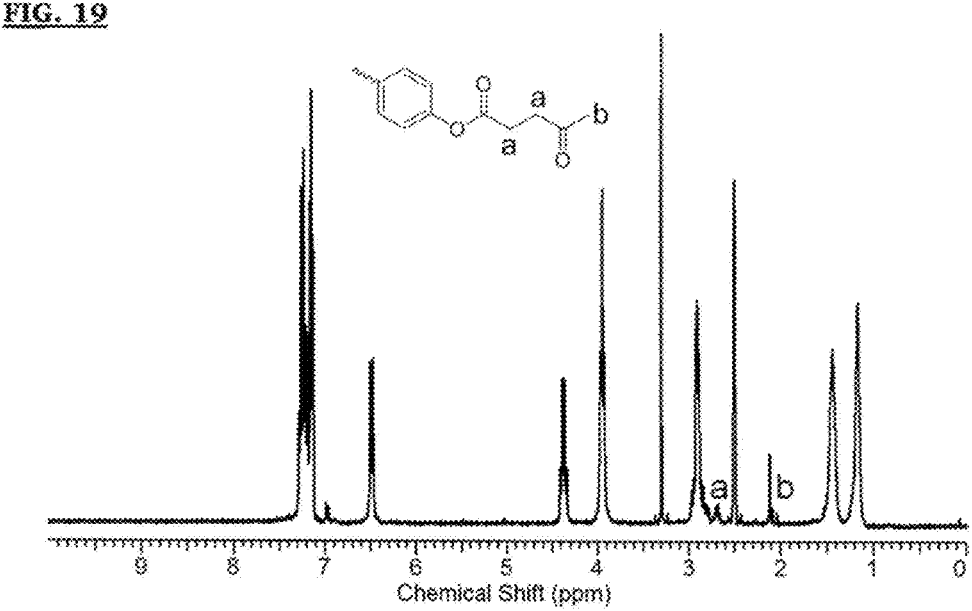
FIG. 19 is a $^1$H NMR of PEU-7 nanofibers.

In the PEU-6 spectra (FIG. 18), the hydroxyl group of tyrosine has a singlet at 9.20 ppm after the deprotection of the benzyl (Bzl) group in PEU-5, and the methylene of benzyl is no longer present. As set forth above, and shown in Scheme 2, PEU-7 (Keto-PEU) was prepared by the carbodiimide coupling between PEU-6 and levulinic acid. In FIG. 19, the single peak at 2.12 ppm is assigned to the methyl end group adjacent to the ketone, and the peak of phenolic hydroxyl group is not visible after esterification reaction. The existence of tyrosine units was verified by UV-Vis absorption.

The absorption curve of PEU-1 is flat in the 278 nm region, while others have a shoulder, which is the characteristic absorption of tyrosine. PEU-2 has a smaller absorption at 278 nm than the other functionalized PEUs, since the content of tyrosine units in PEU-2 is 2.5%, and in the other PEUs, it is 5%. The peak at 257 nm is assigned to the π-π absorption of phenylalanine.

By way of further example, a series of small molecules were chosen to verify the reactivities of PEU "clickable" groups for post-polymerization modification. (See Examples 11-13, 20). 3-azidopropan-1-ol was utilized for the derivation of PEU-2 through the CuAAC method. In FIG. 13A, the triazole proton signal is observed at 8.16 ppm and the methylene adjacent to the alkyne shifts from 4.72 ppm to 5.07 ppm after the alkyne-azide cycloaddition reaction. Peaks at 4.64 ppm and 1.93 ppm are assigned to the 3-azidopropan-1-ol protons. Propargyl alcohol was coupled to PEU-3 also through cycloaddition between alkyne and azide groups. In FIG. 13B, the triazole proton is found at 7.96 ppm and the methylene protons adjacent to the alkyne are located at 5.11 ppm. The methylene group protons adjacent to the azide shift from 3.44 ppm to 4.48 ppm. The success of propargyl alcohol coupling was furthered demonstrated via FT-IR spectroscopy, which indicated the complete conversion of the azide groups within the limits of FTIR detection.

Thiol-ene radical additions are also a well-established click process for both polymer and materials synthesis as there is no need for the metal catalyst and it is able to proceed at room temperature. In PEU-4, the alkene is incorporated as a pendent group for molecular grafting via a thiol-ene reaction. Mercaptopropionic acid was utilized to modify PEU-4 via photochemical thiol-ene addition in the presence of Irgacure-2959 photoinitiator. In FIG. 13C, after half an hour irradiation with 365 nm UV at room temperature, the signal corresponding to the alkene groups is not present. There is a new peak at 2.65 ppm, which is assigned to the methylene group adjacent to sulfur atom after the reaction.

PEU-6 with unprotected tyrosine units was synthesized for functionalization of polymers at the phenolic side chain with cyclic diazodicarboxamides, through an "ene"-type addition reaction. This reaction has emerged as a new type of "click" like reaction for the modification of small molecules, proteins, and peptides in aqueous environment. Compared to other kinds of reactive groups such as azide and alkyne, phenolic side chains of tyrosine are natural.

However, here there was no reaction observed between PEU-6 and alkyne-derived cyclic diazodicarboxamide (LXV) in organic solvent, when triethylamine (TEA) or N, N-diisopropylethylamine (DIPEA) was used as the base in the environment of DMF or DMSO. It should be appreciated that a strong base such as sodium hydride may be used to activate the phenol groups for ene-type addition in organic media. It has been found that the basicity of TEA (pKa 10.8) and DIPEA (pKa 11.4) is not sufficient for phenol activation in DMF or DMSO. Sodium hydride was not used, however, as it is believed that the PEU or any biomolecules would be destroyed. Due to harsh conditions, the application of the ene-type addition may be limited, especially when material modification would probably require an organic solvent. However, in the surface modification of PEU-6 nanofibers, the reactions occurred in a mixture of phosphate buffered saline (PBS buffer, pH 7.4) and acetonitrile (10:1 by volume). It is believed that this reaction may have potential application in polymer or scaffold modification in aqueous environments. In addition, the hydroxyl group of tyrosine units was still available for esterification, which was verified in the synthesis PEU-7 and allowed functionalization of polymers using carbodiimide coupling.

The oxime ligation, a condensation reaction between aldehyde or ketone groups and aminooxy groups, is a particularly attractive, facile and versatile for polymer modification. It occurs readily without major side reactions at room temperature, and the oxime bond is stable in physiological conditions and is widely used for protein conjugation, polymeric hydrogel fabrication and surface functionalization. Here, o-(pent-4-en-1-yl) hydroxylamine (LVI) was synthesized for derivation of ketone groups in PEU-7. In FIG. 13D, the protons of the methyl groups adjacent to the ketone shift from 2.12 ppm to 1.79 ppm following the imine formation and the characteristic peaks of alkene are observed at 5.00 ppm and 5.80 ppm.

These results demonstrate that alkyne, azide, alkene, phenol, and ketone groups of PEUs according to various embodiments of the present invention are available for the post-polymerization functionalization of these PEUs. Collectively the methods described herein provide a toolbox of various functional groups that may be utilized to tune PEU properties via highly efficient bio-orthogonal reactions, which occur without the use of extreme reaction conditions, solvents and reagents. Biomolecules such as peptides and proteins are readily attached to the PEU polymers utilizing CuAAC, thiol-ene addition or oxime ligation techniques, among others. It is believed that the conjugation of biomolecules to PEUs according to embodiments of the present invention can improve their stability in vitro and in vivo, and thus enhance their biological effects.

As set forth above, in some embodiments, nanofibers of the PEUs of the present invention may be prepared via electrospinning. The fabrication process is stable, continuous and well known. In some embodiments, diameters of the resulting nanofibers had a narrow distribution, varying from 350 nm to 500 nm (See FIGS. 20A-B). No differences were observed between the PEU homopolymer and the functionalized PEUs in the electrospinning process. The survival of the respective functional groups after electrospinning it was confirmed by $^1$H NMR spectra of the fiber mesh made from each of the derivatized polymers described above. (See FIGS. 15-19).

Figure 20:
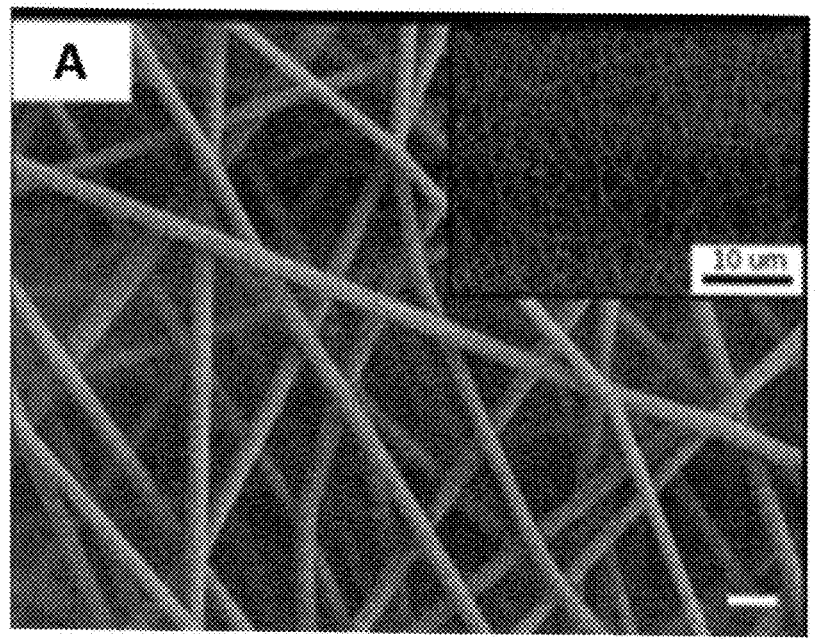
FIG. 20A-C (A) SEM micrograph of PEU nanofibers (scale bar 1 urn); (B) SEM picture of PEU nanofibers (scale bar 100 nm); (C) Stress-strain curve of PEU nanofiber matrices.
Figure 20:
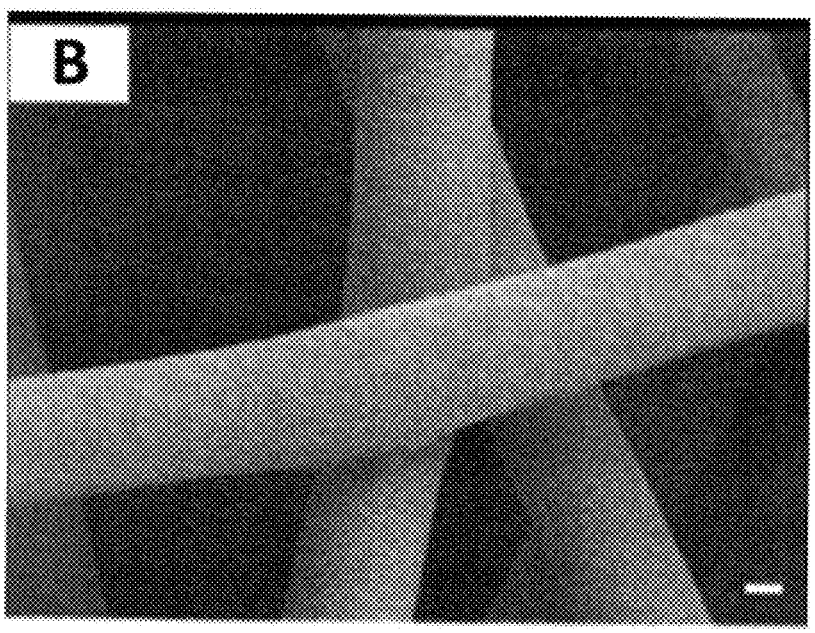
Figure 20:
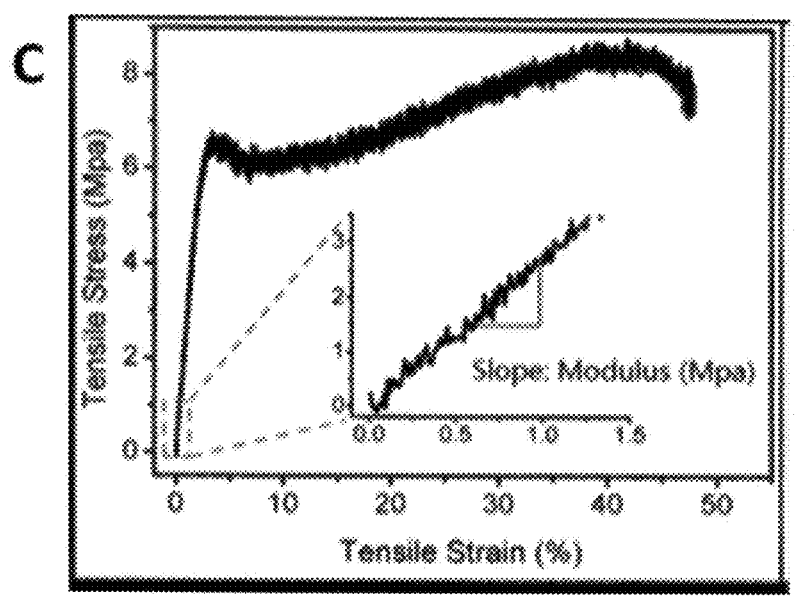

In addition, the mechanical properties of PEU fiber meshes according to embodiments of the present invention were characterized using universal tensile testing. In FIG. 20C, the Young's modulus of fiber matrix is 300±45 MPa in small strain region; the tensile strength is 8.5±1.2 MPa; and the tensile strain was 65±8% (n=3). In tissue engineering scaffolds, for example, the mechanical strength of the nanofiber meshes may be critical to the performance in vivo. As shown in Table 2, the mechanical strength of PEU nanofibers is comparable to that of PLGA when the diameter of fibers is around 500 nm. PEU nanofiber meshes have sufficient mechanical properties, meeting the requirements for some trabecular bones, cartilage and skin repairs.

TABLE 2

Comparison of tensile properties of nanofiber matrices: PEU, PCL, PLGA, gelatin, cartilage and skin. Nanofibers of PEU, PCL, PLGA, and gelatin are randomly oriented. PEU fibers' diameter: 350-500 nm; PCL and gelatin fibers' diameter: 10-1000 nm; PLGA fibers' diameter: 500-800 nm.

|  | PEU | PCL | PLGA | Gelatin | Cartilage | Skin |
| --- | --- | --- | --- | --- | --- | --- |
| Young's modulus (MPa) | 300 | 4.98 | 323 | 105 | 130 | 15-150 |
| Ultimate tensile stress (MPa) | 8.5 | 2.7 | 23 | 2.5 | 19 | 5-30 |
| Ultimate tensile strain (%) | 65 | 126 | 96 | 64 | 20-120 | 35-115 |

Figure 21:
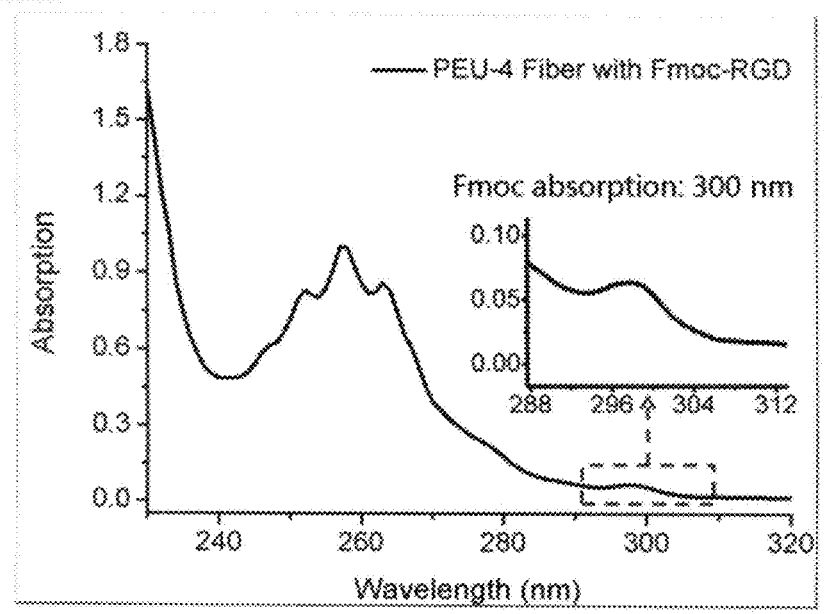
FIG. 21 is a graph showing the UV-Vis absorption of PEU-4 nanofibers after thiol-ene reaction with Fmoc-RGD-thiol.

The availability of "clickable" groups on the nanofiber surfaces was demonstrated using wet chemistry methods with fluorescence probes having complimentary reactive groups. In the embodiment shown in FIG. 12A, for example, Chromeo 488 azide was used for PEU-2 nanofiber labeling via CuAAC in PBS buffer solution. The color present on the nanofibers after reaction indicates the success of surface coupling. In the embodiment shown in FIG. 12B, alkyne-RGD-biotin was first coupled to PEU-3 fiber surface, followed by the incubation in aqueous environment containing rhodamine (TRITC)-conjugated streptavidin. It yielded fluorescent fiber matrices of PEU-3. In the embodiment shown in FIG. 12C, fluorescein-5-isothiocyanate (FITC)-conjugated RGD-thiol was tethered to PEU-4 fibers via thiol-ene radical addition reaction, yielding a fluorescence. Similarly, Fmoc-RGD-thiol was also used for PEU-4 nanofiber modification. Successful conjugation was verified by UV-Vis. Nanofibers after modification exhibited the Fmoc absorption peak at 300 nm in HFIP (FIG. 21), indicating the attachment of Fmoc-RGD-thiol to the fiber surface.

Figure 22:
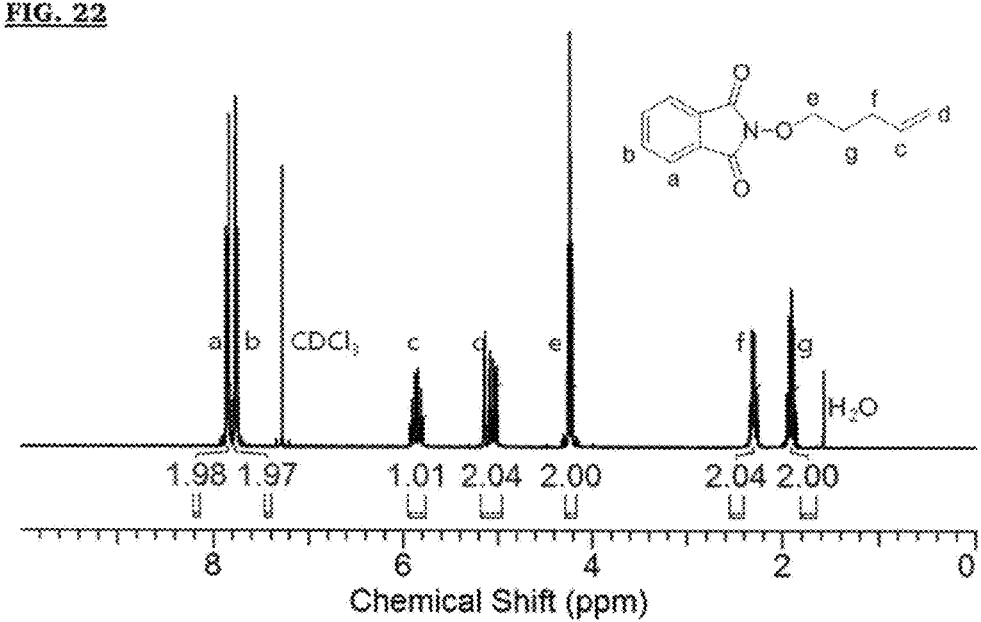
FIG. 22 is a $^1$H NMR (CDCl$_3$) spectrum of intermediate LV.

In some embodiments, the surface PEU-6 nanofibers were functionalized in an aqueous media. In these embodiments, an alkyne derived cyclic diazodicarboxamide (FIG. 22) was first covalently tethered to the fiber surface via ene-type reaction at the phenolic side chains of tyrosine, and then Chromeo 488 azide was conjugated to the nanofiber surface via CuAAC methods at surface available alkyne sites. (See FIG. 12D). The fluorescence indicates the successful modification of PEU-6 fiber surface via ene-type addition between tyrosine-phenol and cyclic diazodicarboxamide.

As to the PEU-7 fibers, the reactivities of the surface available ketone groups with both hydrazine and aminooxy were demonstrated. In these embodiments, Alexa fluor 568 hydrazide fluorescence was directly coupled to fiber surface via hydrazone bond formation and provided a red color (FIG. 12E). For oxime ligation, o-(prop-2-yn-1-yl)hydroxylamine (LIV) was utilized to conjugate to the fiber surface first, followed by the attachment of Chromeo 488 azide. A green fluorescence is yielded after the two-step derivation.

In all of the surface modification experiments described above, controls were conducted to exclude the physical absorption influence. See Example 20, below. Compared to the experimental groups, the fluorescence in all the controls was much weaker, which indicates that those fluorescent probes were actually attached to nanofiber surfaces via chemical reactions.

It has been demonstrated that "clickable" groups on the nanofiber surface of PEUs of embodiments of the present invention are chemically available for the bio-orthogonal conjugation of biologically active molecules. In that area of regenerative medicine, one of the major challenges is to design and fabricate degradable scaffolds with highly specific surface functional groups, which are able to promote cell attachment, proliferation and differentiation. In conventional methods for surface modification, plasma treatment is not efficient for modification of degradable polymers especially within a 3D porous structure, and most surface hydrolytic methods require extreme conditions. In this case, a number of bio-orthogonal "click" reactions may be utilized in the surface functionalization of nanofibers that facilitates the covalent attachment of biomolecules. The methods described herein provide a versatile and simple platform to precisely tune the surface properties of ECM like scaffolds in biological environment.

As set forth above, embodiments of the present invention are directed to highly functional tyrosine-based di-amine monomers and PEUs and the synthesis and uses thereof. In some embodiments, these monomers may be used to prepare high molecular mass PEUs using interfacial polycondensation methods. "Clickable" pendent groups, including, without limitation, alkyne, azide, alkene, tyrosine-phenol, and ketone, were incorporated into PEU polymers. Post-polymerization functionalization of PEU was accomplished via robust and efficient "click" type reactions. In some embodiments, PEU nanofiber matrices may be fabricated using electrospinning methods. As set forth above, the measured mechanical properties are in regimes useful for tissue engineering applications and the ability to chemically derivatize the surface of the nanofiber surfaces with peptides and fluorescent probes using bio-orthogonal reaction strategies will enable a number of translationally relevant constructs to be used in biomedical applications.

In light of the foregoing, it should be appreciated that the present invention significantly advances the art by providing highly functional tyrosine-based di-amine monomers and PEUs that are structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

All commercial chemicals and reagents were purchased from Sigma and Fisher Scientific, and used as received without further purification unless noticed otherwise. Chromeo 488 azide and Alexa fluor 568 hydrazide were purchased from Life Technologies (Carlsbad, Calif.). Rhodamine (TRITC)-conjugated streptavidin was purchased from Fisher Scientific (Pittsburgh, Pa.). Chloroform was distilled following drying overnight with $CaH_2$.

NMR spectra were obtained using a Varian NMR Spectrophotometer (300 MHz). All the chemical shifts are reported in ppm ($\delta$), and referenced to the chemical shifts of the residual solvent resonances ($^1$H NMR $CDCl_3$ 7.27 ppm, DMSO-$d_6$ 2.50 ppm, $D_2O$ 4.80 ppm; $^{13}$C $CDCl_3$ 77.00 ppm, DMSO-$d_6$ 39.50 ppm). The following abbreviations were used to explain the multiplicities: s=singlet, d=doublet, t=triplet, br=broad singlet, m=multiplet. FT-IR spectra were recorded using a MIRacle 10 ATR-FTIR (SHIMADZU Corp.). UV-Vis spectra were recorded using a Synergy™ Mx spectrophotometer (Biotek Inc.). Fluorescence microscopy images were recorded on an OLYMPUS IX 81 fluorescence microscope and are unaltered. The morphology of the nanofiber was characterized using field-emission scanning electron microscopy (SEM) (JSM-7401F, JEOL, Peabody, Mass.). The acceleration voltage for SEM imaging was 5.00 kV. Mechanical properties were recorded using an Instron 3365 under universal tensile testing conditions. Size exclusion chromatographic analyses (SEC) were performed using a TOSOH HLC-8320 SEC. N,N-dimethylformamide (DMF) with 0.01M LiBr was used as the eluent with a flow rate of 0.8 mL/min at 50° C. The molecular mass and mass distributions were calculated from polystyrene standards. Electrospray ionization (ESI) was performed using a HCT Ultra II quadripole ion trap mass spectrometer (Bruker Daltonics, Billerica, Mass.) equipped with an electrospray ionization source.

Example 1

Synthesis of Monomer of PEU-1 (M1)

The route used to synthesize the L-phenylalanine based monomer (M1) (for making PEU-1) is described in Scheme 4, and is reported in Stakleff, K. S.; Lin, F.; Smith Callahan, L. A.; Wade, M. B.; Esterle, A.; Miller, J.; Graham, M.; Becker, M. L. *Acta Biomaterialia* 2013, 9, 5132, the disclosure of which is encorporated herein by reference in its entirety.

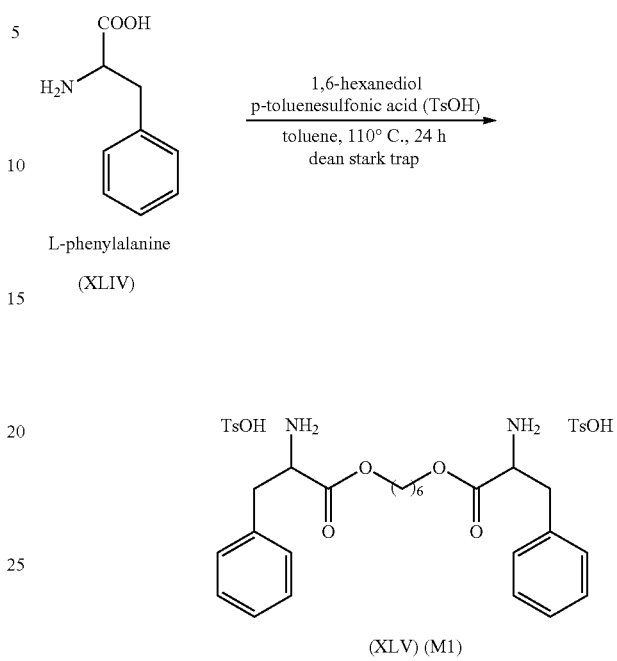

Scheme 4 shows the condensation of the L phenylalanine with the diol (in this case 1,6 hexane diol) to form compound (XLV) (M1). The TsOH acidifys the solution conditions preventing the amidation of the carboxylic acids. The protonated amino acid components was then heated at reflux at 110° C. in toluene to form the ester compounds. The Dean Stark trap was used to collect the water biproducts, increasing the yield of the reaction.

$^1$H NMR (300 MHz, DMSO-$d_6$): $\delta$=8.45 (br, 6H, $^+NH_3$—), 7.00-7.53 (m, 18H, aromatic), 4.30 (t, 2H, $^+NH_3CHCOO$—), 4.00 (t, 4H, —$COOCH_2CH_2$—), 2.90-3.25 (m, 4H, —$CHCH_2$—Ar), 2.29 (s, 6H, $CH_3Ar$—), 1.25-1.50 (br, 4H, —$COOCH_2CH_2CH_2$—), 0.95-1.15 (br, 4H, —$COOCH_2CH_2CH_2$—). See FIG. 2. $^{13}$C NMR (75 MHz, DMSO-$d_6$): $\delta$=169.1, 145.0, 138.2, 134.7, 129.4, 128.6, 128.3, 127.3, 125.6, 65.5, 53.4, 36.2, 27.7, 24.7, 20.8. See FIG. 3.

Example 2

Synthesis of Monomer of PEU-2 (M2)

The synthesis of alkyne-monomer (M2) for making PEU-2 was similar to the synthesis process of compound X (M1), except o-propargyltyrosine was used instead of L-phenylalanine. See Deiters, A.; Cropp, T. A.; Mukherji, M.; Chin, J. W.; Anderson, J. C.; Schultz, P. G. *Journal of the American Chemical Society* 2003, 125, 11782, the disclosure of which is encorporated herein by reference. The chemical formula for M2 is shown below.

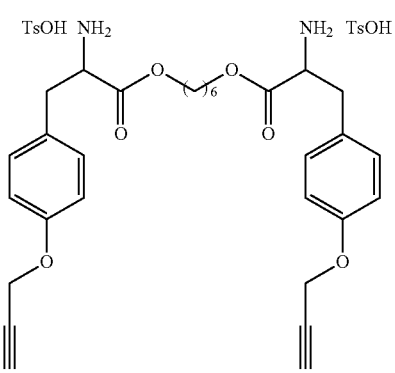

Compound XIV (M2) was purified by recrystallization with a mixture of water and ethanol (5:1, v/v) four times. The product came out as a white powder (yield 75%). $^1$H NMR (300 MHz, DMSO-$d_6$): δ=8.41 (s, 6H, $^+$NH$_3$—), 7.50 (d, 4H, aromatic), 7.10-7.20 (m, 8H, aromatic), 6.95 (d, 4H, aromatic), 4.76 (d, 4H, —OCH$_2$C≡CH), 4.23 (t, 2H, $^+$NH$_3$CHCOO—), 4.04 (t, 4H, —COOCH$_2$CH$_2$—), 3.55 (t, 2H, —OCH$_2$C≡CH), 2.90-3.25 (m, 4H, —CHCH$_2$—Ar), 2.29 (s, 6H, CH$_3$Ar—), 1.25-1.50 (br, 4H, —COOCH$_2$CH$_2$CH$_2$—), 0.95-1.15 (br, 4H, —COOCH$_2$CH$_2$CH$_2$—). See FIG. 4. $^{13}$C NMR (75 MHz, DMSO-$d_6$): δ=169.1, 156.5, 145.2, 138.0, 130.5, 128.2, 127.1, 125.5, 114.9, 79.3, 78.3, 65.5, 55.4, 53.3, 35.3, 27.7, 24.8, 20.8. See FIG. 5.

Example 3

Synthesis of Monomer of PEU-3 (M3)

The synthesis route for the azide-monomer used to make for PEU-3 (compound XV) (M3) is shown in Scheme 5, below. It was similar to that of S6 (M4), except that 3-azidopropyl 4-methylbenzenesulfonate was used instead of 5-Bromo-1-pentene. See, Mantovani, G.; Ladmiral, V.; Tao, L.; Haddleton, D. M. *Chemical Communications* 2005, 2089, the disclosure of which is hereby encorprated by reference.

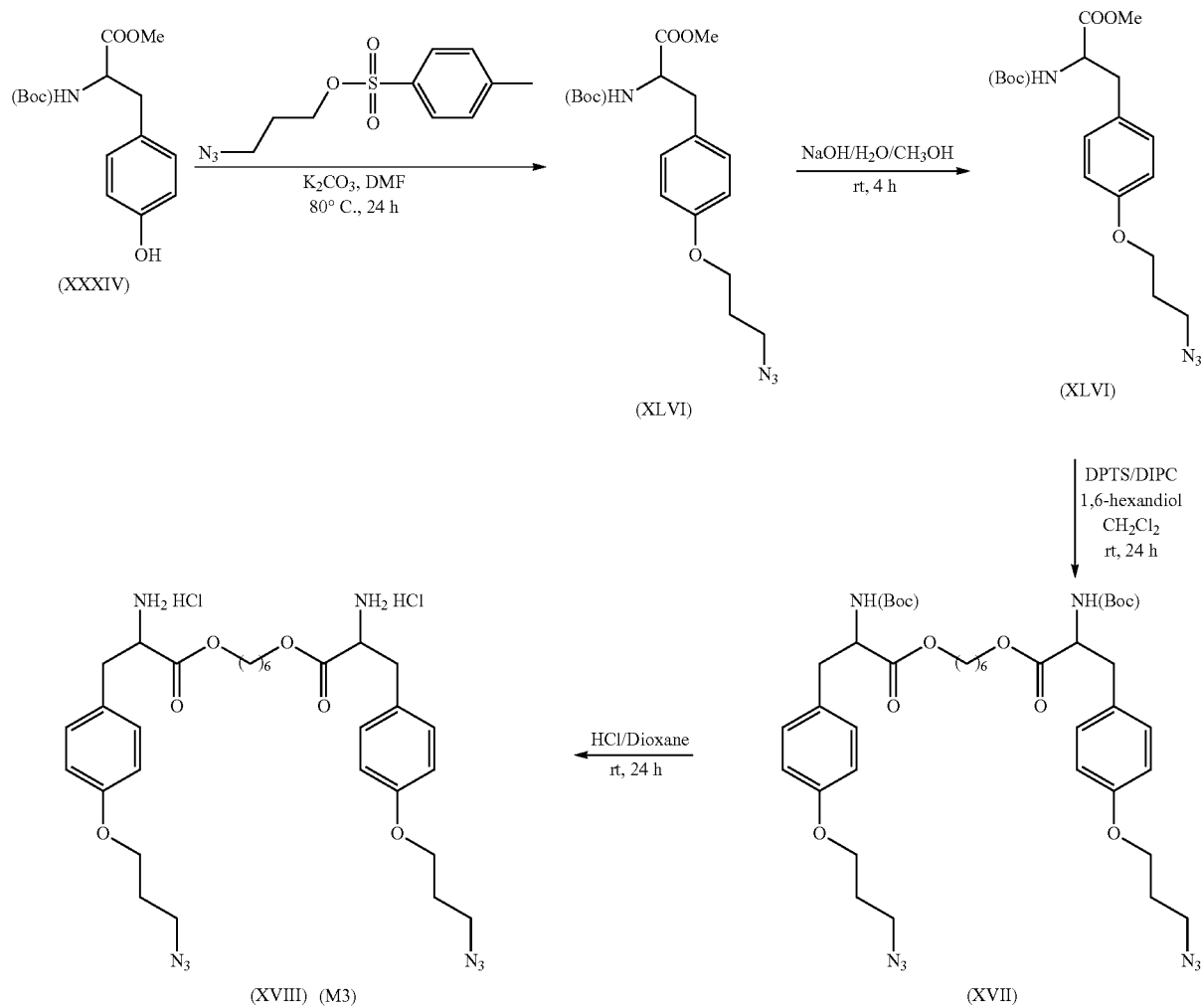

Compound XLVI was prepared by base catalyzed substitution of the Tosyl protected alkyl azide. The Boc and methyl ester protected tyrosine as dissolved in N,N-dimethylformamide and the tosyl protected alkyl azide was added in a stoichiometric ration. Potassium carbonate was added as a base and the reaction mixture was heated at 80 C for 24 hours under a blanket of inert gas. Compound XLVI: $^1$H NMR (300 MHz, CDCl$_3$): δ=6.95-7.15 (m, 2H), 6.75-6.90 (m, 2H), 4.96 (d, 1H), 4.45-4.65 (m, 1H), 4.03 (t, 2H), 3.52 (t, 2H), 2.95-3.12 (m, 2H), 1.97-2.10 (2H), 1.43 (s, 9H).

Compound XLVII was prepared by deprotecting the methyl ester of Compound XLVI using sodium hydroxide in a water/methanol solution at room temperature for 4 hours. Intermediate S7 was dissolved in a solution of methanol and water containing sodium hydroxide and stirred under an inert gas atmosphere at ambient temperature for 4 hours to remove the methyl protecting group producing intermediate compound XLVII. $^1$H NMR (300 MHz, CDCl$_3$): δ=8.50-10.00 (b, 1H), δ=7.02-7.15 (m, 2H), 6.75-6.90 (m, 2H), 4.96 (d, 1H), 4.45-4.65 (m, 1H), 4.03 (t, 2H), 3.52 (t, 2H), 2.95-3.25 (m, 2H), 1.97-2.10 (2H), 1.43 (s, 9H).

Compound XVII was prepared by condensation of the functional Boc-protected tyrosine with the diol (in this case 1,6 hexane diol). The TsOH acidifys the solution conditions preventing the amidation of the carboxylic acids. The protonated amino acid components are then heated at reflux in toluene to form the ester compounds. The Dean Stark trap was used to collect the water biproducts, increasing the yield of the reaction. This reaction was performed in methylene chloride at room temperature over 24 h. Compound XVII. $^1$H NMR (300 MHz, CDCl$_3$): δ=6.95-7.15 (m, 4H), 6.75-6.90 (m, 4H), 4.96 (d, 2H), 4.45-4.65 (m, 2H), 3.85-4.23 (m, 8H), 3.52 (t, 4H), 2.85-3.15 (m, 4H), 1.97-2.10 (4H), 1.20-1.75 (m, 26H).

PEU-3 Azide-monomer (Compound XVIII) (M3) was then prepared by removing the Boc protecting group from the amine using HCl in dioxane. $^1$H NMR (300 MHz, DMSO-d$_6$): δ=8.73 (s, 6H, $^+$NH$_3$—), 7.12 (d, 4H, aromatic), 6.84 (d, 4H, aromatic), 4.17 (t, 2H, $^+$NH$_3$CHCOO—), 3.80-4.10 (m, 8H, —CH$_2$CH$_2$N$_3$, —COOCH$_2$CH$_2$—), 3.50 (t, 4H, —CH$_2$CH$_2$N$_3$), 2.85-3.20 (m, 4H, —CHCH$_2$—Ar), 1.90-2.05 (m, 4H, —OCH$_2$CH$_2$CH$_2$N$_3$), 1.25-1.50 (br, 4H, —COOCH$_2$CH$_2$CH$_2$—), 0.95-1.15 (br, 4H, —COOCH$_2$CH$_2$CH$_2$—). See FIG. 6. $^{13}$C NMR (75 MHz, DMSO-d$_6$): δ=169.0, 157.6, 130.4, 126.5, 114.5, 65.3, 64.5, 53.3, 47.6, 35.2, 28.1, 27.6, 24.7. See FIG. 7.

Example 4

Synthesis of the Alkene-Monomer of PEU-4 (M4)

The route used to synthesize the alkene-monomer (M4) (for making PEU-4) is described in Scheme 6, below.

Scheme 6
The synthetic route of PEU-4 monomer (M4).

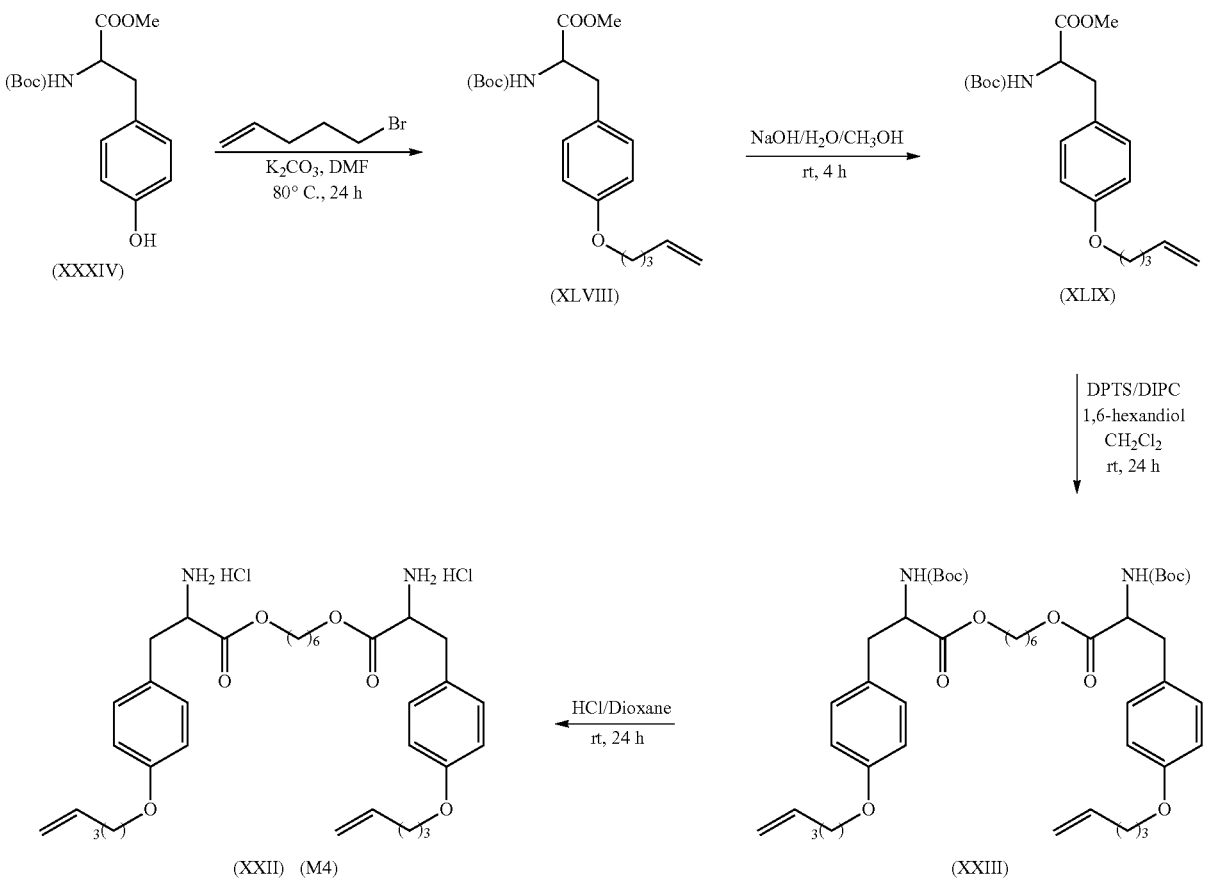

Intermediate compounds XLVIII and XLIX were prepared as described in Wang, Y.-S.; Fang, X.; Wallace, A. L.; Wu, B.; Liu, W. R. *Journal of the American Chemical Society* 2012, 134, 2950, the disclosure of which is hereby encorprated by reference. In short, intermediate compound XLVIII was prepared by the base activated substitution of the alkyl halide with the phenolic group. The Boc and methyl ester protected tyrosine as dissolved in N,N-dimethylformamide and the alkene functionalized alkyl halide was added in a stoichiometric ration. Potassium carbonate was added as a base and the reaction mixture was heated at 80 C for 24 hours under a blanket of inert gas. Compounds XLVIII. $^1$H NMR (300 MHz, CDCl$_3$): δ=6.95-7.15 (m, 2H), 6.75-6.92 (m, 2H), 5.75-5.95 (m, 1H), 4.85-5.15 (m, 3H), 4.45-4.65 (m, 1H), 3.95 (t, 2H), 3.72 (s, 3H), 2.85-3.15 (m, 2H), 2.18-2.30 (m, 2H), 1.80-1.95 (m, 2H), 1.42 (s, 9H).

Intermediate compound XLIX was prepared by deprotecting the methyl ester of Intermediate compound XLVIII using sodium hydroxide in a water/methanol solution at room temperature for 4 hours. Intermediate compound XLVIII was dissolved in a solution of methanol and water containing sodium hydroxide and stirred under an inert gas atmosphere at ambient temperature for 4 hours to remove the methyl protecting group. Intermediate compound XLIX. $^1$H NMR (300 MHz, CDCl$_3$): δ=8.95-10.10 (br, 1H), δ6.95-7.15 (m, 2H), 6.75-6.92 (m, 2H), 5.75-5.95 (m, 1H), 4.85-5.15 (m, 3H), 4.45-4.65 (m, 1H), 3.95 (t, 2H), 2.85-3.15 (m, 2H), 2.18-2.30 (m, 2H), 1.80-1.95 (m, 2H), 1.42 (s, 9H).

Intermediate compound XXIII was synthesized through the general esterification process. See Example 6, below. Intermediate compound XXIII. $^1$H NMR (300 MHz, DMSO-d$_6$): δ=8.31 (s, 2H), 7.15-7.25 (m, 2H), 7.05-7.15 (m, 4H), 6.75-6.90 (m, 4H), 5.55-5.95 (m, 2H), 4.90-5.10 (m, 4H), 3.80-4.15 (m, 10H), 2.65-2.95 (m, 4H), 2.10-2.23 (m, 4H), 1.68-1.85 (m, 4H), 1.10-1.60 (m, 26H).

Alkene-monomer XXII (M4) was obtained by the general procedure of Boc deprotection. See Example 7, below. PEU-4 monomer XXII (M4). $^1$H NMR (300 MHz, DMSO-d$_6$): δ=8.73 (s, 6H, $^+$NH$_3$—), 7.12 (d, 4H, aromatic), 6.84 (d, 4H, aromatic), 5.55-5.95 (m, 2H, —CH$_2$CH=CH$_2$), 4.90-5.10 (m, 4H, —CH$_2$CH=CH$_2$), 3.80-4.15 (m, 10H, $^+$NH$_3$CHCOO—, —COOCH$_2$CH$_2$—, —ArOCH$_2$CH$_2$—), 2.85-3.20 (m, 4H, —CHCH$_2$—Ar), 2.10-2.23 (m, 4H, —OCH$_2$CH$_2$CH$_2$CH=CH$_2$), 1.68-1.85 (m, 4H, —OCH$_2$CH$_2$CH$_2$CH=CH$_2$), 1.25-1.50 (br, 4H, —COOCH$_2$CH$_2$CH$_2$—), 0.95-1.15 (br, 4H, —COOCH$_2$CH$_2$CH$_2$—). See FIG. 8. $^{13}$C NMR (75 MHz, DMSO-d$_6$): δ=169.5, 158.3, 138.4, 130.9, 126.9, 115.7, 114.9, 67.2, 65.8, 53.8, 35.7, 30.1, 28.3, 28.1, 25.2. See FIG. 9.

Example 5

Synthesis of the Monomer of PEU-5 (M5)

The Benzyl (Bzl)-protected tyrosine monomer of PEU-5 (M5) was synthesized through the general esterification between Boc-O-benzyl-L-tyrosine and 1, 6-hexanediol, as shown below in Scheme 7, below.

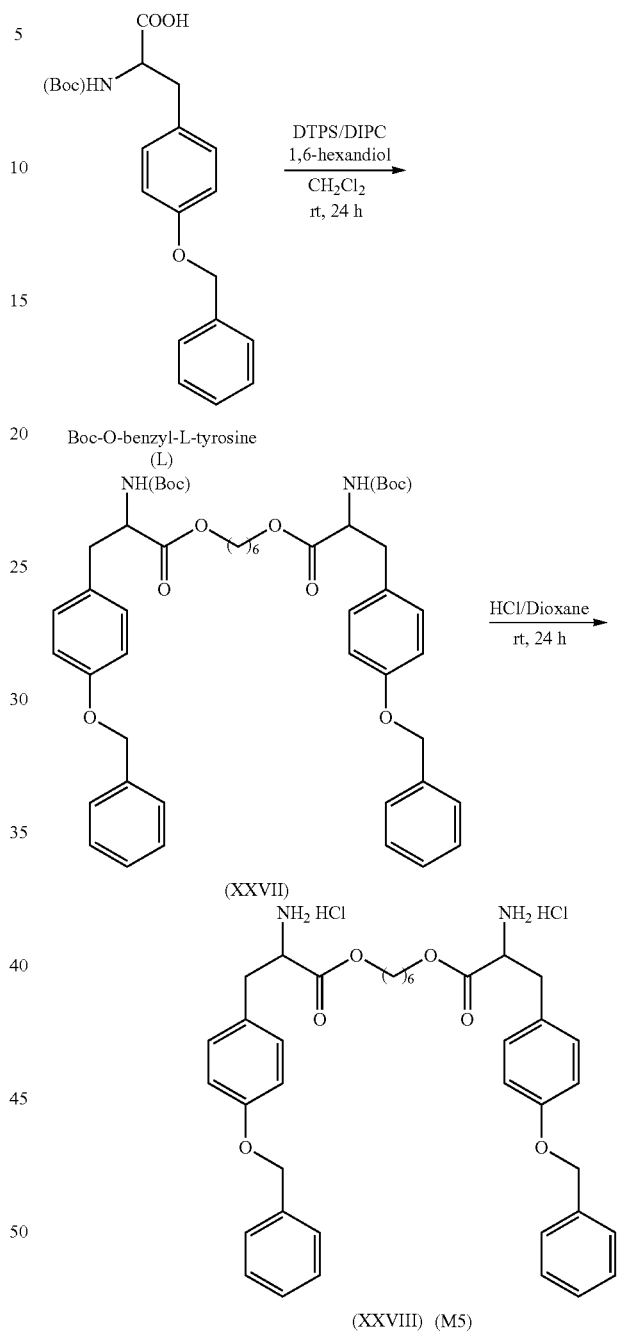

Scheme 7.
The synthetic route of PEU-5 monomer (M5).

Intermediate compound XXVII was prepared as set forth in Example 6, below. The Boc-O-benzyl-L-tyrosine reagent (L) was condensed onto both ends of the alkyl diol reagent using base (DPTS) and carbodiimide coupling reagents (DIPC) in methylene chloride. The reaction was stirred under an inert atmosphere at ambient temperature for 24 hours to yield the Boc protected Bis amino acid diester monomer (XXVII). Intermediate compound XXVII. $^1$H NMR (300 MHz, CDCl$_3$): δ=7.25-7.50 (m, 10H), 7.00-7.10 (m, 4H), 6.85-6.95 (m, 4H), 4.85-5.15 (m, 6H), 4.4-0-4.60 (m, 2H), 3.95-4.20 (m, 4H), 2.85-3.15 (m, 4H), 1.15-1.70 (m, 26H).

PEU-5 Benzyl (Bzl)-protected tyrosine monomer (XXVIII) (M5) was then prepared by see above. Removal of the Boc protecting group was accomplished by stirring intermediate compound XXVII in a solution of HCL in dioxane at ambient temperature for 24 h under and inert gas atmosphere. PEU-5 Benzyl (Bzl)-protected tyrosine monomer (XXVIII) (M5). $^1$H NMR (300 MHz, DMSO-$d_6$): δ=8.71 (br, 6H, $^+$NH$_3$—), 7.25-7.50 (m, 10H, benzyl unit aromatic), 7.10-7.20 (m, 4H, tyrosine unit aromatic), 6.85-7.00 (m, 4H, tyrosine unit aromatic), 5.06 (s, 4H, —Ar—OCH$_2$—Ar), 4.07-4.20 (m, 2H, $^+$NH$_3$CHCOO—), 4.01 (t, 4H, —COOCH$_2$CH$_2$—), 2.90-3.25 (m, 4H, —CHCH$_2$—Ar), 1.30-1.55 (m, 4H, —COOCH$_2$CH$_2$CH$_2$—), 1.10-1.25 (m, 4H, —COOCH$_2$CH$_2$CH$_2$—). See FIG. 10. $^{13}$C NMR (75 MHz, DMSO-$d_6$): δ=169.6, 158.0, 137.5, 131.0, 128.9, 128.0, 127.2, 115.2, 69.6, 66.8, 53.8, 35.6, 29.0, 28.3, 25.6. See FIG. 11.

Example 6

General Procedures of Carbodiimide Coupling Esterification

The reagent diol (1 eq.), acid (1.2 eq. per hydroxyl unit), and 4-(N,N-dimethylamino) pyridinium-4-toluenesulfonate (DPTS, 0.2 eq. per hydroxyl unit) were dissolved using a minimum amount of DMF. After set in ice bath for 10 min, 1,3-diisopropyl cabodiimide (DIPC, 1.5 eq. per hydroxyl unit) was added via syringe. The white precipitate was observed in minutes. The reaction was continuously stirred for 24 h. After filtration to remove the solid, the collected solution was concentrated for further purification.

Example 7

General Procedures for Tert-Butyloxycarbonyl (Boc) Deprotection

Boc-protected precursors (e.g. compound XXVII) were dissolved in HCl/dioxane (4M) solutions under nitrogen atmosphere. The reaction was continuously stirred for 24 h under nitrogen environment, followed by lyophilization to remove the organic solvent. The solid residue was further washed with diethyl ether twice and dried in vacuum, affording the desired product.

Example 8

General Procedures of Interfacial Polymerization

PEU-1, PEU-2, PEU-3, PEU-4 and PEU-5 were synthesized using the following procedure. Monomer (1 eq.) and sodium carbonate (3.5 eq.) were dissolved in 500 mL of water (0.1 M for monomer) in a 4-neck 2 L round bottom flask equipped with mechanical stirring. The cloudy solution was placed in a 35° C. water bath. After the temperature of the reaction solution reached 35° C., it was allowed to stir for an additional 30 min. The water bath was then removed and replaced with a brine-ice bath. When the reaction formulation temperature dropped to 0° C., a solution of triphosgene (0.6 M in chloroform, 1.1 eq.) was added within one minute with vigorous stirring. After 30 min of stirring, the cooling bath was removed. An additional aliquot of triphosgene solution (0.6 M, 0.1 eq.) was added drop-wise during over an additional 30 min period. The two phases were then separated. The organic phase containing the polymers was collected and washed with water twice. The collected organic phase was precipitated slowly into 3 L of hot water using mechanical stirring. After cooling to room temperature, pure polymer was obtained after filtration and drying.

PEU-1 (L-phenylalanine based PEU without functional groups). $^1$H NMR (300 MHz, DMSO-$d_6$): δ=7.00-7.40 (m, 10H, aromatic H), 6.40-6.55 (d, 2H, —NH—), 4.25-4.45 (m, 2H, —NHCHCOO—), 3.94 (t, 4H, —CHCOOCH$_2$—), 2.75-3.05 (m, 4H, —CHCH$_2$Ar), 1.30-1.60 (m, 4H, —COOCH$_2$CH$_2$CH$_2$—), 1.00-1.30 (m, 4H, —COOCH$_2$CH$_2$CH$_2$—). PEU-2, PEU-3, PEU-4, PEU-5, PEU-6, and PEU-7 possess NMR shifts corresponding to the L-phenylalanine units are identical as PEU-1. The chemical shifts of functionalized tyrosine units are described below.

PEU-2 (Alkyne-tyrosine units 2.5%): $^1$H NMR (300 MHz, DMSO-$d_6$): δ=7.00-7.10 (m, 4H, aromatic), 6.82-6.90 (m, 4H, aromatic), 4.71 (d, 4H, —OCH$_2$C≡CH), 3.52 (t, 2H, —OCH$_2$C≡CH). See FIG. 15.

PEU-3 (Azide-tyrosine units 5%): $^1$H NMR (300 MHz, DMSO-$d_6$): δ=7.00-7.10 (m, 4H, aromatic), 6.82-6.90 (m, 4H, aromatic), 4.12 (t, 4H, —OCH$_2$CH$_2$CH$_2$N$_3$), 3.44 (t, 4H, —OCH$_2$CH$_2$CH$_2$N$_3$), 1.93 (m, 4H, —OCH$_2$CH$_2$CH$_2$N$_3$). FT-IR (cm$^{-1}$): N$_3$ stretch 2099 cm$^{-1}$. See FIG. 16.

PEU-4 (Alkene-tyrosine units 5%): $^1$H NMR (300 MHz, DMSO-$d_6$): δ=7.00-7.10 (m, 4H, aromatic), 6.82-6.90 (m, 4H, aromatic), 5.75-5.95 (m, 2H, —CH$_2$CH=CH$_2$), 4.90-5.10 (m, 4H, —CH$_2$CH=CH$_2$), 2.05-2.25 (m, 4H, —OCH$_2$CH$_2$CH$_2$CH=CH$_2$), 1.65-1.85 (m, 4H, —OCH$_2$CH$_2$CH$_2$CH=CH$_2$). See FIG. 17.

The existence of PEU-5 (Benzyl protected tyrosine units 5%) was shown by $^1$H NMR (300 MHz, DMSO-$d_6$): δ=7.30-7.50 (shoulder, Bzl unit aromatic H), 7.00-7.10 (m, 4H, tyrosine unit aromatic), 6.82-6.90 (m, 4H, tyrosine unit aromatic), 5.03 (s, 4H, —ArOCH$_2$—Ar).

Example 9

Synthesis of Tyrosine-Phenol Derived Polymer (PEU-6)

PEU-5 (2.00 g, tyrosine units 5 mol %) was dissolved in DMF (20 mL), followed by the addition of palladium/carbon (0.20 g, 10 wt % of Pd). The suspension was stirred under hydrogen (60 PSI) at 50° C. for 24 h. The carbon was removed by filtration through Celite 545. The collected light brown solution was concentrated and precipitated into water. Pure polymer was obtained as a white solid after filtration and drying (1.75 g, yield 87%). Tyrosine unit $^1$H NMR (300 MHz, DMSO-$d_6$): δ=9.20 (s, 2H, —Ar—OH phenol), 6.85-6.98 (m, 4H, aromatic H), 6.60-6.70 (m, 4H, aromatic H). See FIG. 8.

Example 10

Synthesis of Ketone Derived Polymer (PEU-7)

PEU-6 (2.00 g) was dissolved in DMF (20 mL), followed by the addition of levulinic acid (1.2 eq. per phenol unit) and 4-(N,N-dimethylamino) pyridinium-4-toluenesulfonate (DPTS, 0.2 eq. per phenol unit). After cooling to 0° C., 1,3-diisopropyl cabodiimide (DIPC, 1.5 eq. per phenol unit) was added via syringe. The reaction mixture was allowed to warm up to ambient temperature and continuously stirred 24 h. Following precipitation into methanol, filtration and drying, the product PEU-7 was obtained as a white solid (1.70 g, yield 85%). Modified tyrosine unit $^1$H NMR (300 MHz, DMSO-$d_6$): δ=6.93-7.02 (m, 4H, aromatic), 2.75-2.85 (shoulder, —OOCCH$_2$CH$_2$COCH$_3$), 2.60-2.75 (m, 8H, —OOCCH$_2$CH$_2$COCH$_3$), 2.12 (s, 6H, —OOCCH$_2$CH$_2$COCH$_3$). See FIG. 19.

Example 11

General Procedures of Azide-Alkyne Huisgen Cycloaddition in Organic Solution Alkyne-PEU (PEU-2) was used to demonstrate the general nature of the methods. PEU-2 (2.00 g), 3-azidopropan-1-ol (2 eq. per alkyne unit) and PMDETA (20 uL) were dissolved in 20 mL DMF in a 100 mL schlenk flask under a argon atmosphere, followed by the addition of Cu$^I$Br (2 mg). Following three cycles of degassing, the reaction mixture was allowed to stir at 50° C. for 24 h. The copper salt was removed using neutral Al$_2$O$_3$ column chromatography. The collected light brown solution was concentrated and precipitated into water, yielding the desired triazole functionalized polymer as a white solid (1.68 g, yield 84%).

Modified tyrosine unit of PEU-2 after "click" reaction with 3-azidopropan-1-ol: $^1$H NMR (300 MHz, DMSO-$d_6$): δ=8.16 (s, 2H, triazole), 7.00-7.10 (m, 4H, aromatic), 6.82-6.90 (m, 4H, aromatic), 5.07 (s, 4H, —OCH$_2$-triazole), 4.64 (t, 4H, triazole-CH$_2$CH$_2$CH$_2$OH), 1.95 (m, 4H, triazole-CH$_2$CH$_2$CH$_2$OH). See FIG. 13A.

Modified tyrosine unit of PEU-3 after "click" reaction with propargyl alcohol: $^1$H NMR (300 MHz, DMSO-$d_6$): δ=7.96 (s, 2H, triazole), 5.12 (t, triazole-CH$_2$OH), 4.48 (m, 8H, —OCH$_2$CH$_2$CH$_2$-triaziol), 2.10-2.35 (m, 4H, —OCH$_2$CH$_2$CH$_2$-triaziol). FT-IR (cm$^{-1}$): N$_3$ stretch is not visible. See FIG. 13B.

Example 12

Functionalization of Alkene Polymer (PEU-4) Via Thiol-Ene Addition

PEU-4 (2.00 g), mercaptopropionic acid (5 eq. per alkene unit) and 1-2959 photo initiator (0.05 eq. per alkene unit) were dissolved in 20 mL DMF in a 100 mL beaker. The reaction mixture was irradiated using a hand-held UV lamp (365 nm, intensity 10 W/cm$^2$) for 30 min. The polymer solution was precipitated into methanol, yielding the desired thiol-functionalized polymer as a white solid (1.72 g, yield 86%). The modified tyrosine unit of PEU-4 after thiol-ene addition with mercaptopropionic acid $^1$H NMR (300 MHz, DMSO-$d_6$): δ=7.00-7.10 (m, 4H, aromatic), 6.82-6.90 (m, 4H, aromatic), 2.65 (t, 4H, —CH$_2$CH$_2$SCH$_2$COOH), 1.50-1.75 (shoulder, —OCH$_2$CH$_2$CH$_2$CH$_2$S—). See FIG. 13C.

Example 13

Functionalization of Ketone Polymer (PEU-7) Via Oxime Ligation

PEU-7 (2.00 g) was dissolved in DMF (20 mL). O-(pent-4-en-1-yl) hydroxylamine (compound LVI, 1.2 eq. to ketone unit), triethylamine (1.2 eq. to ketone unit) and p-toluenesulfonic acid (5 mg) were added into the polymer solution. After overnight stirring at room temperature, polymer solution was precipitated into methanol, yielding the desired oxime product polymer as a white solid (1.72 g, yield 86%). In the $^1$H NMR spectra, there were no changes in the L-phenylalanine monomer units. Special details of the L-tyrosine units are listed below. Modified tyrosine unit of PEU-7 after oxime-ligation with O-(pent-4-en-1-yl)hydroxylamine (LVI): $^1$H NMR (300 MHz, DMSO-$d_6$): δ=6.93-7.02 (m, 4H, aromatic), 5.75-5.95 (m, 2H, —CH$_2$CH=CH$_2$), 4.90-5.10 (m, 4H, —CH$_2$CH=CH$_2$), —OOCCH$_2$CH$_2$COCH$_3$), 1.97-2.12 (m, 4H, —OCH$_2$CH$_2$CH$_2$CH=CH$_2$), 1.79 (s, 6H, —OOCCH$_2$CH$_2$C(=N—)CH$_3$), 1.55-1.70 (m, 4H, —OCH$_2$CH$_2$CH$_2$CH=CH$_2$). See FIG. 13D.

Example 14

Peptide Synthesis

Figure 23:
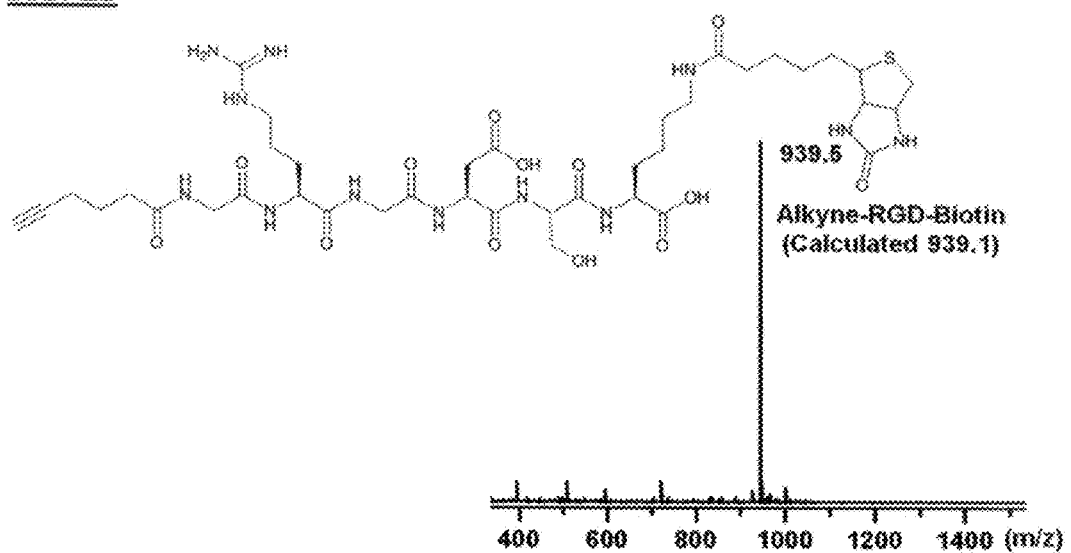
FIG. 23 is an ESI spectrum of alkyne-RGD-biotin.
Figure 24:
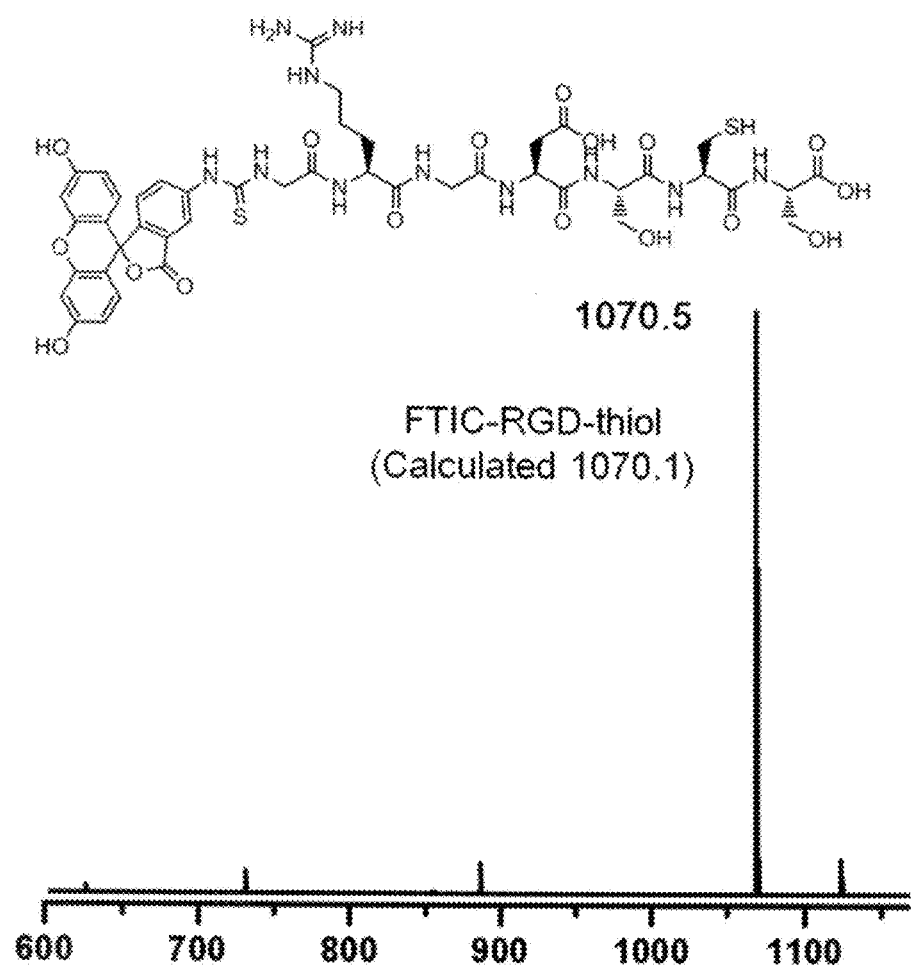
FIG. 24 is a MALDI spectrum of FITC-RGD-thiol.
Figure 25:
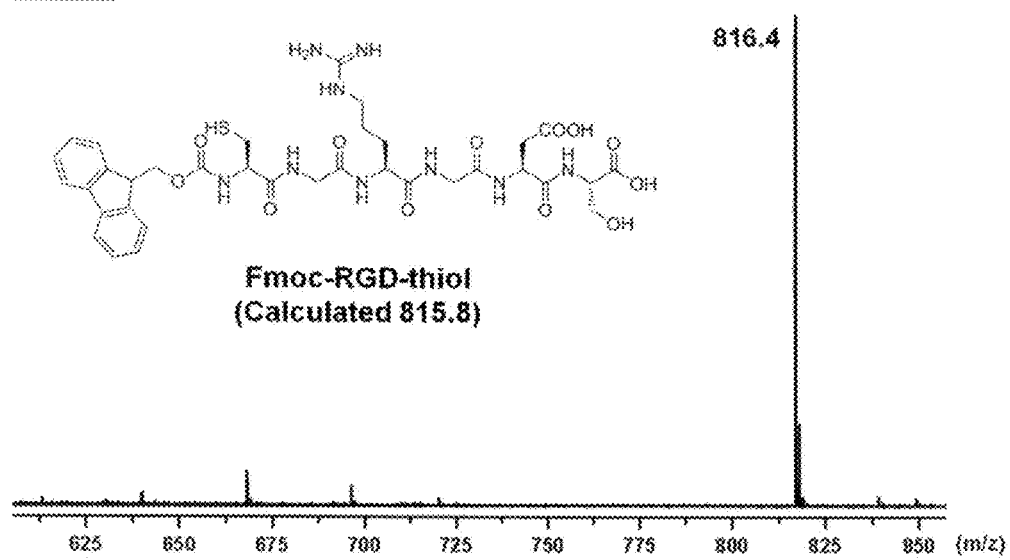
FIG. 25 is a MALDI spectrum of Fmoc-RGD-thiol.

Three peptides bearing "clickable" groups were synthesized by standard solid phase FMOC methodology using a CEM automatic microwave synthesis instrument. Peptides were cleaved from the resin using standard conditions (45 min, 95% trifluoroacetic acid (TFA), 2.5% triisopropylsilane (TIPS), 2.5% water (by volume)) and precipitated in cold diethyl ether. The crude solid product was isolated by centrifugation, washed twice with diethyl ether and dialyzed in deionized water (molecular weight cut off (MWCO) 500 g/mol, cellulose, Pierce), followed by lyophilization. For alkyne-GRGDSK(Biotin)-COOH), 5-hexynoic acid was coupled to N-terminus using standard coupling conditions prior to cleavage. For fluorescein-5(6)-isothiocyanate (FITC)-RGD-thiol (sequence FITC-GRGDSCS), FITC (Sigma) was coupled to the N-terminus in DMF overnight prior to cleavage.[61,62] For Fmoc-RGD-thiol (sequence Fmoc-CGRGDS), after the coupling of a cysteine residue at the N-terminus, the peptide was directly cleaved without the deprotection of Fmoc groups. The chemical structures and purity of the peptides and conjugates were confirmed by mass spectroscopy. ESI: Alkyne-RGD-Biotin calculated 939.1, measured 939.5; MALDI: FITC-RGD-thiol calculated 1070.1, measured 1070.5; Fmoc-RGD-thiol calculated 815.8, measured 816.4. FITC-RGD-thiol exhibited an excitation peak at 492 nm, and an emission peak at 512 nm in PBS buffer. The absorption maxima peak of Fmoc-RGD-thiol was 300 nm in PBS buffer. See FIGS. 23-25.

Example 15

Nanofiber Fabrication Via Electrospinning

PEU was dissolved in hexafluoroisopropanol (HFIP) (10 wt %). The jet was fabricated by pulling a torch-heated PTFE container terminal equipped with stainless metal needle of 25 gauge. The flow rate was controlled at 1 mL/h via a gas pump. A voltage of 12 kV was used and the aluminum foil collector was grounded. The distance between needle and collector was controlled at 25 cm. (See FIGS. 6A-B).

Example 16

Mechanical Testing of Nanofiber Matrix

The Young's modulus and tensile properties of a PEU nanofiber matrix were measured using universal tensile testing on an Instron 3365. The gauge length was 30 mm and the crosshead speed was set at 3 mm/min. The specimens were 50 mm long, 4 mm wide and 0.01 mm thick. The Young's modulus was calculated using the slope of tangent line of the stress-strain curve in small strain region (1%).

The results presented are average values for three individual measurements. (See FIG. 6C).

Example 17

Synthesis of Ketone Probe o-(prop-2-yn-1-yl)hydroxylamine

Ketone probe O-(prop-2-yn-1-yl) hydroxylamine (LIV) was synthesized as shown in Scheme 8, below and as described in Lin, F.; Zheng, J.; Yu, J.; Zhou, J.; Becker, M. L. *Biomacromolecules* 2013, 14, 2857, the disclosure of which is hereby encorprated by reference in its entirety.

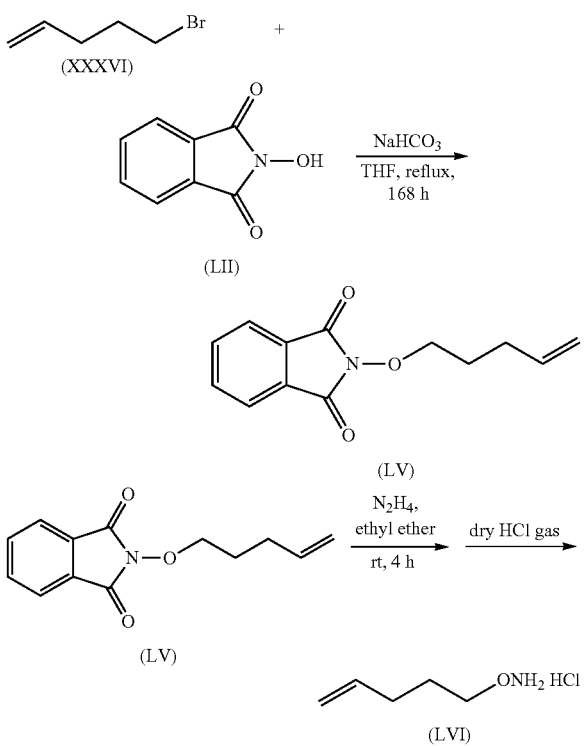

Intermediate compound (LIII) was prepared by reacting propargyl bromide with N-hydroxyphthalamide in a solution of tetrahydrofuran containing sodium bicarbonate at 80 C for 18 hours under an inert gas atmosphere. Intermediate compound (LIII): $^1$H NMR (300 MHz, CDCl$_3$): 7.73-7.95 (m, 4H, aromatic), 4.89 (d, 2H, —OCH$_2$C≡CH), δ=2.60 (t, 1H, —OCH$_2$C≡CH).

Figure 26:
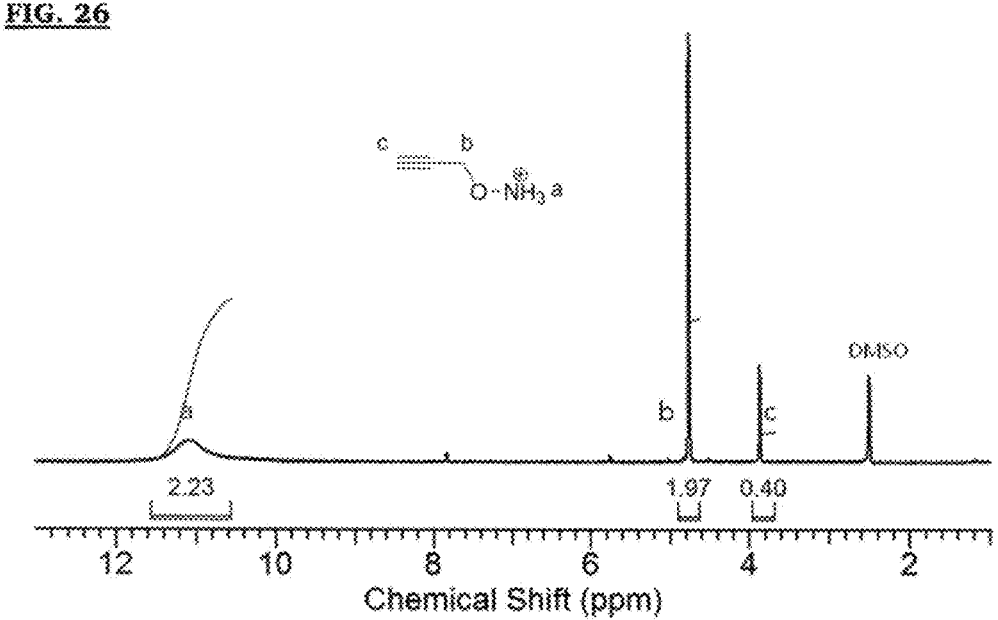
FIG. 26 is a $^1$H NMR (DMSO-$d_6$) spectrum of intermediate LIV.
Figure 27:
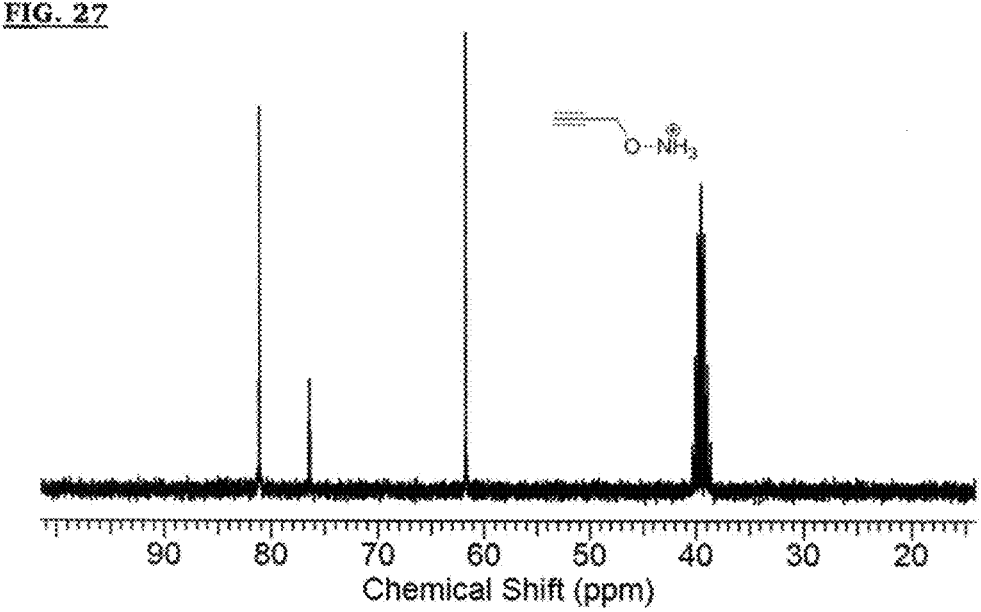
FIG. 27 is a $^{13}$C NMR (DMSO-$d_6$) spectrum of intermediate LIV.

O-(prop-2-yn-1-yl)hydroxylamine (LIV) was then prepared by removing the 1,2 compound by dissolving intermediate compound (LIII) in a solution of hydrazine in diethyl ether and stirring for 4 hours at ambient temperature under and inert gas atmosphere. O-(prop-2-yn-1-yl)hydroxylamine (LIV): $^1$H NMR (300M Hz, DMSO-d$_6$): δ=11.10 (br, 3H, $^+$NH$_3$O—), 4.75 (m, 2H, —OCH$_2$C≡CH), 3.87 (m, 1H, —OCH$_2$C≡CH). See FIG. 26. $^{13}$C NMR (75 MHz, DMSO-d$_6$): δ=81.1, 76.5, 61.7. See FIG. 27.

Example 18

Synthesis of O-(pent-4-en-1-yl)hydroxylamine (LVI)

The synthetic process of ketone group O-(pent-4-en-1-yl) hydroxylamine (LVI) is shown in Scheme 9 below and was similar to that of intermediate compound LIV, except that 5-Bromo-1-pentene was used instead of propargyl bromide.

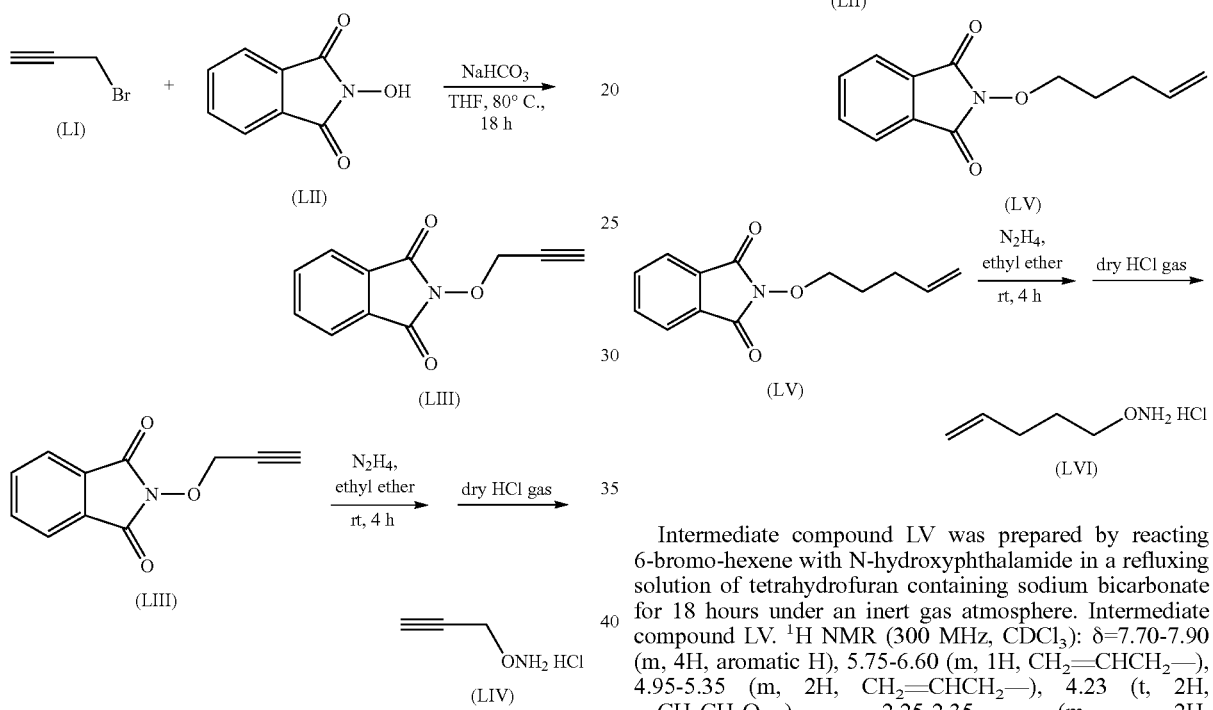

Intermediate compound LV was prepared by reacting 6-bromo-hexene with N-hydroxyphthalamide in a refluxing solution of tetrahydrofuran containing sodium bicarbonate for 18 hours under an inert gas atmosphere. Intermediate compound LV. $^1$H NMR (300 MHz, CDCl$_3$): δ=7.70-7.90 (m, 4H, aromatic H), 5.75-6.60 (m, 1H, CH$_2$=CHCH$_2$—), 4.95-5.35 (m, 2H, CH$_2$=CHCH$_2$—), 4.23 (t, 2H, —CH$_2$CH$_2$O—), 2.25-2.35 (m, 2H, CH$_2$=CHCH$_2$CH$_2$CH$_2$O—), 1.83-1.97 (m, 2H, CH$_2$=CHCH$_2$CH$_2$CH$_2$O—).

Figure 28:
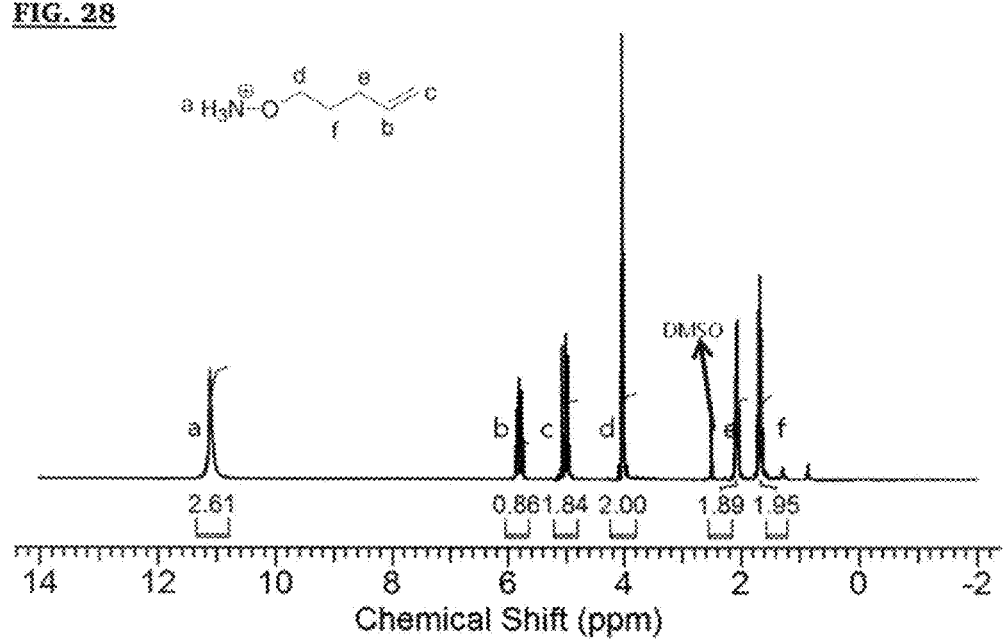
FIG. 28 is a $^1$H NMR (DMSO-$d_6$) spectrum of intermediate LVI.
Figure 29:
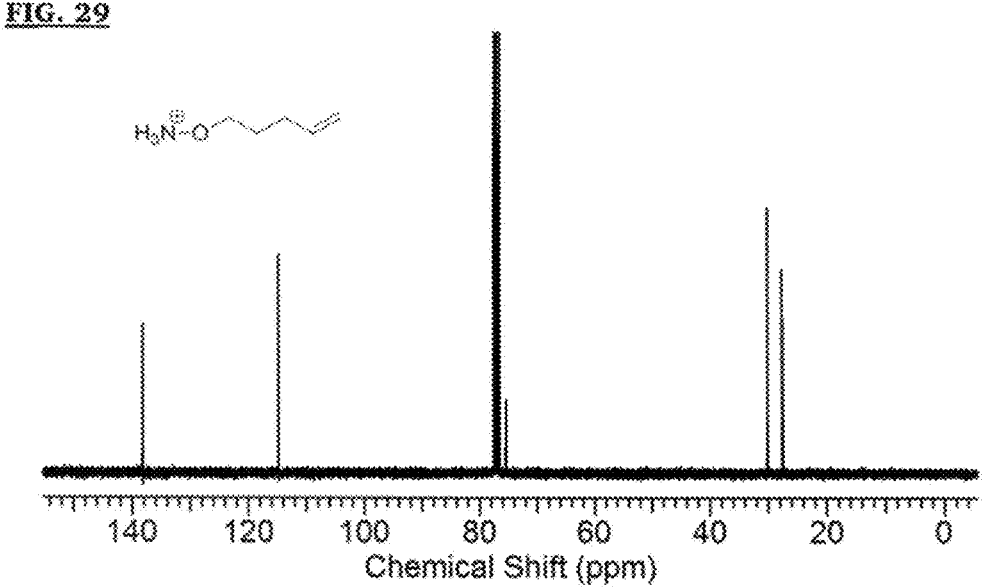
FIG. 29 is a $^{13}$C NMR (DMSO-$d_6$) spectrum of intermediate LVI.

Ketone binding group O-(pent-4-en-1-yl)hydroxylamine (LVI) was then prepared by removing the 1,2 compound by dissolving intermediate compound LV in a solution of hydrazine in diethyl ether and stirring for 4 hours at ambient temperature under and inert gas atmosphere. The solution was then neutralized with by bubbling with dry HCl gas. O-(pent-4-en-1-yl)hydroxylamine LVI. $^1$H NMR (300 MHz, DMSO-d$_6$): δ=11.11 (br, 3H, $^+$NH$_3$O—), 5.75-6.60 (m, 1H, CH$_2$=CHCH$_2$—), 4.95-5.35 (m, 2H, CH$_2$=CHCH$_2$—), 4.02 (t, 2H, —CH$_2$CH$_2$O—), 1.95-2.15 (m, 2H, CH$_2$=CHCH$_2$CH$_2$CH$_2$O—), 1.55-1.75 (m, 2H, CH$_2$=CHCH$_2$CH$_2$CH$_2$O—). See FIG. 28. $^{13}$C NMR (75 MHz, DMSO-d$_6$): δ=136.5, 115.4, 73.4, 29.2, 26.4. See FIG. 29.

Example 19

Synthesis of Alkyne Derived Cyclic Diazodicarboxamide for Tyrosine Coupling The synthetic route of the alkyne derived cyclic diazodicarboxamide (LXV) is shown in Scheme 10 below and described in Ban, H.; Gavrilyuk, J.; Barbas, C. F. *Journal of the American Chemical Society* 2010, 132, 1523 and Ban, H.; Nagano, M.; Gavrilyuk, J.; Hakamata, W.; Inokuma, T.; Barbas, C. F. *Bioconjugate Chemistry* 2013, 24, 520, the disclosure of which are encorporated herein by reference in their entirety.

ecarboxylate (0.5 g, 5 mmol, 1. eq.) and 1,1'-carbonyldiimidazole (0.89 g, 5.5 mol, 1.1 eq.) were dissolved in 30 mL anhydrous CHCl$_3$ and stirred for 2 h at room temperature. Intermediate compound (LIX) (0.9 g, 5 mmol, 1 eq.) and triethylamine (1.4 ml, 10 mmol, 2 eq.) were added into the reaction mixture and stirred overnight. After diluted with 50

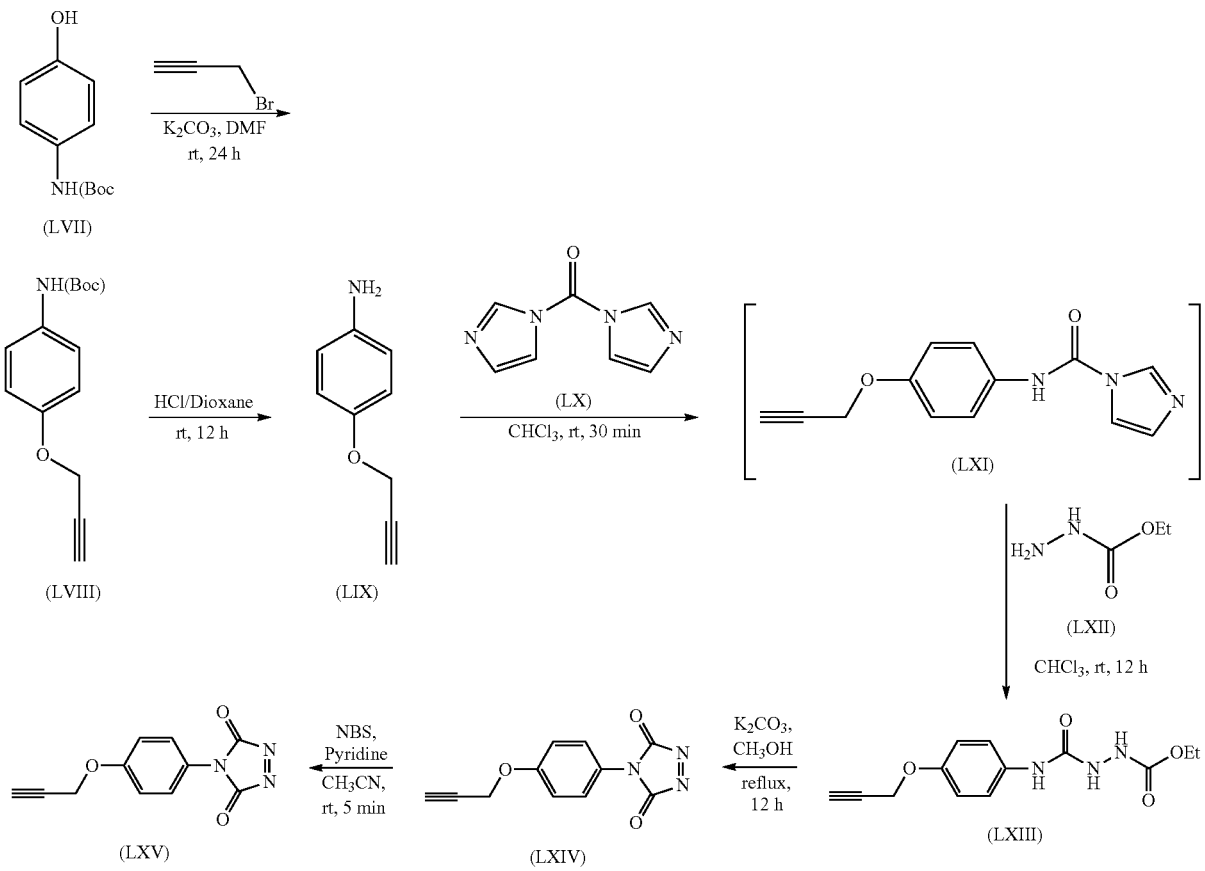

Scheme 10
The synthetic route of alkyne derived cyclic diazodicarboxamide (LXV)

Intermediate compound LVIII was synthesized as shown above and as follows. N-Boc-4-hydroxyaniline (2.0 g, 10 mmol, 1 eq.) and K$_2$CO$_3$ (2.0 g, 15 mmol, 1.5 eq.) were added into 50 mL DMF, followed by the addition of propargyl bromide (2.3 g, 15 mmol, 1.5 eq.) drop by drop. The resulted suspension was allowed to stir at room temperature for 24 h. The solid residue was removed by filtration. The collected organic solution was concentrated for further column chromatography purification on silica gel. The product was afforded as a whit solid. (2.1 g, yield 85%). Intermediate compound LVIII $^1$H NMR (300M Hz, DMSO-d$_6$): δ=9.15 (s, 1H, —NH), 7.25-7.45 (m, 2H, aromatic), 6.80-6.92 (m, 2H, aromatic), 4.70 (d, 2H, —OCH$_2$C≡CH), 3.52 (t, 1H, —OCH$_2$C≡CH), 1.44 (s, 9H, (CH$_3$)$_3$CCO—).

Intermediate compound LIX was prepared from Intermediate compound LVIII after the deprotection of Boc groups as described above. Compound LIX $^1$H NMR (300M Hz, DMSO-d$_6$): δ=10.36 (s, 3H, $^+$NH$_3$—), 7.30-7.40 (m, 2H, aromatic), 7.00-7.13 (m, 2H, aromatic), 4.81 (d, 2H, —OCH$_2$C≡CH), 3.60 (t, 1H, —OCH$_2$C≡CH).

Intermediate compound LXIII was synthesized as shown above and as follows. In a 100 mL flask, ethyl hydrazinmL CHCl$_3$, the organic solution was washed with 1 M HCl solution three times followed by water washing twice. The organic layer was collected and dried with MgSO$_4$. After removal of all the organic solvent, the product came out as a light brown solid. It was used directly for the next step without further purification (1.1 g, yield 78%). Intermediate compound LXIII $^1$H NMR (300M Hz, DMSO-d$_6$): δ=8.86 (s, 1H, —ArNHCONHNHCO—), 8.54 (s, 1H, —ArNHCONHNHCO—), 7.90 (s, 1H, —ArNHCONHNHCO—), 7.30-7.40 (m, 2H, aromatic), 6.83-6.95 (m, 2H, aromatic), 4.72 (d, 2H, —OCH$_2$C≡CH), 4.00-4.12 (m, 2H, —NHCOOCH$_2$CH$_3$), 3.51 (t, 1H, —OCH$_2$C≡CH), 1.19 (t, 3H, —NHCOOCH$_2$CH$_3$).

Figure 30:
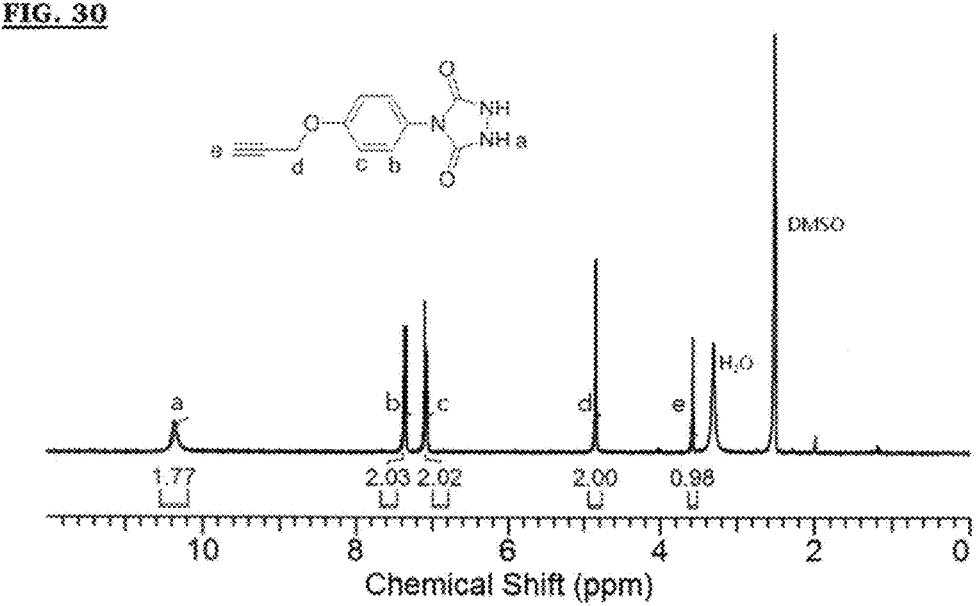
FIG. 30 is a $^1$H NMR (DMSO-$d_6$) spectrum of intermediate LXIV.
Figure 31:
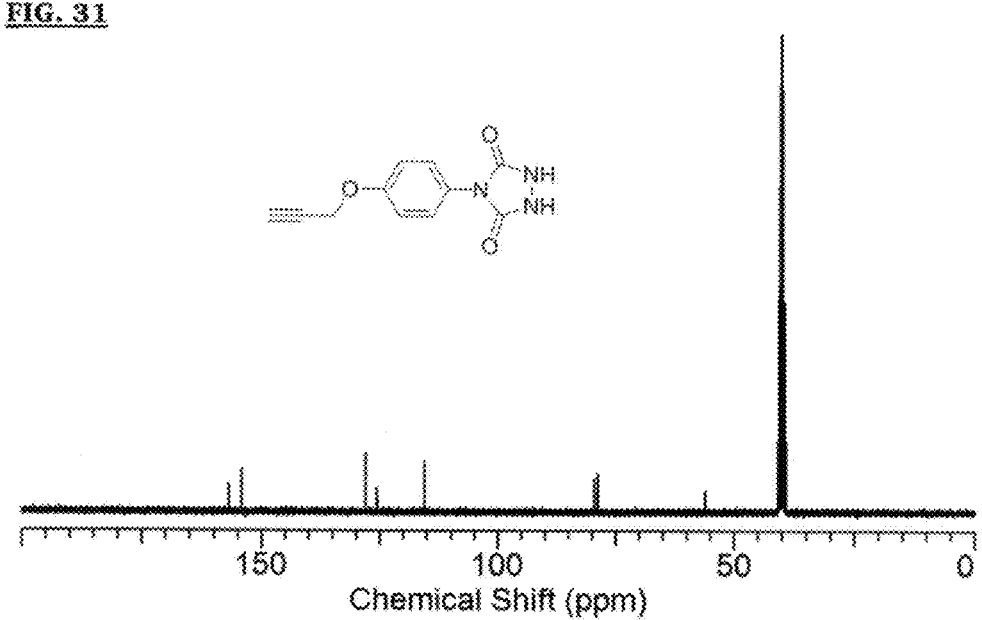
FIG. 31 is a $^{13}$C NMR (DMSO-$d_6$) spectrum of intermediate LXIV.

Intermediate compound LXIV was synthesized as shown above and as follows. Intermediate compound LXIII (1.0 g, 3.6 mmol, 1 eq.) was dissolved in 30 mL methanol, followed by the addition of K$_2$CO$_3$ (1.0 g, 7.2 mmol, eq.) This suspension was allowed to reflux overnight. The reaction mixture was acidified to the pH of 2 with 12 N HCl. Solid residue was filtered off. After the removal of solvent, the solid residue was purified using column chromatography on silica gel with ethyl acetate as elute. The product came out as white solid. (0.38 g, yield 45%). Intermediate compound LXIV $^1$H NMR (300M Hz, DMSO-d$_6$): δ=10.36 (s, 2H, —NHNH—), 7.30-7.43 (m, 2H, aromatic), 7.03-7.15 (m, 2H, aromatic), 4.83 (d, 2H, —OCH$_2$C≡CH), 3.57 (t, 1H, —OCH$_2$C≡CH). See FIG. 30. $^{13}$C NMR (75 MHz, DMSO-d$_6$): δ=156.8, 154.1, 128.0, 125.6, 115.5, 79.5, 78.8, 56.1. See FIG. 31.

In a 20 mL vial, intermediate compound LXIV (23 mg, 10 mmol, 1 eq.) and pyridine (8 uL, 10 mmol, 1 eq.) were dissolve in 3 mL CH$_3$CN, followed by the addition of N-bromosuccinimide (17.8 mg, 10 mmol, 1 eq.). The reaction mixture was allowed to stir at room temperature for 5 min, and directly used for the next step without further purification. In all experiments, compound LXV was freshly made for use.

Example 20

Surface Modification of Nanofibers Via Wet Chemistry

A series of fluorescent probes were used to visualize the nanofiber surface functionalization. Nanofibers were deposited on glass slides for surface wet chemistry in all experiments. A summary of the individual reaction formulations for both the experimental groups and control groups are listed in Table 3, below.

TABLE 3

Reaction formulation summary of experiment groups and control groups for nanofiber surface modification.

| Polymer | Reaction | Experiment Group | Control Group |
|---|---|---|---|
| PEU-2 | CuAAC | Chromeo 488 azide<br>CuSO$_4$, sodium carbonate | Chromeo 488 azide<br>sodium carbonate |
| PEU-3 | CuAAC | Two steps<br>1. alkyne-RGD-biotin<br>   CuSO$_4$, sodium carbonate<br>2. (TRITC)-conjugated streptavidin | Two Steps<br>1. alkyne-RGD-biotin<br>   sodium carbonate<br>2. (TRITC)-conjugated streptavidin |
| PEU-4 | Thiol-ene | FITC-RGD-thiol, I-2959 | FITC-RGD-thiol |
| PEU-6 | Ene-type 2 | Two steps<br>1. Cyclic diazodicarboxamide (LXV)<br>2. Chromeo 488 azide<br>   CuSO$_4$, sodium carbonate | Two steps<br>1. Cyclic diazodicarboxamide (LXV)<br>2. Chromeo 488 azide<br>   sodium carbonate |
| PEU-7 | Hydrazine | Alexa Fluor 488 hydrazide | PEU-1 as fiber substrates<br>Alexa Fluor 488 hydrazide |
| PEU-7 | Aminooxy | Two steps<br>1. O-(prop-2-yn-1-yl)hydroxylamine<br>2. Chromeo 488 azide<br>   CuSO$_4$, sodium carbonate | Two steps<br>1. O-(prop-2-yn-1-yl)hydroxylamine<br>2. Chromeo 488 azide<br>   sodium carbonate |

PEU-2:

Nanofibers were incubated at ambient temperature in phosphate buffered saline (PBS, ×10) solution containing following reagents: CuSO$_4$ (0.1 mg/mL), sodium ascorbate (0.5 mg/mL), and Chromeo 488 azide (1 μg/mL). After 1 h, the fibers were washed thoroughly with PBS followed by deionized water. The fibers were dried under the flow of nitrogen and imaged with fluorescence microscope. In the control groups for PEU-2, there was no copper catalyst in the buffer solution. Fluorescent reagent (Chromeo 488 azide) would not be attached to the fibers compared to experimental groups.

PEU-3:

Following surface conjugation with alkyne-RGD-biotin is similar to the method described in PEU-2. After the surface derivation with alkyne-RGD-biotin, the nanofibers were incubated in PBS (×1) solution containing a rhodamine (TRITC)-conjugated streptavidin (5 μg/mL) overnight at room temperature. Fibers were washed thoroughly with PBS followed by deionized water. The fibers were dried under the flow of nitrogen and imaged with fluorescence microscope. In the control groups for PEU-3, there was no copper catalyst in the buffer solution. Alkyne-RGD-biotin would not be attached to the fibers compared to experimental groups. In the following step, there was no specific absorption of (TRITC)-conjugated streptavidin to fibers.

PEU-4:

Nanofibers were covered with 0.2 mL of PBS solution containing FITC-RGD-thiol (0.1 mg/mL) and 1-2959 (0.01 mg/mL). The fibers were exposed to UV light for 2 min (365 nm, intensity 10 mW/cm$^2$), and then washed thoroughly with PBS followed by deionized water. The fibers were dried under the flow of nitrogen and imaged with fluorescence microscope. Fmoc-RGD-thiol was coupled to the nanofiber surface also using thiol-ene radical addition. Nanofibers mats were soaked in PBS solution containing Fmoc-RGD-thiol (0.5 mg/mL) and 1-2959 (0.01 mg/mL). Those fibers were exposed to UV light for 2 min (365 nm, intensity 10 W/cm$^2$), and then washed thoroughly with PBS followed by deionized water. The fibers were dried under the flow of nitrogen. The UV-Vis absorption curve was recorded after dissolving the fibers in HFIP. In the control groups, there was no photo initiator 1-2959, and then no thiol-ene radical addition reaction. FITC-RGD-thiol would not be attached to the fibers through a chemical pathway.

PEU-6:

Nanofibers were incubated in freshly made alkyne derived cyclic diazodicarboxamide (LXV) solution (1 mg/mL, PBS buffer: CH$_3$CN=10:1 by volume) for 30 min. After being thoroughly washed with H$_2$O, the nanofibers were treated with Chromeo 488 azide using CuAAC method described in PEU-2. In the control groups for PEU-6, there was no copper catalyst in the second step. Fluorescent reagent (Chromeo 488 azide) would not be attached to the fibers compared to experimental groups.

PEU-7:

Nanofibers were incubated in acetic buffer solution (pH 4.5) containing Alexa Fluor 488 hydrazide for 10 min, followed by thorough wash with H$_2$O. The fibers were dried under the flow of nitrogen and imaged with fluorescence microscope. In two-step derivation, 0-(prop-2-yn-1-yl)hydroxylamine (LIV) was bonded to fiber surface via CuAAC, followed by the conjugation with Chromeo 488 azide. There were two control experiments for PEU-7. As to the hydrazine reaction, in the control group the PEU-1 nanofibers without tyrosine units were used as the templates. Fluorescent reagent (Alexa Fluor 488 hydrazide) would not be attached. As to the oxime condensation, in the control groups, there was no copper catalyst in the second step. Fluorescent reagent (Chromeo 488 azide) would not be attached to the fibers compared to experimental groups.

What is claimed is:

1. An amino acid based poly(ester urea) polymer functionalized to bond with a bioactive compound comprising:
   a phenylalanine-based diester monomer segment; and
   a tyrosine-based diester monomer segment, said tyrosine-based diester monomer segment having one or more pendent functional groups.

2. The amino acid based poly(ester urea) of claim 1 wherein said one or more pendent functional groups is functionalized to bond with a bioactive compound via a click reaction.

3. The amino acid based poly(ester urea) of claim 1 wherein said phenylalanine-based diester monomer segment has the formula:

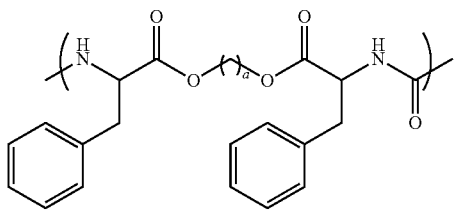

wherein a is an integer from 2 to 12.

4. The amino acid based poly(ester urea) of claim 1 wherein said tyrosine-based monomer segment has the formula:

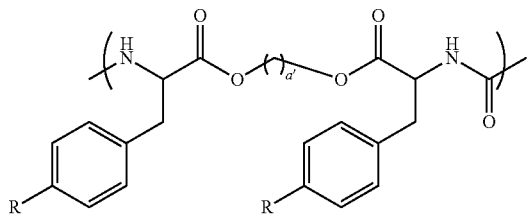

wherein R is an oxygen atom connected to said one or more pendent functional groups and a' is an integer from 2 to 12.

5. The amino acid based poly(ester urea) of claim 1 wherein said pendent functional group further comprises an alkyne group, an alkene group, an azide group, a benzyl protected phenol group, a ketone group, or a strained cyclooctyne.

6. The amino acid based poly(ester urea) of claim 4 wherein R is OH, $OCH_2C\equiv CH$, $OCH_2CH_2CH_2N_3$, $OCH_2CH_2CH_2CH=CH_2$, $OCH_2Ph$, or $OCOCH_2CH_2COCH_3$.

7. The amino acid based poly(ester urea) of claim 1 having the formula:

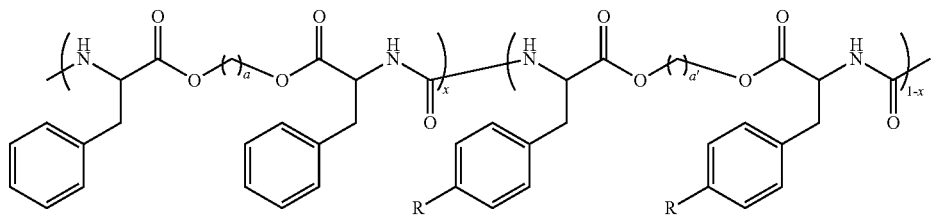

wherein R is an oxygen atom connected to an alkyl or aryl group containing an alkyne group, an alkene group, an azide group, a benzyl protected phenol group, a ketone group or a strained cyclooctyne; x is a mole fraction of from 0.001 to 0.990; and a and a' are integers from 2 to 12.

8. The amino acid based poly(ester urea) of claim 1 having a formula selected from the group consisting of:

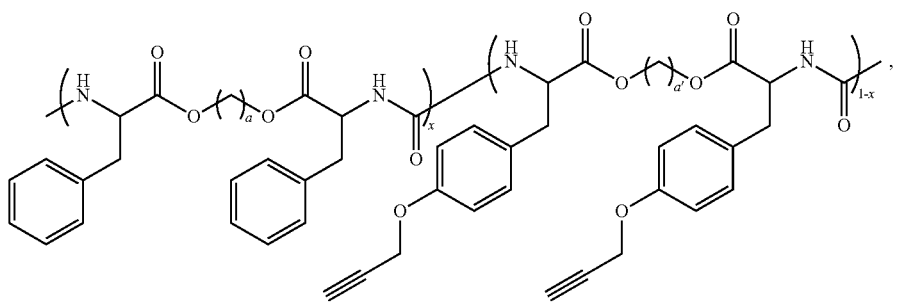

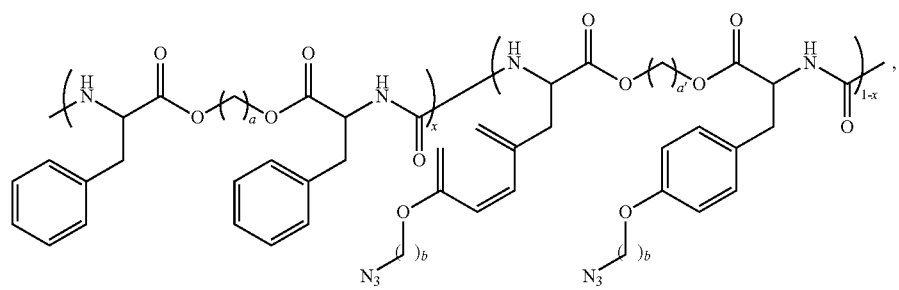
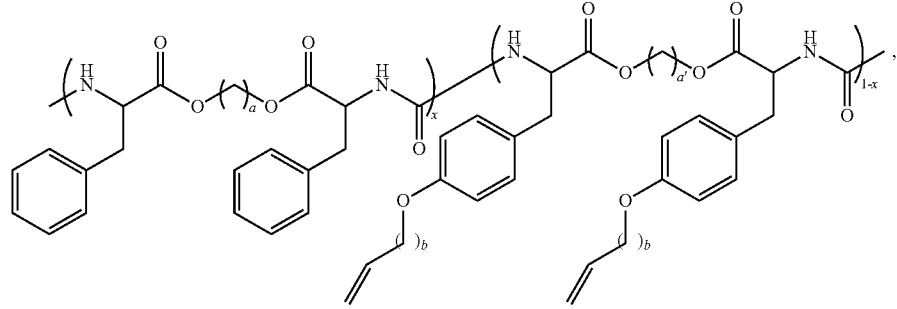
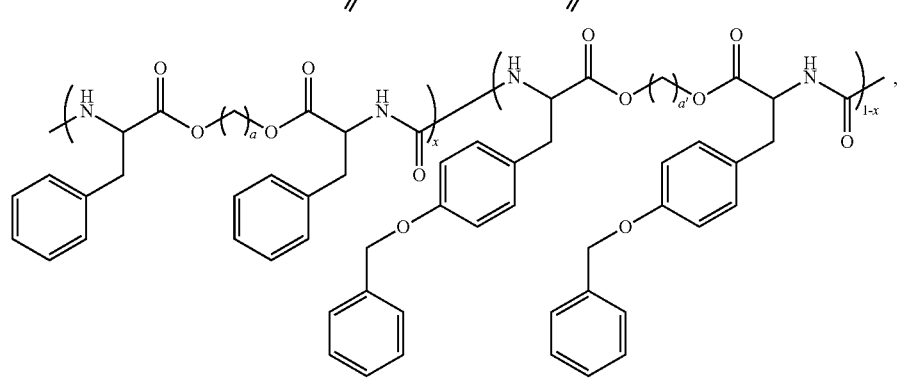
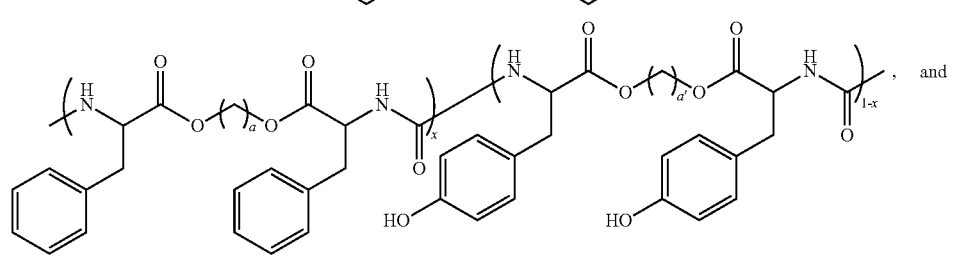, and
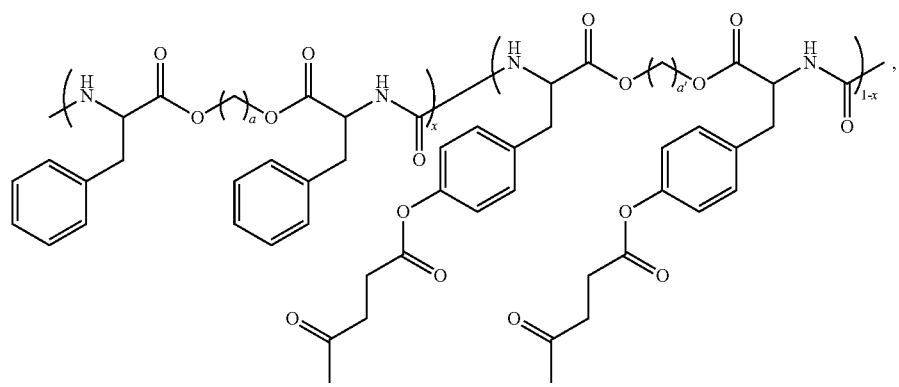, wherein a and a' are each an integer from 2 to 12; b is an integer from 1 to 8; and x is a molar fraction from 0.001 to 990.

9. The amino acid based poly(ester urea) of claim 1 further comprising a bioactive compound chemically bound to said one or more pendent functional groups.

10. The amino acid based poly(ester urea) of claim 9 wherein said bioactive compound is selected from the group consisting of peptides, carbohydrates, and growth factors, and combinations thereof.

11. The amino acid based poly(ester urea) of claim 9 wherein said bioactive compound is selected from the group consisting of Lys(biotin), bone morphogenic protein-2 (BMP-2), bone morphogenic protein-7 (BMP-7), osteogenic growth peptide (OGP), the c-terminal fragment of OGP [10-14] (YGFGG), GRGDS (RGD), and combinations thereof.

12. A formed polymer structure, coating or film comprising the amino acid based poly(ester urea) polymer functionalized to bond with a bioactive compound of claim 1, wherein said amino acid based poly(ester urea) polymer further comprises: a phenylalanine-based diester monomer segment and a tyrosine-based diester monomer segment, said tyrosine-based monomer segment having one or more pendent functional groups.

13. The formed polymer structure, coating or film of claim 12 wherein said formed polymer structure, coating or film comprises a fiber, a tissue scaffold, a tube, a pin, a film, a coating, or a medical device.

14. The formed polymer structure, coating or film of claim 12 further comprising:
  a bioactive compound chemically bound to said one or more pendent functional groups of said amino acid based poly(ester urea) polymer.

15. The formed polymer structure, coating or film of claim 14 wherein said bioactive compound comprises a peptide, a carbohydrate, or a growth factor.

16. A novel amino acid-based diester monomer for use in forming the amino acid-based poly(ester ureas) functionalized to bond with a bioactive compounds of claim 1, having the formula:

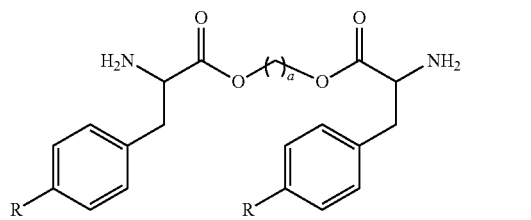

wherein R is a pendent functional group and a is an integer from 2 to 12.

17. The novel amino acid-based diester monomer of claim 16 wherein R comprises an oxygen atom connected to alkyl or aryl group containing a moiety capable of forming a chemical bond through a click reaction.

18. The novel amino acid-based diester monomer of claim 16 wherein R comprises an oxygen atom connected to an alkyl or aryl group containing an alkyne group, an alkene group, an azide group, a benzyl protected phenol group, or a ketone group.

19. The novel amino acid-based diester monomer of claim 16 wherein R is OH, OCH$_2$C≡CH, OCH$_2$CH$_2$CH$_2$N$_3$, OCH$_2$CH$_2$CH=CH$_2$, OCH$_2$Ph, or OCOCH$_2$CH$_2$COCH$_3$.

20. The novel amino acid-based diester monomer of claim 16 having a formula selected from the group consisting of:

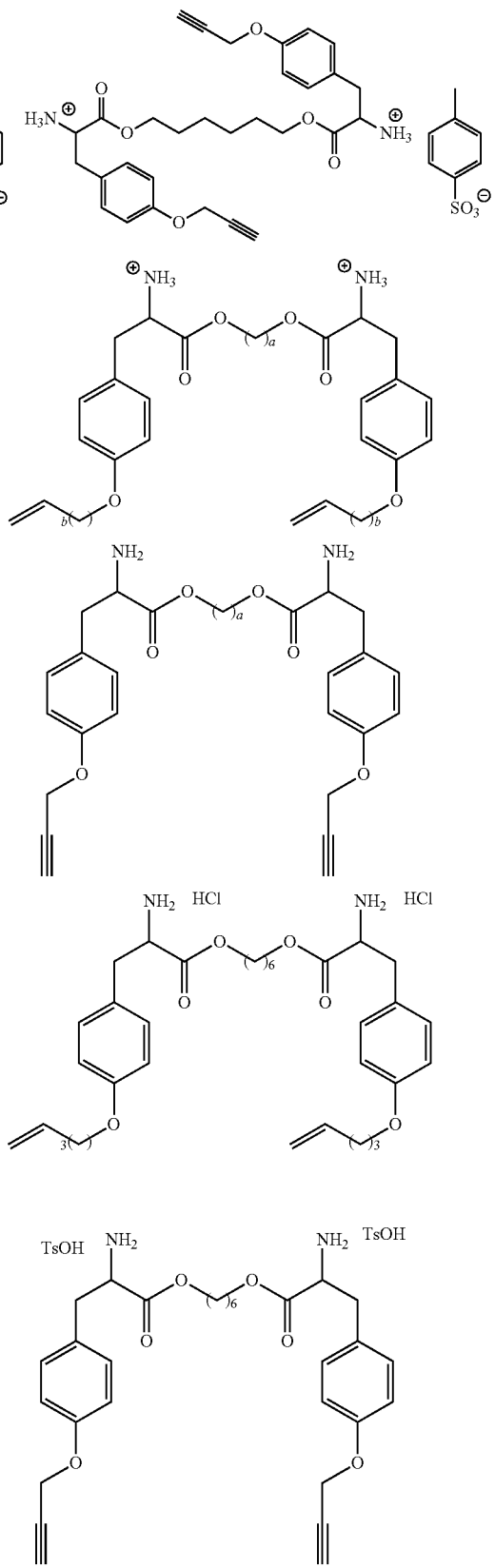

89
-continued
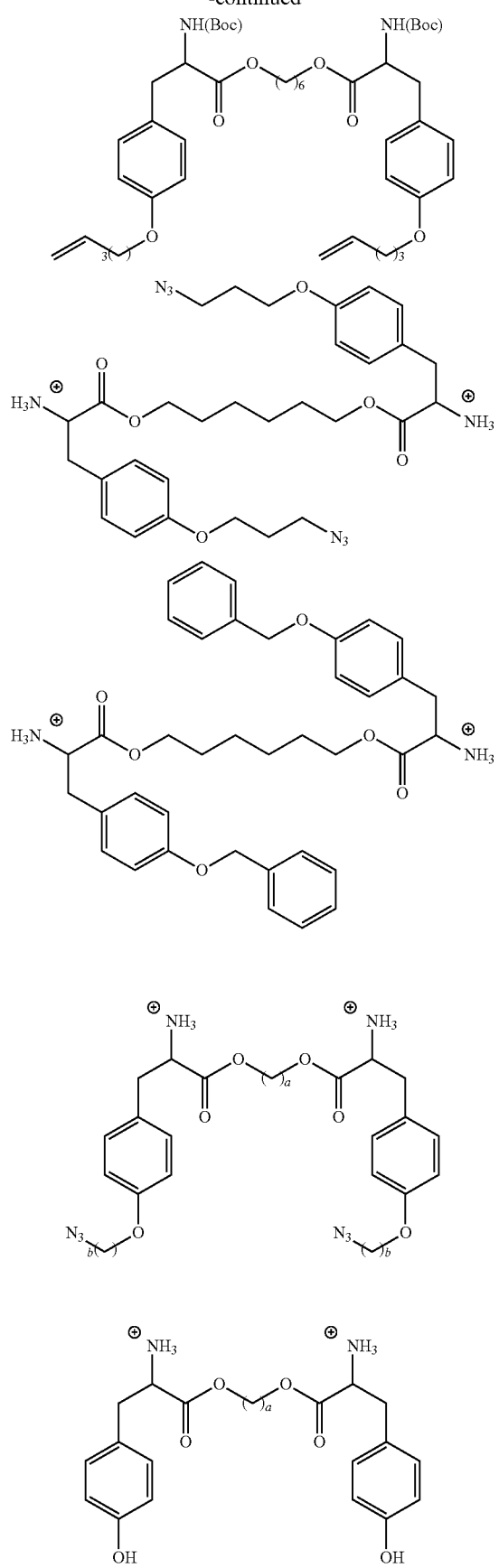
90
-continued
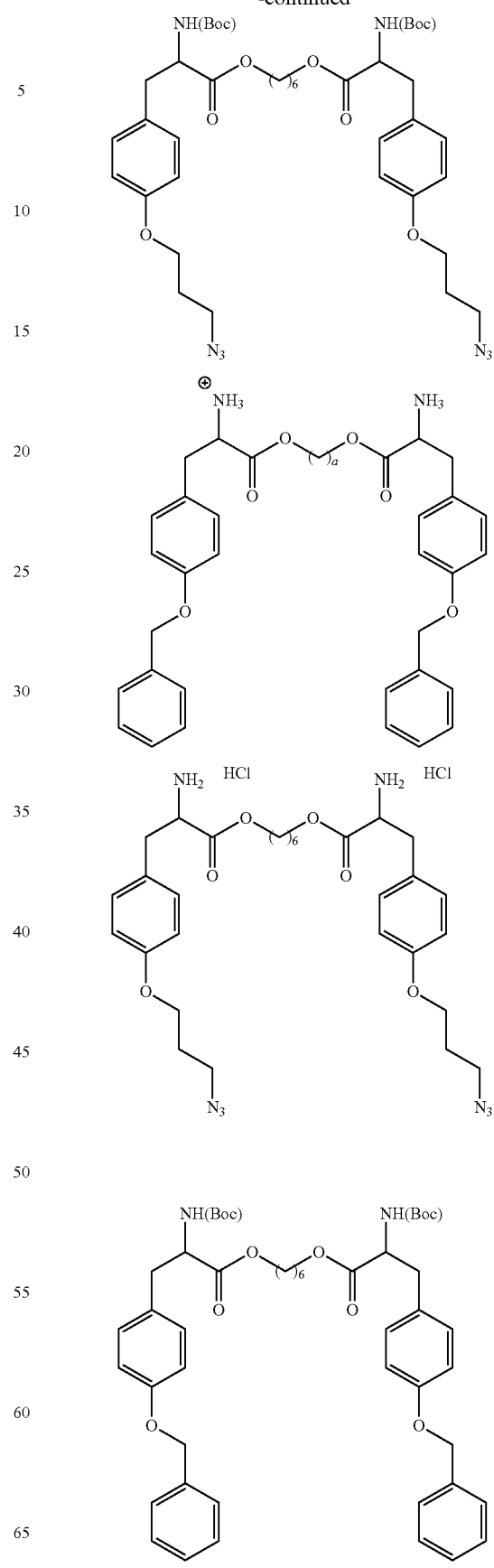

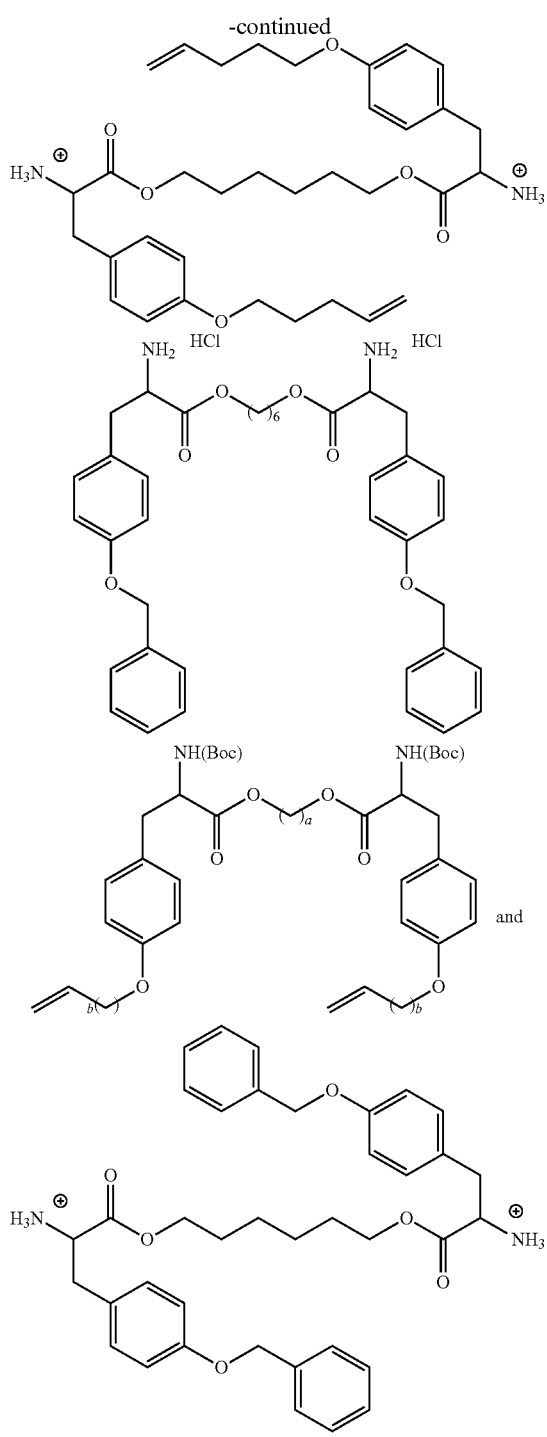

and wherein a is an integer from 2 to 12; and b is an integer from 1 to 8.

21. A method for making the amino acid-based poly(ester urea) functionalized to bond with a bioactive compound of claim 1 comprising:

A. dissolving a phenylalanine-based diester monomer, a tyrosine-based diester monomer having one or more pendent functional groups, and a base selected from the group consisting of sodium carbonate, or potassium carbonate and combinations thereof in an aqueous solution;

B. reducing the temperature of the solution of step A to a temperature of from about −5° C. to about 5° C.;

C. adding a solution comprising triphosgene or phosgene and a suitable organic solvent to the solution of step B forming an interfacial mixture having an organic phase and an aqueous phase; and D. separating the organic and aqueous phases of the interfacial mixture of step C and collecting and purifying said organic phase to produce the amino acid-based poly(ester urea) functionalized to bond with a bioactive compound.

22. The method of claim 21 wherein said one or more pendent functional groups comprises a benzyl protected phenol, the method further comprising:

E preparing an amino acid-based poly(ester urea) functionalized to bond with a bioactive compound as set forth in steps A through D above, wherein one or more pendent functional groups comprises a benzyl protected phenol;

F collecting, purifying and drying said amino acid-based poly(ester urea) functionalized to bond with a bioactive compound;

G dissolving the amino acid-based poly(ester urea) of step I in a suitable organic solvent and adding a catalytic amount of palladium on carbon to form a suspension;

H stirring the suspension of step J under a hydrogen atmosphere at a temperature of from about 45° C. to about 55° C., for from 1 hour to about 24 hours, at a pressure of from 50 to about 70 psi.

I filtering the suspension of step K through a Celite column;

J collecting and concentrating the filtrate;

K adding the filtrate of step M to an excess volume of water to precipitate out a functionalized amino acid-based poly(ester urea) having the formula:

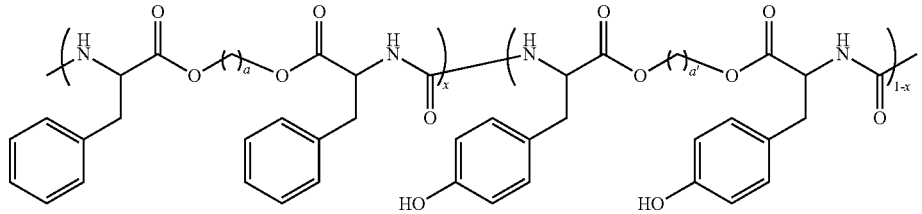

wherein a and a' are each an integer from 2 to 12; and x is a mole fraction of from 0.001 to 990.

23. The method of claim 22 further comprising:

L dissolving the amino acid-based poly(ester urea) of step N in a suitable organic solvent;

M adding stoicheometrically appropriate quantities of levulinic acid and suitable base;

N cooling the solution of step Q to a temperature of from about −5° C. to about 5° C. and adding a stoicheometrically appropriate quantity of 1,3-diisopropyl cabodiimide (DIPC);

O allowing the solution of step R to warm up to room temperature and stirring for from about 2 hours to about 24 hours; and P adding the mixture of step S to an excess volume of methanol or ethanol to produce an amino acid-based poly(ester urea) having the formula:

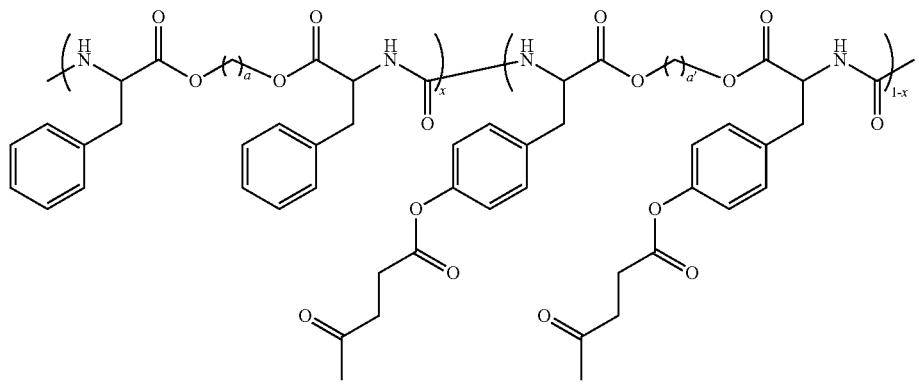

wherein a and a' are integers from 2 to 12 and x is a mole percentage of from 0.001 to 990.

24. A method for making a novel amino acid-based diester monomer for forming the amino acid-based poly(ester ureas) functionalized to bond with a bioactive compound of claim 1 comprising:

A. dissolving functionalized tyrosine precursor group in a suitable solvent;

B. reacting the hydroxyl of said functionalized tyrosine precursor group with a functionalized alkyl halide or alkyl azide having a pendent functional group, thereby attaching said pendent functional group to the phenyl oxygen of said functionalized tyrosine precursor;

C. determine whether the product of step B has a protected ester group and if it does, reacting the product of step B with a base to deprotect said ester group;

D. reacting the compound of step C with a stoicheometrically appropriate quantity of a diol having from 2 to 12 carbon atoms to produce a functionalized tyrosine-based monomer;

E. determining whether the compound of step D has a protected amine group and if it does, dissolving the compound of step D in HCl and dioxane under a nitrogen or argon atmosphere to deprotect the amine group and produce a novel amino acid-based diester monomer for use in forming an amino acid-based poly(ester ureas) functionalized to bond with bioactive compounds.

* * * * *